US012133714B2

(12) United States Patent
Ben-Yakar et al.

(10) Patent No.: US 12,133,714 B2
(45) Date of Patent: Nov. 5, 2024

(54) LINE EXCITATION ARRAY DETECTION MICROSCOPY

(71) Applicant: BOARD OF REGENTS, THE UNIVERSITY OF TEXAS SYSTEM, Austin, TX (US)

(72) Inventors: Adela Ben-Yakar, Austin, TX (US); Tianqi Li, Poway, CA (US); Chris Martin, Austin, TX (US); Peisen Zhao, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 912 days.

(21) Appl. No.: 17/054,266

(22) PCT Filed: May 10, 2019

(86) PCT No.: PCT/US2019/031763
§ 371 (c)(1),
(2) Date: Nov. 10, 2020

(87) PCT Pub. No.: WO2019/217846
PCT Pub. Date: Nov. 14, 2019

(65) Prior Publication Data
US 2021/0161385 A1 Jun. 3, 2021

Related U.S. Application Data

(60) Provisional application No. 62/669,573, filed on May 10, 2018.

(51) Int. Cl.
*G02B 21/00* (2006.01)
*A61B 5/00* (2006.01)
*G01N 21/64* (2006.01)

(52) U.S. Cl.
CPC .......... *A61B 5/0071* (2013.01); *A61B 5/0082* (2013.01); *G01N 21/6458* (2013.01);
(Continued)

(58) Field of Classification Search
CPC ... A61B 5/0071; A61B 5/0082; A61B 5/0062; G01N 21/6458; G01N 20/6456;
(Continued)

(56) References Cited

U.S. PATENT DOCUMENTS

| 5,691,839 A | 11/1997 | Kobayashi |
| 6,400,453 B1 | 6/2002 | Hansen |

(Continued)

FOREIGN PATENT DOCUMENTS

| EP | 3214430 A1 | 6/2017 | |
| WO | WO-2014007763 A1 * | 1/2014 | ............ G01J 1/0403 |
| WO | 2016054474 | 4/2016 | |

OTHER PUBLICATIONS

International Search Report and Written Opinion for International Application No. PCT/US2019/031763 dated Aug. 5, 2019.
(Continued)

*Primary Examiner* — Arnel C Lavarias
(74) *Attorney, Agent, or Firm* — Meunier Carlin & Curfman LLC

(57) ABSTRACT

Systems and methods for line excitation array detection (LEAD) microscopy. The systems and methods include an excitation beam from an optical beam source and a subject of interest. Light is scanned across the subject of interest and optical signals are detected using a parallel optical detection means. A number of mechanical, acoustic and/or optical components such as scanning mirrors, DMDs, OADs, electric motors may be used separately or in conjunction to aid in the scanning of the excitation beam across the subject of interest.

20 Claims, 32 Drawing Sheets

(52) U.S. Cl.
CPC ..... *G02B 21/0036* (2013.01); *G02B 21/0048* (2013.01); *G02B 21/006* (2013.01); *G02B 21/0072* (2013.01); *G02B 21/0076* (2013.01)

(58) Field of Classification Search
CPC ... G01N 2021/6463; G01N 2021/6467; G01N 21/6486; G02B 21/0036; G02B 21/0048; G02B 21/006; G02B 21/0072; G02B 21/0076; G02B 21/00; G02B 21/0004; G02B 21/002; G02B 21/0032; G02B 21/0052; G02B 21/008; G02B 21/06; G02B 21/36; G02B 21/361; G02B 21/365; G02B 21/367
USPC ....... 359/363, 362, 368, 369, 385, 388, 390, 359/433
See application file for complete search history.

(56) References Cited

U.S. PATENT DOCUMENTS

| | | | |
|---|---|---|---|
| 6,501,603 | B2 | 6/2002 | Kasahara |
| 6,922,279 | B2 | 7/2005 | Sun et al. |
| 7,116,407 | B2 | 10/2006 | Hansen et al. |
| 8,503,076 | B2 | 8/2013 | Birk et al. |
| 8,660,332 | B2 | 2/2014 | Ortyn et al. |
| 9,730,649 | B1 | 8/2017 | Jepsen |
| 2006/0071143 | A1 | 4/2006 | Saggau et al. |
| 2006/0140462 | A1 | 6/2006 | Saggau et al. |
| 2007/0057211 | A1 | 3/2007 | Bahlman et al. |
| 2009/0174937 | A1 | 7/2009 | Holy et al. |
| 2010/0214654 | A1 | 8/2010 | Birk et al. |
| 2010/0284024 | A1 | 11/2010 | Vucinic et al. |
| 2012/0281271 | A1 | 11/2012 | Sandstrom et al. |
| 2015/0338628 | A1 | 11/2015 | Knebel et al. |
| 2015/0338718 | A1 | 11/2015 | Zhang et al. |
| 2016/0231575 | A1 | 8/2016 | Shoham et al. |
| 2016/0327779 | A1 | 11/2016 | Hillman |
| 2017/0182321 | A1 | 6/2017 | Kass et al. |
| 2019/0302437 | A1* | 10/2019 | Hillman ............. G02B 21/0032 |

OTHER PUBLICATIONS

"Acousto-optic Theory Application Notes," AA Opto-Electronic, retrieved from http://www.aaoptoelectronic.com/wp-content/uploads/documents/AAOPTO-Theory2013-4.pdf, 2013, 9 pages.

Carriles, R., et al., "Invited Review Article: Imaging techniques for harmonic and multiphoton absorption fluorescence microscopy," Review of Scientific Instruments, vol. 80, No. 8, 2009, pp. 081101-1 to 081101-23.

Marblestone, A.H., et al., "Physical Principles for Scalable Neural Recording," Frontiers in Computational Neuroscience, vol. 7, Article 137, 2013, 34 pages.

Pégard, N., et al., "Flow-Scanning Microfluidic Imaging," Chapter 6: Advances in Microfluidics—New Applications in Biology, Energy, and Materials Sciences, 2016, pp. 136-161.

Power, R.M., et al., "A guide to light-sheet fluorescence microscopy for multiscale imaging," Nature Methods, vol. 14, No. 4, 2017, pp. 360-373.

"Resonant Scanning in Laser Confocal Microscopy," Nikon's MicroscopyU, retrieved from https://www.microscopyu.com/techniques/confocal/resonantscanning-in-laser-confocalmicroscopy, 2016, 17 pages.

"Trigger-To-Image Reliability Framework," Teledyne Dalsa, Technology Primer, 2016, 16 pages.

Extended European Search Report, dated Jan. 25, 2022, received in connection with corresponding EP Patent Application No. 19800640.5.

"Union Biometrica | COPAS Flow Pilot Platform Overview," Nov. 2009.

Abrahamsson, et al. "Fast multicolor 3D imaging using aberration-corrected multifocus microscopy." Nat. Methods 10, 60-63 (2013).

Ahrens, et al., "Whole-brain functional imaging at cellular resolution using light-sheet microscopy." Nat. Methods 10, 413-420 (2013).

Alexander, et al., "Use of C. elegans as a model to study Alzheimer's disease and other neurodegenerative diseases." Front. Genet. 5, 1-21 (2014).

Anselmi, et al., "Three-dimensional imaging and photostimulation by remote-focusing and holographic light patterning." Proc. Natl. Acad. Sci. 108, 19504-19509 (2011).

Ariav, et al. "Submillisecond precision of the input-output transformation function mediated by fast sodium dendritic spikes in basal dendrites of CA1 pyramidal neurons." J. Neurosci. 23(21), 7750-8 (2003).

Bean, "The action potential in mammalian central neurons." Nat. Rev. Neurosci. 8, (2007).

Bègue, et al. "Two-photon excitation in scattering media by spatiotemporally shaped beams and their application in optogenetic stimulation." Biomed. Opt. Express 4, 2869 (2013).

Benedetti, et al. "Achieving confocal-point performance in confocal-line microscopy", Bioimaging 2, 122-130 (1994).

Ben-Yakar, et al., "Microfluidics for the analysis of behavior, nerve regeneration, and neural cell biology in C. elegans." Curr. Opin. Neurobiol. 19, 561-567 (2009).

Block E. and Squier J. "Simultaneous spatial and temporal focusing for tissue ablation." Biomed. Opt. Express 4(6), (2013).

Bosworth, et al., "High-speed flow microscopy using compressed sensing with ultrafast laser pulses," Opt. Express 23(8), 10521-10532 (2015).

Botcherby, E. J. et al. "Aberration-free three-dimensional multiphoton imaging of neuronal activity at kHz rates." Proc. Natl. Acad. Sci. U. S. A. 109, 2919-24 (2012).

Bouchard, M. B. et al. "Swept confocally-aligned planar excitation (SCAPE) microscopy for high-speed volumetric imaging of behaving organisms." Nat. Photonics 9, 113-119 (2015).

Brenner, S. "The genetics of Caenorhabditis elegans." Genetics 77, 71-94 (1974).

Bromberger, et al., "FPGA-accelerated Richardson-Lucy deconvolution for 3D image data." 2016 IEEE 13th Int. Symp. Biomed. Imaging 132-135 (2016).

Buchthal, et al., "Evoked action potentials and conduction velocity in human sensory nerves," Brain Res. 3(1), (1966).

Cha, et al., "Non-descanned multifocal multiphoton microscopy with a multianode photomultiplier tube," AIP Adv. 5(8), (2015).

Chan, et al. "Digitally synthesized beat frequency-multiplexed fluorescence lifetime spectroscopy." Biomed. Opt. Express 5, 4428-36 (2014).

Chang, "Acousto-optic devices and applications." 1995, 55 pages.

Chen, et al. "Lattice light-sheet microscopy: Imaging molecules to embryos at high spatiotemporal resolution." Science 346, 1257998-1257998 (2014).

Chen, et al. "Ultrasensitive fluorescent proteins for imaging neuronal activity." Nature 499(7458), 295-300 (2013).

Chen, L. et al. "Axon regeneration pathways identified by systematic genetic screening in C. elegans." Neuron 71, 1043-57 (2011).

Chen, et al., "Functional mapping of single spines in cortical neurons in vivo." Nature 475, 501-505 (2011).

Cheng, et al., "Simultaneous two-photon calcium imaging at different depths with spatiotemporal multiplexing." Nat. Methods 8, 139-42 (2011).

Chung, et al., "Automated on-chip rapid microscopy, phenotyping and sorting of C. elegans." Nature methods, 5(7), 637-43 (2008).

Cinar, et al., "Expression Profiling of GABAergic motor neurons in Caenorhabditis elegans." Curr Biol 15, 340-346 (2005).

Coates, et al. sCMOS: scientific CMOS technology, a high-performance imaging breakthrough (White Paper), 1-14 (2009).

Coffman, V. C. & Wu, J.-Q. "Counting protein molecules using quantitative fluorescence microscopy." Trends Biochem. Sci. 37, 499-506 (2012).

Cornaglia, M., Lehnert, T. & Gijs, M. A. M. "Microfluidic systems for high-throughput and high-content screening using the nematode Caenorhabditis elegans." Lab Chip (2017). doi:10.1039/C7LC00509A.

(56) References Cited

OTHER PUBLICATIONS

Crane, M. M. et al. Autonomous screening of C. elegans identifies genes implicated in synaptogenesis. Nat. Methods 9, 977-980 (2012).
Dana, et al. Line temporal focusing characteristics in transparent and scattering media. Opt. Express 21(5), 5677 (2013).
Dana, H. & Shoham, S. Remotely scanned multiphoton temporal focusing by axial grism scanning. Opt. Lett. 37, 2913 (2012).
Dana, H. et al. Hybrid multiphoton volumetric functional imaging of large-scale bioengineered neuronal networks. Nat. Commun. 5, 1-7 (2014).
Dean, P. Roudot, E. S. Welf, G. Danuser, and R. Fiolka. Deconvolution-free Subcellular Imaging with Axially Swept Light Sheet Microscopy. Biophys. J. 108(12), 2807-2815 (2015).
Diebold, E. D., Buckley, B. W., Gossett, D. R. & Jalali, B. Digitally-synthesized beat frequency multiplexing for sub-millisecond fluorescence microscopy. Nat. Photon. 7, 806-810 (2013).
Duocastella, M. et al. Fast inertia-free volumetric light-sheet microscope. ACS Photon. 4, 1797-1804 (2017).
Durst et al. Simultaneous spatial and temporal focusing for axial scanning. Opt. Express 14(25), 12243 (2006).
Durst, G. Zhu, and C. Xu, "Simultaneous spatial and temporal focusing in nonlinear microscopy," Opt. Commun. 281(7), 1796-1805 (2008).
Eguchi, M. & Yamaguchi, S. In vivo and in vitro visualization of gene expression dynamics over extensive areas of the brain. Neuroimage 44, 1274-1283 (2009).
Fahrbach, F. O., Voigt, F. F., Schmid, B., Helmchen, F. & Huisken, J. Rapid 3D light-sheet microscopy with a tunable lens. Opt. Express 21, 21010 (2013).
Feigin, "Global, regional, and national burden of neurological disorders during 1990-2015: a systematic analysis for the Global Burden of Disease Study 2015," Lancet Neurol. 16(11), 877-897 (2017).
Fernandez-Alfonso, T. et al. Monitoring synaptic and neuronal activity in 3D with synthetic and genetic indicators using a compact acousto-optic lens two-photon microscope. J. Neurosci. Methods 222, 69-81 (2014).
Field, D. G. Winters, and R. A. Bartels, "Phase-sensitive fluorescent imaging with coherent reconstruction," arXiv (2015).
Futia, G., Schlup, P., Winters, D. G. & Bartels, R. A. Spatially-chirped modulation imaging of absorbtion and fluorescent objects on single-element optical detector. Opt. Express 19, 1626-1640 (2011).
Ghorashian, N. Automated Microfluidic Platforms To Facilitate Nerve Degeneration Studies With C. Elegans. (The University of Texas at Austin 2013). 139 pages.
Ghorashian, N., Gökçe, S. K., Guo, S. X., Everett, W. N. & Ben-Yakar, A. An automated microfluidic multiplexer for fast delivery of C. elegans populations from multiwells. PLoS One 8, e74480 (2013).
Gobel, W. & Helmchen, F. New Angles on Neuronal Dendrites In Vivo. J. Neurophysiol. 98, 3770-3779 (2007).
Goda, a. Ayazi, D. R. Gossett, J. Sadasivam, C. K. Lonappan, E. Sollier, a. M. Fard, S. C. Hur, J. Adam, C. Murray, C. Wang, N. Brackbill, D. Di Carlo, and B. Jalali, "High-throughput single-microparticle imaging flow analyzer," Proc. Natl. Acad. Sci. 109(29), 11630-11635 (2012).
Goda, K., Tsia, K. K. & Jalali, B. Serial time-encoded amplified imaging for realtime observation of fast dynamic phenomena. Nature 458, 1145-1149 (2009).
Gong, Y. et al. High-speed recording of neural spikes in awake mice and flies with a fluorescent voltage sensor. Science 350(6266): 361-1366 (2015).
Gosai, J. H. Kwak, C. J. Luke, O. S. Long, D. E. King, K. J. Kovatch, P. A. Johnston, T. Y. Shun, J. S. Lazo, D. H. Perlmutter, G. A. Silverman, and S. C. Pak, "Automated high-content live animal drug screening using C. elegans expressing the aggregation prone serpin α1-antitrypsin Z," PLoS One 5(11), (2010).
Grewe, B. F., Langer, D., Kasper, H., Kampa, B. M. & Helmchen, F. High-speed in vivo calcium imaging reveals neuronal network activity with near-millisecond precision. Nat. Methods 7, 399-405 (2010).
Grewe, B. F., Voigt, F. F., van 't Hoff, M. & Helmchen, F. Fast two-layer two-photon imaging of neuronal cell populations using an electrically tunable lens. Biomed. Opt. Express 2, 2035 (2011).
Grienberger C. and A. Konnerth. Imaging Calcium in Neurons. Neuron 73(5), 862-885 (2012).
Hamamatsu. Photomultiplier Tubes: Basics and Applications. (Hamamatsu Photonics K.K., 2007).
Hosaka, S., Seya, E., Harada, T. & Takanashi, A. High speed laser beam scanning using an acousto-optical deflector (AOD). Jpn. J. Appl. Phys. 26, 1026-1030 (1987).
Howard, S. S., Straub, A., Horton, N. G., Kobat, D. & Xu, C. Frequency-multiplexed in vivo multiphoton phosphorescence lifetime microscopy. Nat. Photonics 7, 33-37 (2012).
Huisken, J. Swoger, D. B. Filippo, J. Witbrodt, and E. H. K. Stelzer, "Optical Sectioning Deep inside Live Embryos by Selective Plane Illumination Microscopy," Science (80-. ). 305(5686), 1007-1009 (2004).
Iyer, T. Hoogland, and P. Saggau, "Fast Functional Imaging of Single Neurons Using Random-Access Multiphoton (RAMP) Microscopy," J. Neurophysiol. 95(1), 535-545 (2005).
Jabbour, et al. Optical axial scanning in confocal microscopy using an electrically tunable lens. Biomed. Opt. Express 5(2), 645 (2014).
Jacobs, R. Zelmann, J. Jirsch, R. Chander, C. Chatillon, F. Dubeau, and J. Gotman, "High frequency oscillations (80-500 Hz) in the preictal period in patients with focal seizures," Epilepsia 50(7), 1780-1792 (2009).
Ji, N., Freeman, J. & Smith, S. L. Technologies for imaging neural activity in large volumes. Nat. Neurosci. 19, 1154-1164 (2016).
Kaletta, T. & Hengartner, M. O. Finding function in novel targets: C. elegans as a model organism. Nat. Rev. 5, 387-398 (2006).
Kalmbach, et al. Brain surface temperature under a craniotomy. J. Neurophysiol. 108(11), 3138-3146 (2012).
Kaplan, N. Friedman, and N. Davidson. Acousto-optic lens with very fast focus scanning. Opt. Lett. 26(14), 1078-1080 (2001).
Katona, G. et al. Fast two-photon in vivo imaging with three-dimensional random-access scanning in large tissue volumes. Nat. Methods 9, 201-208 (2012).
Kazemipour, et al., "Kilohertz frame-rate two-photon tomography," Nat Methods. Aug. 2019; 16(8): 778-786. doi:10.1038/s41592-019-0493-9.
Keller and M. B. Ahrens, "Visualizing whole-brain activity and development at the single-cell level using light-sheet microscopy," Neuron 85(3), 462-483 (2015).
Keller, P. J., Schmidt, A. D., Wittbrodt, J. & Stelzer, E. H. K. Reconstruction of zebrafish early embryonic development by scanned light sheet microscopy. Science 322, 1065-1069 (2008).
Kerse, C., Kalayciollu, H., Elahi, P., Akçaalan, Ö. & Ilday, F. Ö. 3.5-GHz intra-burst repetition rate ultrafast Yb-doped fiber laser. Opt. Commun. 366, 404-409 (2016).
Kim, K. H. et al. Multifocal multiphoton microscopy based on multianode photomultiplier tubes. Opt. Express 15, 11658-11678 (2007).
Kim, K. H., Ragan, T., Previte, M. J., Bahlmann, K., Harley, B. A., Wiktor-Brown, D. M., . . . & So, P. T. (2007). Three-dimensional tissue cytometer based on high-speed multiphoton microscopy. Cytometry Part A, 71(12), 991-1002.
Kirkby, et al., A compact acousto-optic lens for 2D and 3D femtosecond based 2-photon microscopy. Opt. Express 18(13), 13720 (2010).
Kumar, S. et al. Multifocal multiphoton excitation and time correlated single photon counting detection for 3-D fluorescence lifetime imaging. Opt. Express 15, 12548-12561 (2007).
Lechleiter, J. D., Lin, D.-T. & Sieneart, I. Multi-photon laser scanning microscopy using an acoustic optical deflector. Biophys. J. 83, 2292-9 (2002).
Lemon, W. C. et al. Whole-central nervous system functional imaging in larval *Drosophila*. Nat. Commun. 6, 7924 (2015).
Lichtman J. and Conchello J. Fluorescence Microscopy. Nat. Methods 2(12), (2005).

(56) References Cited

OTHER PUBLICATIONS

Lin and M. J. Schnitzer. Genetically encoded indicators of neuronal activity. Nat. Neurosci. 19(9), 1142-1153 (2016).
Mank, O. Griesbeck, and F. S. E. T. C. Genetically Encoded Calcium Indicators. Chem. Rev. 108(5), 1550-1564 (2008).
Martin, et al., "Line excitation array detection microscopy at 0.8 million frames per second," Nat. Commun. 9, (2018).
McGorty, R. et al. Open-top selective plane illumination microscope for conventionally mounted specimens. Opt. Express 23, 16142-53 (2015).
Mcgorty, R., Xie, D. & Huang, B. High-NA open-top selective-plane illumination microscopy for biological imaging. Opt. Express 25, 17798 (2017).
Mertz, J. & Kim, J. Scanning light-sheet microscopy in the whole mouse brain with HiLo background rejection. J. Biomed. Opt. 15, 016027 (2010).
Mikami, H. et al. Ultrafast confocal fluorescence microscopy beyond the fluorescence lifetime limit. Optica 5, 117 (2018).
Mondal, S. et al. Large-scale microfluidics providing high-resolution and high-throughput screening of Caenorhabditis elegans poly-glutamine aggregation model. Nat. Commun. 7, 13023 (2016).
Morley, J. F., Brignull, H. R., Weyers, J. J. & Morimoto, R. I. The threshold for polyglutamine-expansion protein aggregation and cellular toxicity is dynamic and influenced by aging in Caenorhabditis elegans. Proc. Natl. Acad. Sci. U. S. A. 99, 10417-22 (2002).
Munich, M. E. & Perona, P. Continuous dynamic time warping for translation-invariant curve alignment with applications to signature verification. Proc. Seventh IEEE Int. Conf. Comput. Vis. 15, 108-115 vol. 1 (1999).
Nadella, K. M. N. S. et al. Random-access scanning microscopy for 3D imaging in awake behaving animals. Nat. Methods 13, 1001-1004 (2016).
Nakai, et al. High-speed microscopy with an electrically tunable lens to image the dynamics of in vivo molecular complexes. Rev. Sci. Instrum. 86(1), (2015).
Nir, et al., "Acousto-optic scanning system with fast non-linear scan." 2000, 1762-1764.
Olarte, O. E., Andilla, J., Artigas, D. & Loza-Alvarez, P. Decoupled illumination detection in light sheet microscopy for fast volumetric imaging. Optica 2, 702 (2015).
Oron et al. Temporal focusing microscopy. Cold Spring Harb. Protoc. 2015(2), 145-151 (2015).
Oron, et al. Scanningless depth-resolved microscopy. Opt. Express 13(5), 1468 (2005).
Papagiakoumou, E. et al. Functional patterned multiphoton excitation deep inside scattering tissue. Nat. Photonics 7, 274-278 (2013).
Penzes, et al. Dendritic spine pathology in neuropsychiatric disorders. Nat. Neurosci. 14(3), 285-293 (2011).
Philipp, et al. Volumetric HiLo microscopy employing an electrically tunable lens. Opt. Express 24(13), 15029 (2016).
Picot, et al. Temperature Rise under Two-Photon Optogenetic Brain Stimulation. Cell Rep. 24(5), 1243-1253.e5 (2018).
Pikto-Pietkiewicz, W. The effect of dronedarone on the frequency of cardiovascular events in patients with atrial fibrillation—ATHENA studies. Kardiol. Pol. 67, 455-456 (2009).
Podgorski K. and G. Ranganathan. Brain heating induced by near-infrared lasers during multiphoton microscopy. J. Neurophysiol. 116(3), 1012-1023 (2016).
Prevedel, A. J. Verhoef, A. J. Pernía-Andrade, S. Weisenburger, B. S. Huang, T. Nöbauer, A. Fernández, J. E. Delcour, P. Golshani, A. Baltuska, and A. Vaziri, "Fast volumetric calcium imaging across multiple cortical layers using sculpted light," Nat. Methods 13(12), 1021-1028 (2016).
Prevedel, R. et al. Simultaneous whole-animal 3D imaging of neuronal activity using light-field microscopy. Nat. Methods 11, 727-30 (2014).
Pulak, R. Techniques for analysis, sorting, and dispensing of C. elegans on the COPAS flow-sorting system. Methods Mol. Biol. 351, 275-286 (2006).

Quirin, N. Vladimirov, C.-T. Yang, D. S. Peterka, R. Yuste, and M. B. Ahrens, "Calcium imaging of neural circuits with extended depth-of-field light-sheet microscopy," Opt. Lett. 41(5), 855 (2016).
Ragan, T. et al. High-resolution whole organ imaging using two-photon tissue cytometry. J. Biomed. Opt. 12, 14015 (2007).
Reddy, et al., "Fast three-dimensional laser scanning scheme using acousto-optic deflectors.," J. Biomed. Opt. 10(6), 064038 (2005).
Reddy, G., Kelleher, K., Fink, R. & Saggau, P. Three-dimensional random access multiphoton microscopy for functional imaging of neuronal activity. Nat. Neurosci. 11, 713-720 (2008).
Regmi, R., Mohan, K. & Mondal, P. P. High resolution light-sheet based high-throughput imaging cytometry system enables visualization of intra-cellular organelles. AIP Adv. 4, (2014).
Reilly, L. P. O., Luke, C. J., Perlmutter, D. H., Silverman, G. A. & Pak, S. C. C. elegans in high-throughput drug discovery. Adv Drug Deliv Rev 247-253 (2014). doi:10.1016/j.addr.2013.12.001.C.
Reynaud, E. G., Peychl, J., Huisken, J., & Tomancak, P. (2015). Guide to light-sheet microscopy for adventurous biologists. Nature methods, 12(1), 30-34.
Romer, G. R. B. E. & Bechtold, P. Electro-optic and acousto-optic laser beam scanners. Phys. Procedia 56, 29-39 (2014).
Roorda, R. D., Hohl, T. M., Toledo-Crow, R. & Miesenböck, G. Video-rate nonlinear microscopy of neuronal membrane dynamics with genetically encoded probes. J. Neurophysiol. 92, 609-21 (2004).
Rupprecht, et al. Optimizing and extending light-sculpting microscopy for fast functional imaging in neuroscience. Biomed. Opt. Express 6(2), 353 (2015).
Salomé, R. et al. Ultrafast random-access scanning in two-photon microscopy using acousto-optic deflectors. J. Neurosci. Methods 154, 161-174 (2006).
Schmitt, J. Optical Coherence Tomography (OCT): A Review. IEEE J. Sel. Top. Quantum Electron. 5(4), 1205(1999).
Schrödel, T., Prevedel, R., Aumayr, K., Zimmer, M. & Vaziri, A. Brain-wide 3D imaging of neuronal activity in Caenorhabditis elegans with sculpted light. Nat. Methods 10, 1013-1020 (2013).
Sirenko, O. et al. High-Content Assays for Characterizing the Viability and Morphology of 3D Cancer Spheroid Cultures. Assay Drug Dev. Technol. 13, 402-14 (2015).
Sjöback, R. et al. Absorption and fluorescence properties of fluorescein. Acta Part A Mol. Biomol. 51, 1-15 (1995).
Svoboda and R. Yasuda, "Principles of Two-Photon Excitation Microscopy and Its Applications to Neuroscience," Neuron 50(6), 823-839 (2006).
Tal, E., Oron, D. & Silberberg, Y. Improved depth resolution in video-rate line-scanning multiphoton microscopy using temporal focusing. Opt. Lett. 30, 1686 (2005).
Teich, M. C., Matsuo, K. & Saleh, B. E. A. Excess noise factors for conventional and superlattice avalanche photodiodes and photomultiplier tubes. IEEE J. Quantum Electron. 22, 1184-1193 (1986).
Theer, et al., Two-photon imaging to a depth of 1000 μm in living brains by use of a Ti:Al_2O_3 regenerative amplifier. Opt. Lett. 28(12), 1022 (2003).
Tomer, R. et al. SPED light sheet microscopy: fast mapping of biological system structure and function. Cell 163, 1796-1806 (2015).
Trivedi, V. et al. Dynamic structure and protein expression of the live embryonic heart captured by 2-photon light sheet microscopy and retrospective registration. Biomed. Opt. Express 6, 2056 (2015).
Truong, T. V, Supatto, W., Koos, D. S., Choi, J. M. & Fraser, S. E. Deep and fast live imaging with two-photon scanned light-sheet microscopy. Nat. Methods 8, 757-760 (2011).
Unger, M. A., Chou, H. P., Thorsen, T., Scherer, A. & Quake, S. R. Monolithic microfabricated valves and pumps by multilayer soft lithography. Science 288, 113-6 (2000).
Vanderlugt, A., & Bardos, A. M. (1992). Design relationships for acousto-optic scanning systems. Applied optics, 31(20), 4058-4068.
Visscher, K., Brackenhoff, G. J. & Visser, T. D. Fluorescence saturation in confocal microscopy. Journal of Microscopy 175, 162-165 (1994).
Vogel, et al. Mechanisms of femtosecond laser nanosurgery of cells and tissues. Appl. Phys. B 81(8), 1015-1047 (2005).

(56) References Cited

OTHER PUBLICATIONS

Weisenburger, S. and Sandoghdar, V. Light microscopy: an ongoing contemporary revolution, Contemp. Phys. 56(2), 123-143 (2015).
Winter and Shroff. Faster fluorescence microscopy: Advances in high speed biological imaging. Curr. Opin. Chem. Biol. 20(1), 46-53 (2014).
Wu and R. K. Y. Chan, "A fast fluorescence imaging flow cytometer for phytoplankton analysis.," Opt. Express 21(20), 23921-6 (2013).
Wu, J., Li, J. & Chan, R. K. Y. A light sheet based high throughput 3D-imaging flow cytometer for phytoplankton analysis. Opt. Express 21, 14474-80 (2013).
Xu et al., "Measurement of two-photon excitation cross sections of molecular fluorophores with data from 690 to 1050 nm," J. Opt. Soc. Am. B 13(3), 481 (1996).
Xu, et al., Determination of absolute two-photon excitation cross sections by in situ second-order autocorrelation. Opt. Lett. 20(23), 2372 (1995).
Yang et al. Genetically Encoded Voltage Indicators: Opportunities and Challenges. J. Neurosci. 36(39), 9977-9989 (2016).
Yang, W. et al. Simultaneous Multi-plane Imaging of Neural Circuits. Neuron 89, 284, (2016).
Mh, J.-N. et al. Temporal focusing-based multiphoton excitation microscopy via digital micromirror device. Opt. Lett. 39, 3134-7 (2014).
Young, E. C. Barbano, N. Worts, J. J. Field, C. Hoy, K. A. Wernsing, R. A. Bartels, and J. Squier, "Spatial Frequency Modulated Imaging (SPIFI) with amplitude or phase grating from a spatial light modulator," 100692P (2017).
Zhang, et al. Imaging with Raman Spectroscopy. Curr Pharm Biotechnol. 11(6), 654-661 (2010).
Zhi, P., Chia, C. & Gleeson, P. A. Imaging and Quantitation Techniques for Tracking Cargo along Endosome-to-Golgi Transport Pathways. Cells 2, 105-123 (2013).
Zhu, G., van Howe, J., Durst, M., Zipfel, W. & Xu, C. Simultaneous spatial and temporal focusing of femtosecond pulses. Opt. Express 13, 2153-9 (2005).
Zipfel, et al., Nonlinear magic: multiphoton microscopy in the biosciences. Nat. Biotechnol. 21(11), 1369-1377 (2003).
Zong, W. et al. "Large-field high-resolution two-photon digital scanned light-sheet microscopy." Cell Res. 25, 254-257 (2015).
International Preliminary Report on Patentability issued for International Application No. PCT/US2019/031763, dated Nov. 19, 2020.

\* cited by examiner

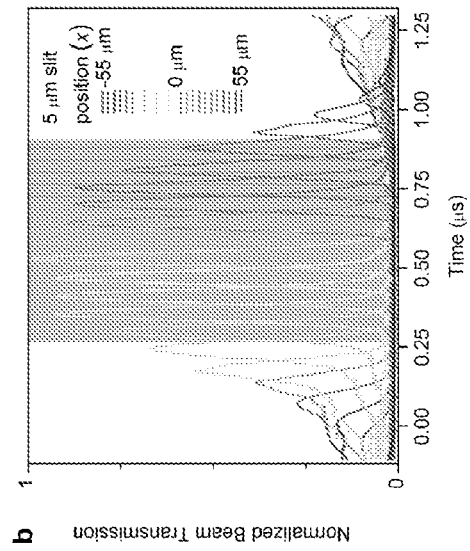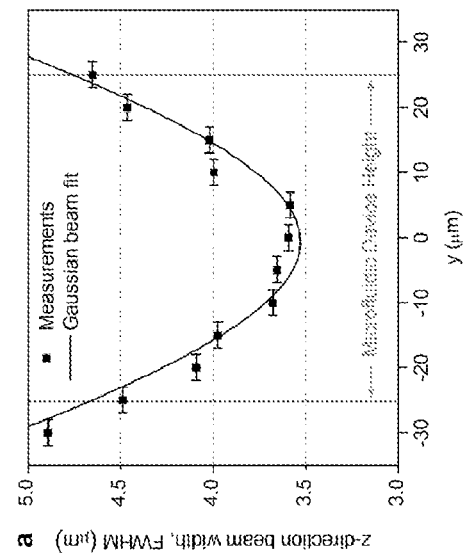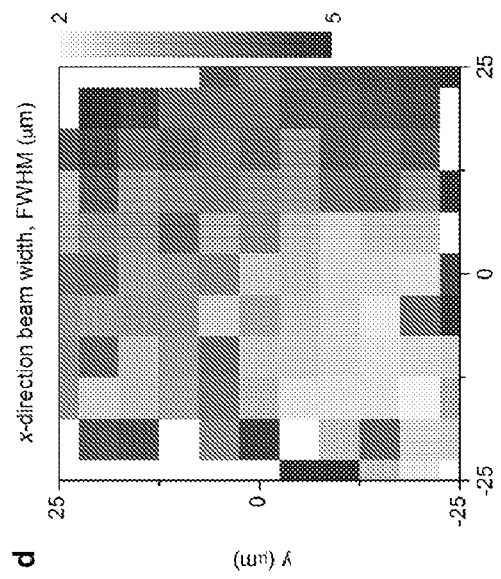
Fig. 7A
Fig. 7B
Fig. 7C
Fig. 7D

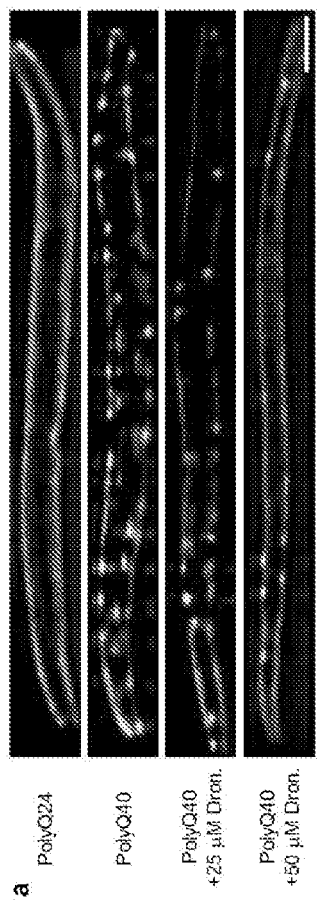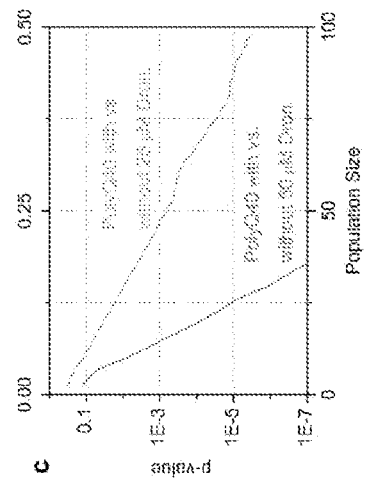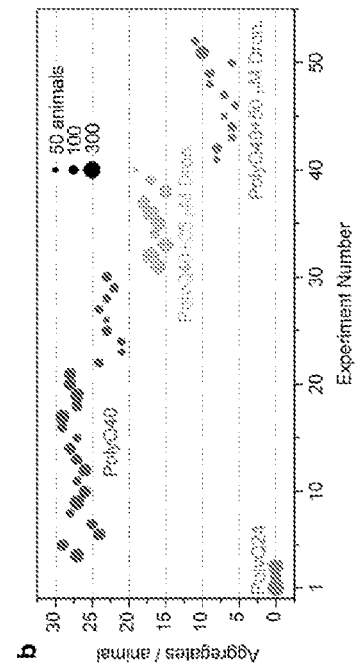
Fig. 16A
Fig. 16B
Fig. 16C

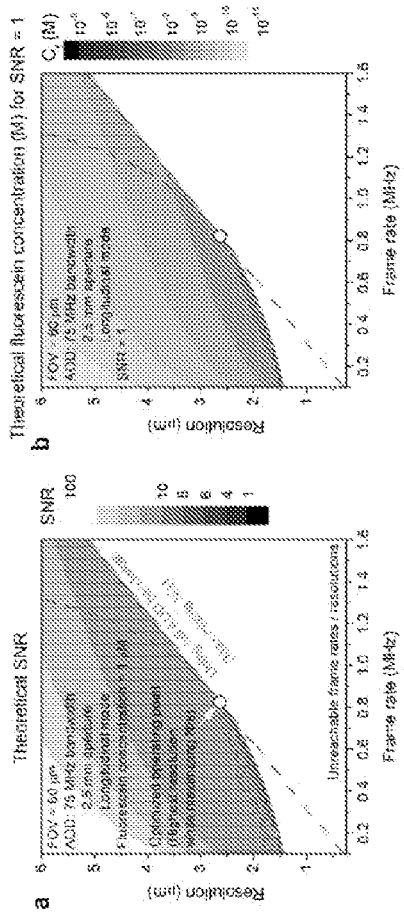
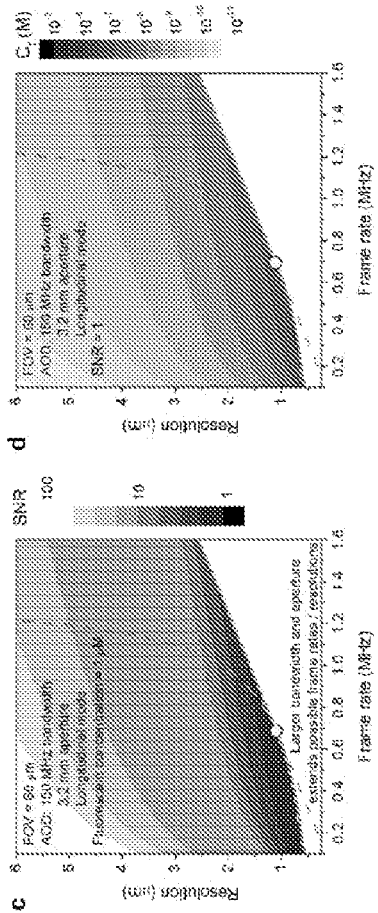
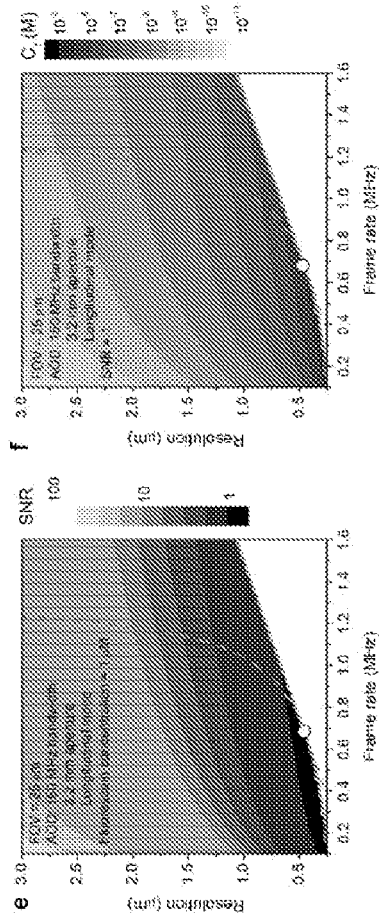
Fig. 20A Fig. 20B Fig. 20C Fig. 20D Fig. 20E Fig. 20F

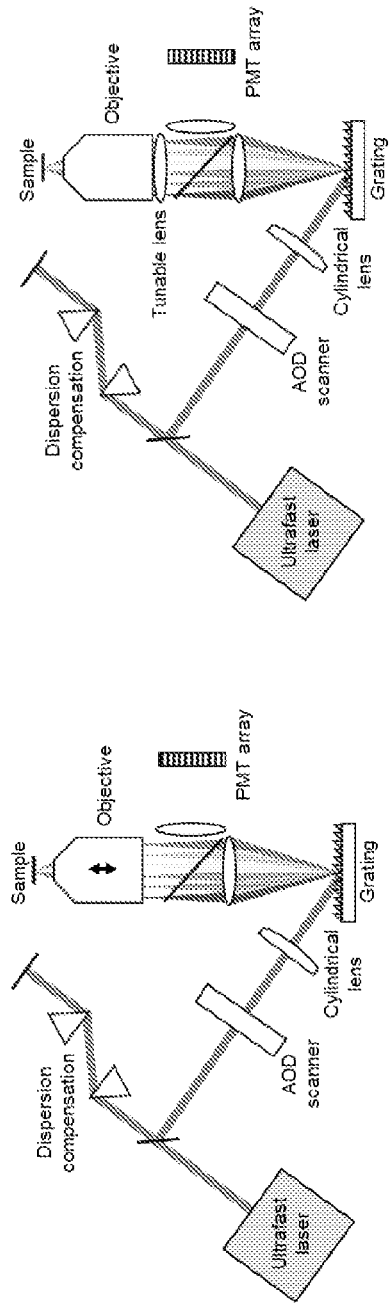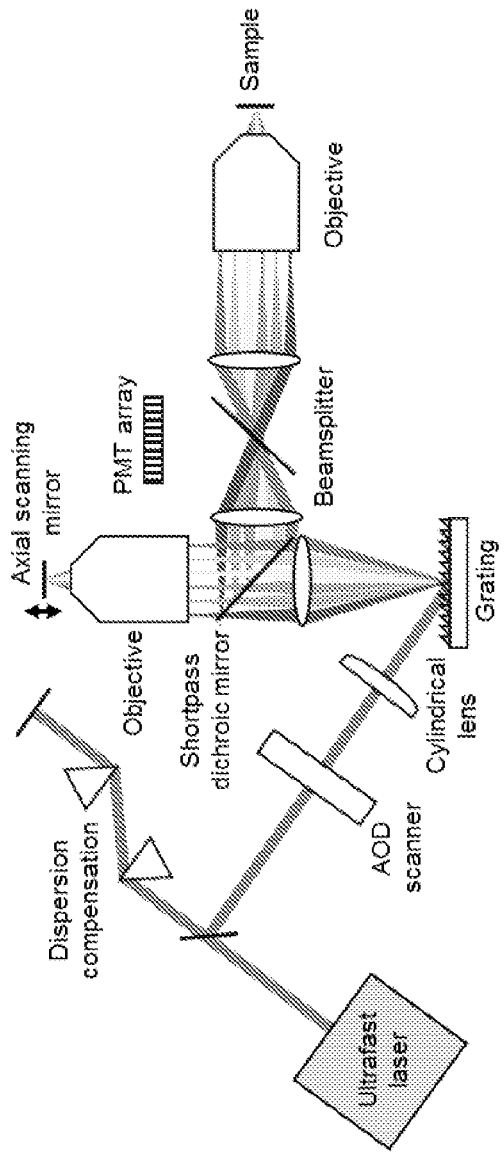
Fig. 22A
Fig. 22B
Fig. 22C

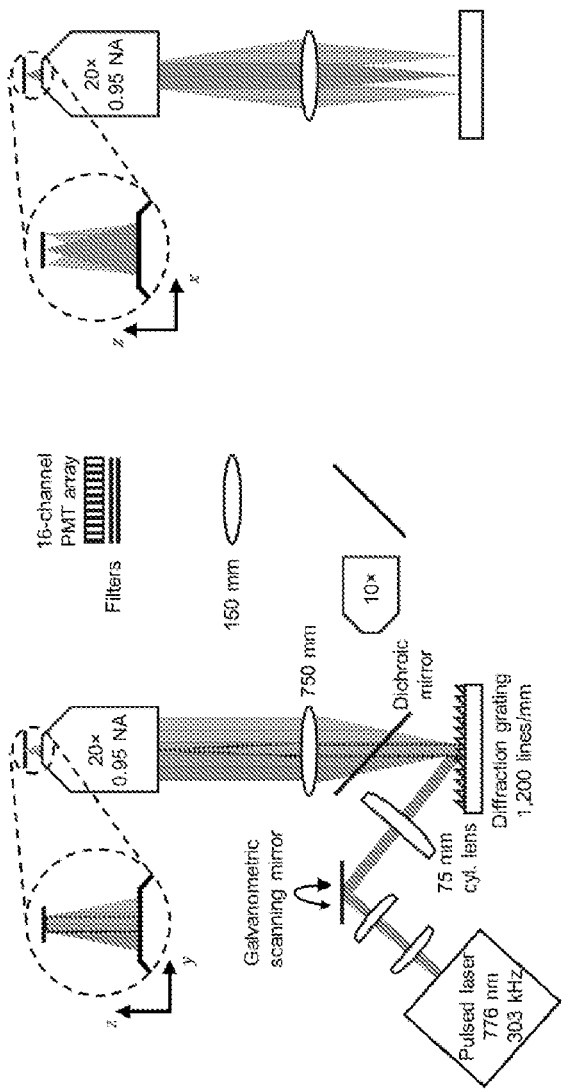
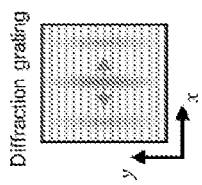
Fig. 24A
Fig. 24B
Fig. 24C

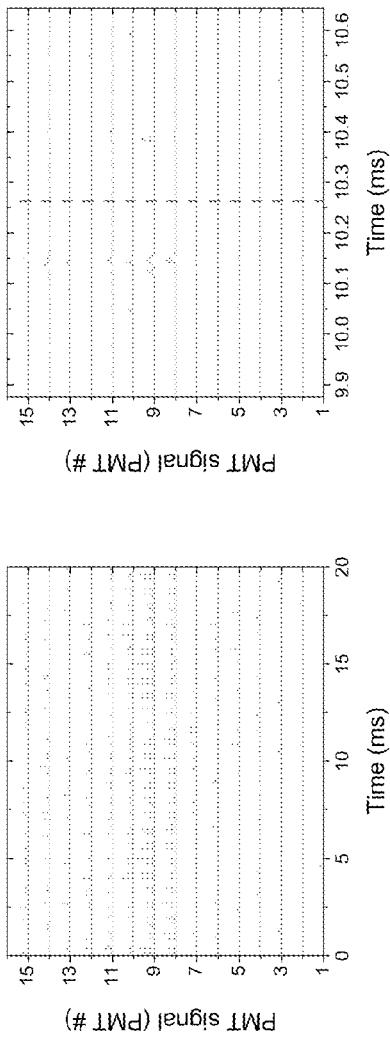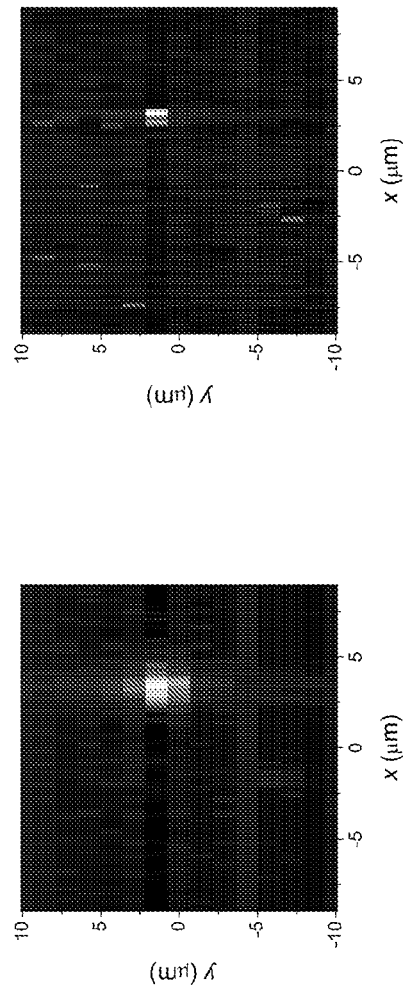
Fig. 29a  Fig. 29b  Fig. 29c  Fig. 29d

LINE EXCITATION ARRAY DETECTION MICROSCOPY

CROSS-REFERENCE TO RELATED APPLICATION

This application claims the benefit of U.S. Provisional Application No. 62/669,573, entitled "LINE EXCITATION ARRAY DETECTION MICROSCOPY," filed May 10, 2018, the disclosure of which is incorporated herein by reference in its entirety.

STATEMENT REGARDING FEDERALLY SPONSORED RESEARCH

This invention was made with government support under Grant No. R01 AG041135, awarded by the National Institutes of Health. The government has certain rights in the invention.

BACKGROUND

Today's most demanding fluorescence imaging applications require high speeds and three-dimensional (3D) resolution. For example, understanding how the brain processes information requires imaging neurons in 3D circuits communicating through action potentials at millisecond timescales using newly developed fast voltage indicators[1,2]. High-throughput screening of small model organisms, such as *C. elegans*, *D. melanogaster*, and *Danio rerio*, requires whole-body imaging to detect phenotypic changes and high speeds to screen for mutants, molecular pathways, genes, or extensive drug libraries[3-5]. Similarly, high-content assays of 3D spheroids, cultures of cells mimicking tissues and disease pathologies, require fast, sub-cellular resolution imaging to detect changes throughout the spheroid in response to drug compounds without disrupting the spheroid structure[6]. Even higher resolution is needed for cellular cytometry to image organelles such as mitochondria[7], or to monitor membrane trafficking of labeled cargo[8].

Current high-speed three-dimensional (3D) fluorescence imaging techniques are limited by the acquisition rate and sensitivity tradeoffs of detectors and the speed of laser beam scanners. Wide-field and light-sheet fluorescence microscopies have the advantage of full-frame excitation and detection using a camera. However, they have either high sensitivity and slow readouts or low sensitivity and require relatively long dwell times to detect weak signals, thereby limiting imaging frame rates to kilohertz (kHz), which are too slow to capture dynamic action potential transients or cause motion blur in cytometry[9-19]. Photomultiplier tubes (PMTs) have higher sensitivities, but their single element nature necessitates fast point-by-point scanning techniques to capture full frames and volumes. Widely used inertial galvanometric and resonant mirrors are limited to kHz and 10's of kHz line-scan rates, respectively, restricting volumetric rates to 10's of Hz[20]. Inertia-free acousto-optic deflectors (AODs) have the potential for line-scan rates of nearly 1 MHz when used in longitudinal mode and driven by a chirped signal[21,22]. However, for in-depth biological studies, only slower shear AODs have been used in chirped mode for high-resolution imaging[23-25], or dwell mode for random-access imaging[26-29], limiting line-scan rates to tens (10's) of kHz and frame rates to 1 kHz. Methods to overcome slow scanners include eliminating scanning along one axis altogether through frequency encoding of spatial information, but are limited by the speed of modulators and the need to collect multiple oscillation cycles, and can suffer from a reduced dynamic range per pixel and increased shot noise[30-32]. Parallelized imaging with multiple excitation points and multi-element PMTs overcomes the problem of serial acquisition, but has been implemented using discrete excitation points that still require scanning along each imaging axis[33-35]. Overall, current imaging methods are limited to kHz frame rates and 10's of Hz volumetric rates because of insensitive detectors or slow scanners. It is with respect to these and other considerations that the various embodiments described below are presented.

SUMMARY

In some aspects, the present disclosure relates to systems and methods for line excitation array detection (LEAD) microscopy.

One aspect of the present disclosure relates to a system for imaging a subject of interest. In one embodiment, the system includes an optical beam source configured to provide an excitation beam, and one or more beam scanners configured for line scanning of the excitation beam across the subject. The system also includes one or more linear arrays of optical detectors configured for parallel detection of the optical signals from the different segments of the subject in response to the excitation beam.

In one embodiment, the beam scanners include one or more scanning mirrors coupled to the optical beam source. To perform the line scanning by the scanning mirrors, the scanning mirrors can be moved using electric motors, galvanometers, piezoelectric actuators, magnetostrictive actuators, and/or MEMS.

In one embodiment, the beam scanners include an acousto-optic deflector (AOD) coupled to the optical beam source. In one embodiment, the AOD is comprised of a crystal in a longitudinal mode. In one embodiment, the AOD operates in a chirped mode or a dwell mode. In one embodiment, the AOD is configured to produce a scan rate of up to about 10 MHz. In one embodiment, the AOD is comprised of a crystal in a shear mode. In one embodiment, the AOD is comprised of $TeO_2$, $PbMoO_4$, Quartz, or Ge crystals.

In one embodiment, the beam scanners comprise an electro-optic deflector (EOD) coupled to the optical beam source. In one embodiment, the beam scanners are configured for random access scanning.

In one embodiment, the linear arrays of optical detectors comprise a linear array of photomultiplier tubes (PMTs). The linear array of optical detectors can comprise a silicon photomultiplier (SiPM) array, avalanche photodiode array, a linescan camera with an intensifier, and/or a linescan camera without an intensifier. In one embodiment, each of the optical detectors collects light from a different respective segment of the excitation beam.

In one embodiment, the system also comprises a parallel data acquisition system coupled to the linear arrays of optical detectors, and an image reconstruction system coupled to one or more multi-channel data acquisition devices, configured to generate three-dimensional images of the subject based on the detected optical signals. In one embodiment, the one or more multi-channel data acquisition devices includes a plurality of multi-channel data acquisition devices that operate in different computers that are synchronized to collect data from the one or more linear arrays of optical detectors. In one embodiment, at least one of the linear arrays of optical detectors is arranged at angle in between 10° to 170° to the scanning direction.

In one embodiment, the linear arrays of optical detectors are configured for detecting signal from a complete or partial excitation beam line as the beam scans and such that a full image frame is generated for each scan cycle. In one embodiment, the linear arrays of optical detectors are configured to measure fluorescence optical signals from the subject of interest, in response to excitation from the excitation beam.

In one embodiment, the system is configured for laser speckle contrast imaging, volumetric phosphorescence lifetime microscopy, or high-speed particle image velocimetry (PIV). In one embodiment, the system is configured for flow cytometry wherein the subject is in motion through the system during the scanning.

In one embodiment, the subject comprises one or more cells or three-dimensional tissue constructs. In one embodiment, the subject is a complete living organism. In one embodiment, the subject is a non-biological object.

In one embodiment, the system also comprises an optical feedback system configured to monitor location of the excitation beam during scanning, wherein the optical feedback system comprises an optical detector and slit configured to monitor location of a second order diffraction beam or calibration beam for calibrating location of the excitation beam.

In one embodiment, the system is configured for nonlinear microscopy. In one embodiment, the is configured for two-photon or multi-photon fluorescence or auto-fluorescence. In one embodiment, the system is configured for second or third harmonic generation microscopy.

In one embodiment, the system is configured for imaging of at least part of the brain of the subject. In one embodiment, the system is configured for in vivo imaging of at least part of the brain of the subject. In one embodiment, the system is configured for imaging at least part of the heart of the subject and the imaging comprises imaging an active function of the heart of the subject.

In one embodiment, the system is configured to excite a plane that is from −80° to 80° at an angle to the optical axis and imaged through a single objective. In one embodiment, the system also includes a simultaneous spatial and temporal focusing (SSTF) system for increasing axial resolution, wherein the SSFT system comprises a diffraction grating, a grism, or a digital micromirror device (DMD) configured as a grating.

In one embodiment, the system also comprises an axial scanning system. In one embodiment, the axial scanning system comprises at least one of: a piezoelectric stage to which an objective is mounted, moving along the optical axis; a tunable lens before the objective; remote focusing in which an axially scanned mirror is imaged onto the sample; and a spatial light modulator configured as a reflective lens before the objective.

In one embodiment, the one or more linear arrays of optical detectors are combined with spectral filters and configured for multi-color imaging.

In one embodiment, the system is further configured to correct optical aberrations using customized objectives or an objective-device immersion system or adaptive optics or a prism below the microfluidic device, in the path of the excitation beam and collection signal or a tilted lens or tilted piece of glass in a conjugate imaging plane of the imaging path.

In one embodiment, the system is further configured to generate an excitation beam in the configuration of a Gaussian beam or Bessel beam or Airy beam.

In one embodiment, the system is further configured to shape the laser excitation beam entering the AOD aperture to have a width equal to or less than the aperture width.

Another aspect of the present disclosure relates to a method for imaging of a subject of interest. In one embodiment, the method comprises: providing an excitation beam from an optical beam source; line scanning the excitation beam across the subject, by using one or more beam scanners; and performing, using one or more linear arrays of optical detectors, parallel detection of optical signals from the different segments of the subject in response to the excitation beam.

In one embodiment, the method also comprises: providing a parallel data acquisition system coupled to the one or more linear arrays of optical detectors and an image reconstruction system coupled one or more multi-channel data acquisition devices; and generating, using the parallel data acquisition system and image reconstruction system, three-dimensional images of the subject based on the detected optical signals.

In one embodiment, the linear arrays of optical detectors are arranged at an angle in between 10° to 170° to the scanning direction. In one embodiment, the method comprises detecting, by the linear arrays of optical detectors, one or more signals from a complete or partial excitation beam line as the beam scans and such that a full image frame is generated for each scan cycle. In one embodiment, the method comprises measuring, by the linear arrays of optical detectors, fluorescence optical signals from the subject in response to excitation from the excitation beam.

In one embodiment, the method comprises performing flow cytometry wherein the subject is in motion during the scanning. In one embodiment, the subject comprises one or more cells or three-dimensional tissue constructs.

In one embodiment, the subject is a complete living organism. In one embodiment, the subject is a non-biological object.

In one embodiment, the method also comprises: providing an optical feedback system comprising an optical detector and slit configured to monitor location of a second order diffraction beam or calibration beam for calibrating location of the excitation beam; and monitoring, using the optical feedback system, location of the excitation beam during scanning.

In one embodiment, the method comprises performing nonlinear microscopy. In one embodiment, the method comprises performing two-photon or multi-photon fluorescence microscopy. In one embodiment, the method comprises performing second or third harmonic generation microscopy.

In one embodiment, the method comprises imaging at least a part of the brain of the subject. In one embodiment, the method comprises performing in vivo imaging of at least part of the brain of the subject. In one embodiment, the method comprises imaging an active function of the heart of the subject.

In one embodiment, the method comprises exciting a plane that is from −80° to 80° at an angle to the optical axis and imaging through a single objective. In one embodiment, the method comprises providing a simultaneous spatial and temporal focusing (SSTF) system for increasing axial resolution, wherein the SSFT system comprises a diffraction grating, a grism, or a digital micromirror device (DMD) configured as a grating. In one embodiment, the method comprises providing an axial scanning system that comprises at least one of: a piezoelectric stage to which an objective is mounted, moving along the optical axis; a tunable lens before the objective; remote focusing in which an axially scanned mirror is imaged onto the subject; and a spatial light modulator configured as a reflective lens before the objective.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIGS. 7A-D illustrate aspects of a laser-beam while scanning, according to an embodiment of the present disclosure.

FIG. 10A schematically illustrates a microfluidic device according to an embodiment of the present disclosure, while

FIG. 15B is from LEAD microscopy.

FIGS. 16A-C illustrate LEAD microscopy results from imaging polyglutamine (polyQ) mediated aggregation model C. elegans treated with the compound dronedarone.

FIGS. 20A-F are graphs of theoretical SNR and detection limits of 1 µM fluorescein as a function of desired resolution and frame rate, for two different FOVs and AODs.

FIGS. 22A-C schematically depict LEAD nonlinear microscopy systems with axial scanning, according to some embodiments of the present disclosure.

FIGS. 24A-C schematically depict a two-photon LEAD microscope with scanning mirrors for brain imaging according to some embodiments of the present disclosure.

FIGS. 29A-D are graphs of raw data and images from imaging a 0.5 µm diameter fluorescent bead according to some embodiments of the present disclosure.

DETAILED DESCRIPTION

Figure 1:
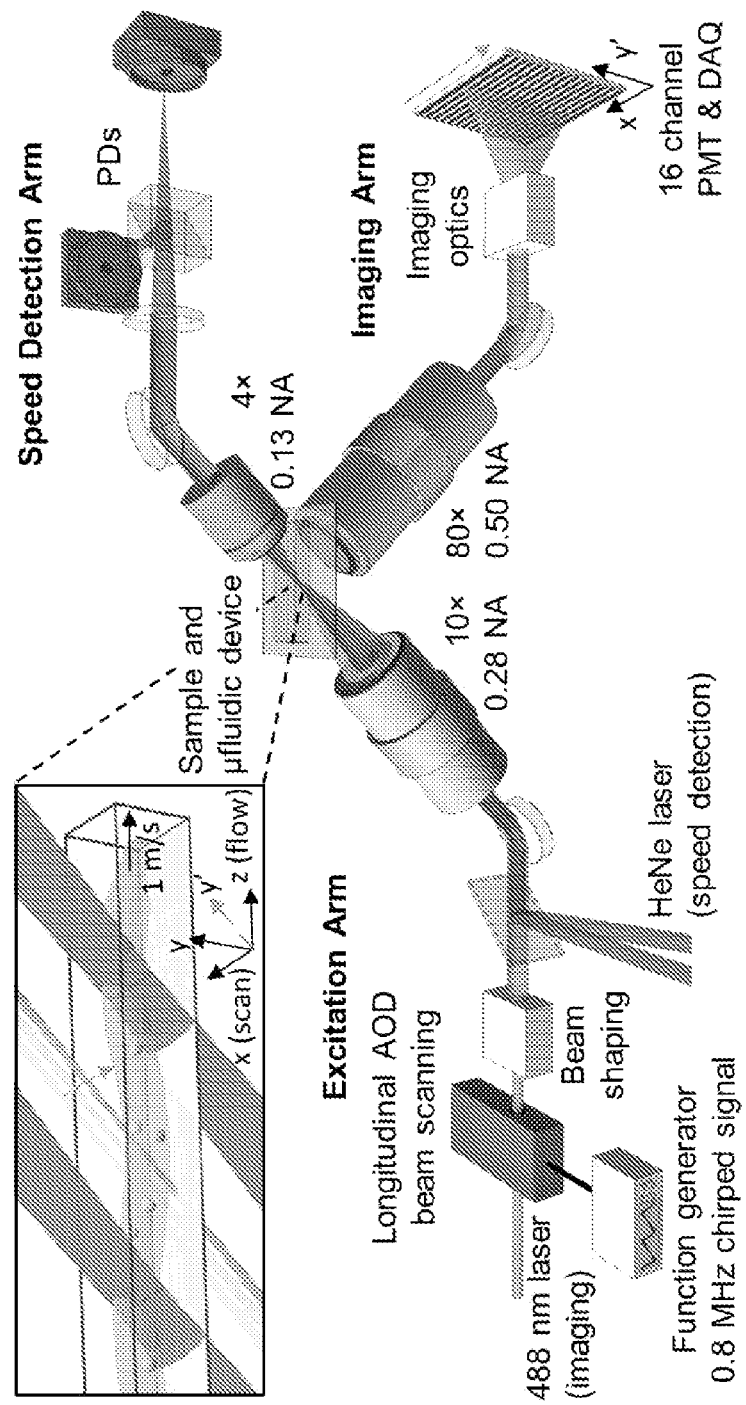
FIG. 1 schematically depicts a LEAD system according to an embodiment of the present disclosure.

Some aspects of the present disclosure relate to LEAD microscopy. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the"

include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value. As used herein, "about" means within 20 percent or closer of a given value or range.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference.

As discussed herein, a "subject" or "patient" may be any applicable human, animal, or other organism, living or dead, or other biological or molecular structure or chemical environment, and may relate to particular areas which may be referred to herein as an "area of interest", "target area", or "target area of interest". It should be recognized that while subjects described in some implementations of various aspects of the present disclosure described herein are biological or chemical in nature, some aspects of the present disclosure may be implemented to examine a variety of non-living subjects (which may be referred to as "object" or "objects").

One or more data acquisition or data collection steps as described herein in accordance with one or more embodiments may include acquiring, collecting, receiving, or otherwise obtaining data such as imaging data corresponding to a subject. By way of example, data acquisition or collection may include acquiring data via a data acquisition device, receiving data from an on-site or off-site data acquisition device or from another data collection, storage, or processing device.

The following description provides a further discussion of certain aspects of the present disclosure in accordance with example embodiments. The discussion of some example implementations also refers to corresponding results which may include experimental data. Experimental data presented herein is intended for the purposes of illustration and should not be construed as limiting the scope of the present disclosure in any way or excluding any alternative or additional embodiments.

Throughout the disclosure, references are made in superscripts to the documents in Reference List A below. For example, document 23 from Reference List A may be identified by number in a superscript[23]. Also, references are made in brackets to the documents in Reference List B below. For example, document 23 may be identified from Reference List B by placing the number twenty three in brackets [23].

A discussion of some aspects and embodiments of the present disclosure that relate to LEAD microscopy will now be described along with the corresponding figures.

Line excitation array detection (which the inventors may refer to as "LEAD") microscopy as disclosed herein provides for volumetric imaging capable of nearly 1 million frames per second. Any limitations of imaging speed and photon detection are overcome by an ultrafast scanning method using a longitudinal acousto-optic deflector (AOD) in chirped mode and a sensitive, parallelized detection scheme using a linear PMT array. Scanning methods that may be utilized in various other embodiments can use mirrors, polygonal mirrors, MEMS mirrors, shear AODs, AODs with a chirped frequency signal or in dwell mode, and/or electro-optic deflectors (EODs). Also, while a linear PMT array is used in some embodiments, other sensitive detector arrays may be utilized, such as silicon photomultiplier (SiPM) arrays, avalanche photodiode arrays, and/or linescan cameras.

FIG. 1 graphically depicts an imaging system for LEAD microscopy according to an embodiment of the present disclosure. In particular, the system shown is implemented as a 3D whole animal flow cytometer. A longitudinal $TeO_2$ AOD driven with a chirped frequency scans the laser excitation beam across an angled plane on the sample at 0.8 megahertz (MHz). The excited plane is imaged onto 14 channels of a 16-channel photomultiplier tube (PMT) array, capturing a full frame each scan cycle. A microfluidic device delivers populations of 100's of C. elegans at ~1 m/s through the excitation region (Inset), providing the third dimension for volumetric imaging. Two light sheets generated by a HeNe laser and two photodiodes (PDs) measure animal velocity through the imaging region.

The AOD scans an axially extended excitation beam across a full cross-section of a sample at 0.8 MHz, effectively forming a light sheet. The linear array of PMTs images the line as it scans, with each element detecting a section of the line, thereby generating an entire frame in a single scan of the AOD.

Figure 2:
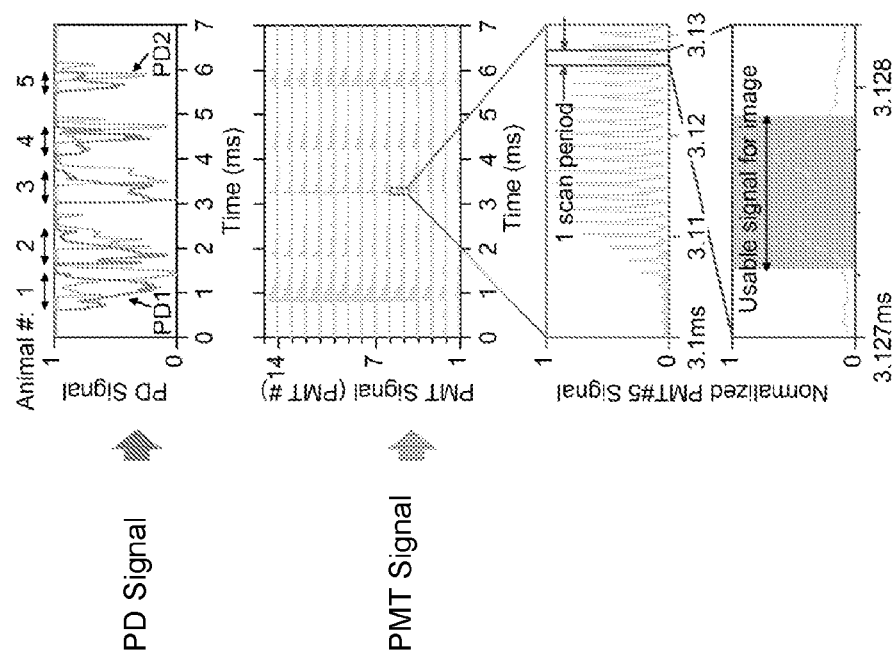
FIG. 2 depicts graphs of exemplary photodiode (PD) signals and photomultiplier tube (PMT) signals from the LEAD system of FIG. 1.

FIG. 2 depicts graphs of exemplary PD signals and PMT signals from the LEAD system of FIG. 1. Specifically, FIG. 2 depicts representative PD and PMT signals from five animals imaged within 7 milliseconds (ms). A drop in transmission of the PD signals indicates the presence of an animal, and the time delay between the two PD signals indicates the velocity. The fluorescence signals measured by the 14 PMT channels are used to generate volumetric images. (Inset 1) The fluorescence signal from the head of an animal is shown for a single PMT over several scan periods, showing a signal to noise ratio (SNR)>500. (Inset 2) The signal from fluorescent features during a single 1.25 microsecond (µs) scan cycle. The gray region indicates the usable imaging period when the upchirped AOD signal scans the beam linearly across the sample.

When combined with a moving specimen or slower secondary scanner, we can acquire full volumes can be acquired. Using a tellurium dioxide (TeO$_2$) AOD in longitudinal configuration increases the acoustic velocity by seven times (7×) over shear configuration, improving the line-scan rate, while operating in chirped mode enables continuous scanning without waiting for the laser beam to settle.

Figure 3:
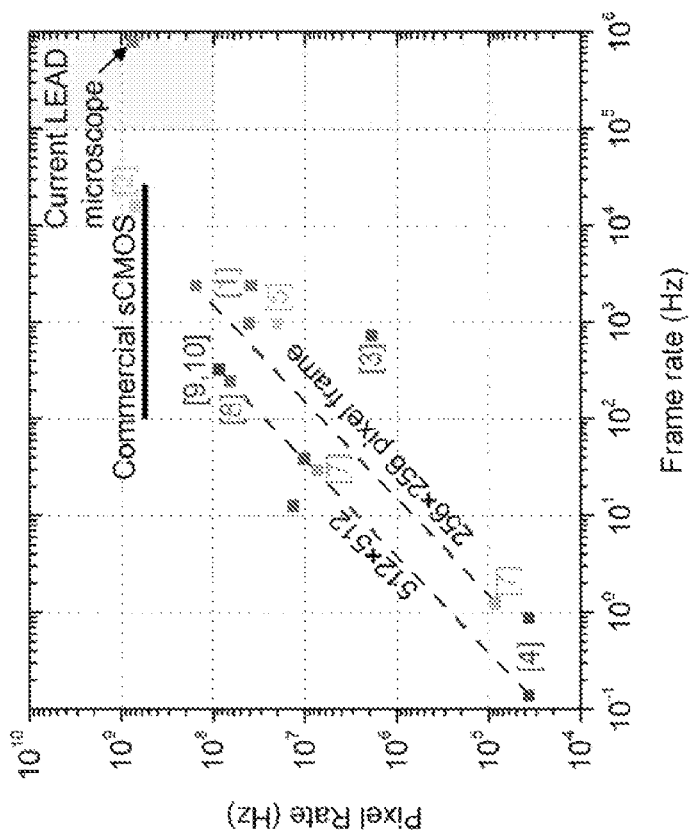
FIG. 3 depicts a graph of exemplary pixel rates and framerates of LEAD microscopy as compared to other imaging techniques.

The optimized AOD scanning method in accordance with certain embodiments of the present disclosure allows the beam to scan over an entire field of view (FOV) in the same time it takes random-access AOD imaging to switch between two points. The parallel detection scheme differs from previous multi-element PMT methods by imaging the full excitation line and capturing a full frame in a single scan period, eliminating the need for scanning along the excitation axis. Compared to camera-based light-sheet microscopy, LEAD microscopy provides superior sensitivity, allowing faster scanning and higher imaging speeds. The name "line excitation array detection" corresponds to two aspects of LEAD microscopy, namely ultrafast line-scanning and sensitive array detection, enabling LEAD microscopy to reach >100× higher frame rates than any other fluorescence imaging system without compromising sensitivity and total pixel rate. This comparison is illustrated in FIG. 3.

The state-of-the-art fluorescence imaging technologies are limited to 2.4 kHz frame rate using a sCMOS camera[19], and 16 kHz frame rate using a PMT with multiplexing [67], while our current LEAD microscope provides 0.8 MHz frame rate and the highest pixel rate. LEAD systems can potentially image larger field of views with larger frame sizes than the current system, and reach 10 GHz pixel rates with a 256 element PMT. The highlighted region in FIG. 3 is the LEAD microscopy regime.

The previous fastest imaging system uses multiplexing, a single PMT, and an 8 kHz resonant mirror to reach 16 kHz frame rates and 702 MHz pixel rates with 190×231 pixel frames [67]. However, since all the pixels along one dimension are captured simultaneously using a single PMT, the dynamic range per pixel is reduced, and all the pixels share increased shot noise, creating a theoretical limit to their maximum achievable frame-rates. On the other hand, LEAD microscopy maintains high dynamic range and low noise per pixel. The frame sizes in Mikami et al. [67] are larger than the current LEAD system, making it more suitable for high resolution or large FOV imaging, albeit at lower frame-rates. LEAD systems can have frames with more pixels using higher bandwidth or larger aperture AODs and using PMTs with more elements.

Compared to the fastest camera-based imaging method (SCAPE) of Bouchard et al.[19], LEAD has smaller frames but much higher frame rate. Current sCMOS cameras are limited in their maximum frame rate, even when using a small region of interest, as seen by the commercial sCMOS range in the figure. Faster frame rates would require new cameras with faster readout rates. On the other hand, LEAD can continually improve on the frame size while maintaining high frame rates.

Figure 4:
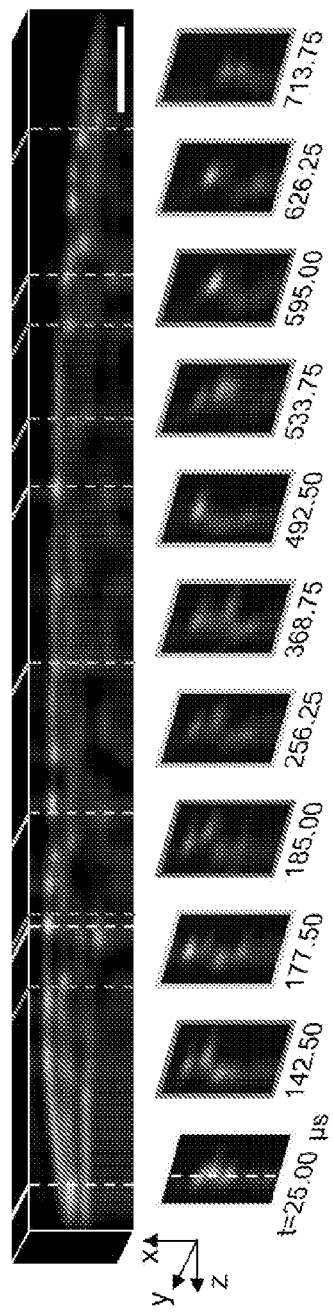
FIG. 4 depicts an exemplary 3D reconstruction of flow cytometry results of a Caenorhabditis elegans (C. elegans) nematode using LEAD microscopy according to an embodiment of the present disclosure.

The results of LEAD microscopy as a flow cytometer for blur-free, 3D fluorescence imaging of C. elegans moving at speeds over 1 m/s, capturing full volumes in 1 ms, 1,000× faster than the currently available 3D flow cytometers for large cells and whole animals[10,13] are shown in FIG. 4.

FIG. 4 depicts a 3D reconstruction of a polyQ40 strain C. elegans moving at an average velocity 0.89 m/s imaged in 0.79 ms. The volumetric image consists of 631 x-z frames captured every 1.25 µs, with each PMT element recording an x-y plane (PMT #7 is shown). The scale bar=50 µm in the figure.

C. elegans shares 60-70% genetic homology with humans[3], with many models recapitulating human disease phenotypes. Their system-level responses to drug treatment and amenability to manipulation with microfluidic devices make C. elegans ideal for high-content screening, providing faster and more efficient candidate selection compared to cell-based assays while maintaining low costs[5]. The inventors performed a phenotypic screening of thousands of polyglutamine-mediated protein-aggregation (polyQ) model C. elegans[36], and confirmed findings that the compound dronedarone can reduce aggregation with a dose response[37]. The whole animal flow cytometer using the LEAD system can provide the potential to screen a 10,000 compound drug library in under a day when combined with fast population delivery microfluidic systems[38].

Besides cytometry, the LEAD system shown in FIG. 1 may also be used to image mouse brain slices with the sensitivity to resolve single, 3D-distributed neurons and at speeds at which dynamic brain response can be observed. In addition, the LEAD system may be adapted for time-lapse imaging (e.g., using two-photon imaging). For example, a whole zebrafish brain with a 600×800×200 µm$^3$ volume (corresponding to 359×256×200 voxels with 3-4 µm lateral resolution) or a mammalian brain region with 1,000's of neurons can potentially be imaged at kHz volumetric rates.

Figure 5:
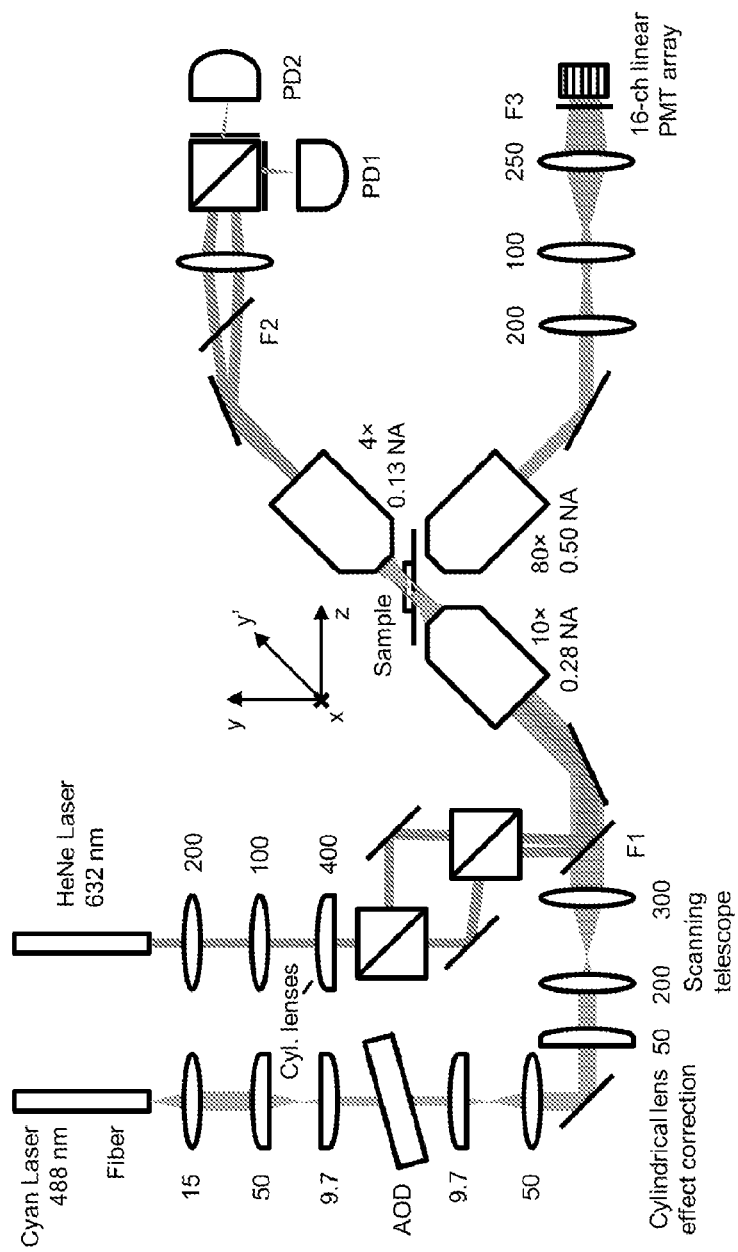
FIG. 5 depicts a detailed optical setup of a LEAD system according to an embodiment of the present disclosure.

FIG. 5 graphically depicts a detailed optical setup of a LEAD system according to an embodiment of the present disclosure. The LEAD fluorescence cytometer consists of four primary parts: 1) an excitation arm including the optics, AOD, and control systems required for scanning, 2) an imaging arm including the linear PMT array and a high-speed parallel data acquisition system for detection, 3) a microfluidic device for delivery of C. elegans through the imaging region, and 4) a speed detection arm for measuring animal velocity.

As shown in FIG. 5, a cyan excitation laser is collimated by an aspheric lens (all lens focal lengths in mm) and shaped by a cylindrical telescope to fill the 2.5×0.45 mm$^2$ aperture of the longitudinal TeO$_2$ AOD. In the non-scan direction, the effect of the cylindrical telescope is reversed by a cylindrical lens and spherical lens. In the scanning direction, the 50-mm spherical lens and a 50-mm cylindrical lens correct the cylindrical lens effect caused by driving the AOD by a chirped signal to obtain the tightest focus at the sample. A scanning telescope expands the scanning beam to the back aperture of the excitation objective. At the sample, the beam excites a ~70 µm line in the z'-direction and scans a 60 µm FOV in the x-direction. The excited plane is imaged by an orthogonal collection objective to a 16-channel linear PMT array after filtering by a bandpass filter (F3). The presence and speed of individual animals are detected using a second setup. A HeNe laser is shaped and split into two beams with angular offsets, and diverted towards the excitation objective by a low-pass beamsplitter (F1), forming two 5±1 µm thin light sheets separated by 210±1 µm at the sample. The two beams are trans-collected, filtered by a high-pass beamsplitter (F2), and detected individually by two iris and PD pairs (PD1, PD2).

The excitation arm includes the acousto-optic scanning system and focusing optics designed to excite a FOV covering the C. elegans cross-section at the fastest speed possible while maintaining cellular resolution. To this end, the inventors selected a longitudinal tellurium dioxide (TeO$_2$) AOD with a large usable bandwidth of 75 MHz (150-225 MHz) and a 2.5 mm aperture (Crystal Tech 3200-120). A sawtooth waveform at 0.8 MHz drives the AOD through its usable bandwidth to generate a linearly chirped acoustic wave in the AOD crystal, thus scanning the laser beam continuously without settling. In some implementations, the optimal 0.8 MHz scanning can provide the highest resolution possible while maximizing the rate of resolvable points achievable with the AOD[39,40]. Other embodiments may utilize a crystal other than $TeO_2$, for example $PbMoO_4$, Quartz, or Ge.

Figure 6A:
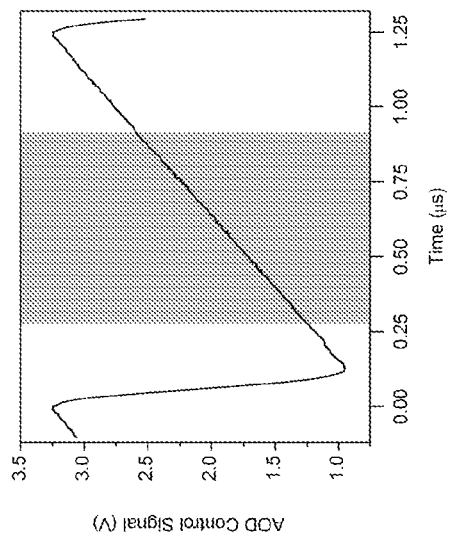
FIGS. 6A-D illustrate aspects of the operation of an acousto-optic deflector (AOD) according to an embodiment of the present disclosure.

FIGS. 6A-D illustrate aspects of the operation of the acousto-optic deflector (AOD) used in certain embodiments and implementations of the present disclosure. FIG. 6A is a graph of a function generator signal (i.e., the signal driving the AOD) with $V_0$=2.1 V, $\Delta V$=2.3 V, and t=1.25 μs (800 kHz), wherein the region of the scan used for imaging is highlighted in gray.

Figure 6B:
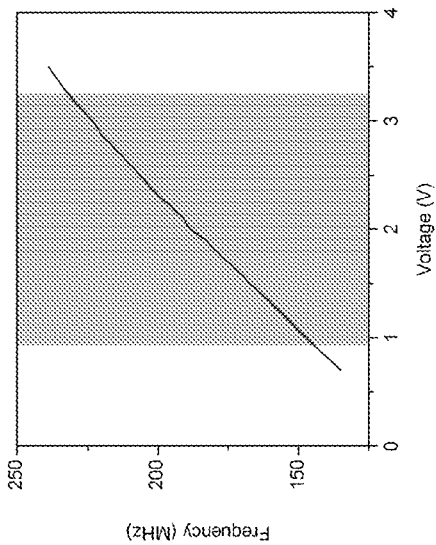

FIG. 6B is a graph of the AOD driver showing the conversion of the function generator signal into a linear frequency chirp that propagates in the AOD crystal. The AOD driver displays linear frequency-voltage response beyond its rated $f_0$=200 MHz and $\Delta f$=50 MHz. In practice, a $\Delta f$=75 MHz is used to generate more resolvable spots from the AOD.

Figure 6C:
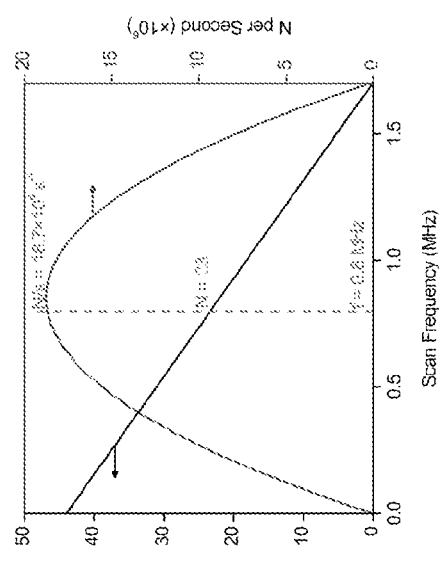

FIG. 6C is a graph showing the dependency of resolvable points on scan frequency. Observable in FIG. 6C, the AOD driven with a chirped frequency theoretically has a reduction in the number of resolvable points as scan frequency increases. The number of resolvable points per second reaches a maximum when the scan period is twice the response time of the AOD, i.e. when the beam is scanned back and forth as quickly as possible. The red line indicates a typical operating point.

Figure 6D:
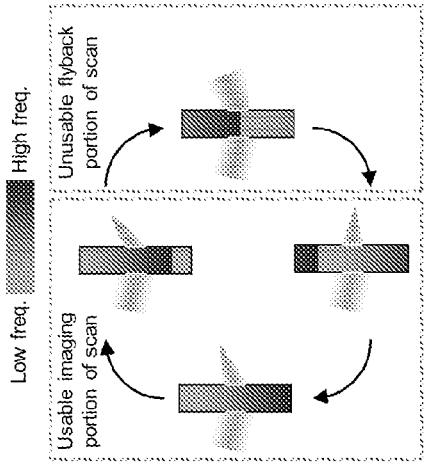

FIG. 6D illustrates the optical operation of the AOD when driven by the waveform in FIG. 6A. Two regimes are shown: the usable regime when the up-chirped portion of the acoustic wave propagates across the AOD aperture and produces a focused linear scan at the sample (left image), and the unusable regime when the down-chirped portion crosses the aperture, causing the beam to be defocused at the sample (right image).

At the sample, the beam forms a ~70 μm long (confocal length) excitation line in the y'-direction and scans a 60 μm FOV in the x-direction with ~23 resolvable points generated by the AOD. A 0.66 μs portion of the 1.25 μs scan period is used to form the images. During the remaining 0.59 μs of the scan period, the downchirped portion of the acoustic wave propagates across the AOD aperture and the excitation beam becomes distorted as it flies back to begin a new scan. Within the designed FOV of 60×50 μm² in the x-y plane, the beam maintains FWHM widths between 3.5-4.5 μm in the flow-direction (z) and 2.3-4.5 μm in the scan-direction (x), and a constant scan velocity of 89±1 m/s. The beam width was designed to match the resolution provided by the AOD in the scan-direction, which is defined by the FOV in the scan-direction and number of resolvable spots generated by the AOD. The confocal length of the beam also matches the FOV in the y'-direction, effectively forming a laser sheet with constant thickness, and eliminating the need for a Bessel beam.

FIGS. 7A-D illustrate aspects of the laser-beam shape during scanning. FIG. 7A is a graph showing the beam size in the flow-direction as measured by the knife edge test. As can be observed, the beam follows Gaussian beam propagation, with a FWHM between 3.5-4.5 μm where the imaging channel is located. Note, the error bars represent uncertainty in the position of the knife edge.

FIG. 7B is a graph of the laser beam's transmission through a 5 μm wide slit for different slit positions along the scanning axis, used to determine the full-width at half maximum (FWHM) in the scan-direction. As shown in FIG. 7B, the slit is translated in 5 μm increments in the scan direction from -55 μm to +55 μm. The usable imaging period is highlighted in gray. FIG. 7B illustrates the results for the slit positioned at the focal plane (z=0). The experiment was repeated for a range of y positions.

FIG. 7C is a graph showing the position and velocity of the peak intensity of the beam in FIG. 7B as a function of time. The speed is 89±1 m/s and is linear in the imaging region. FIG. 7D is a plot showing the beam FWHM in the scan direction as a function of x and y. The plot was computed by deconvolving transmission profiles (e.g., FIG. 7A) by a 5 μm slit.

Figure 8:
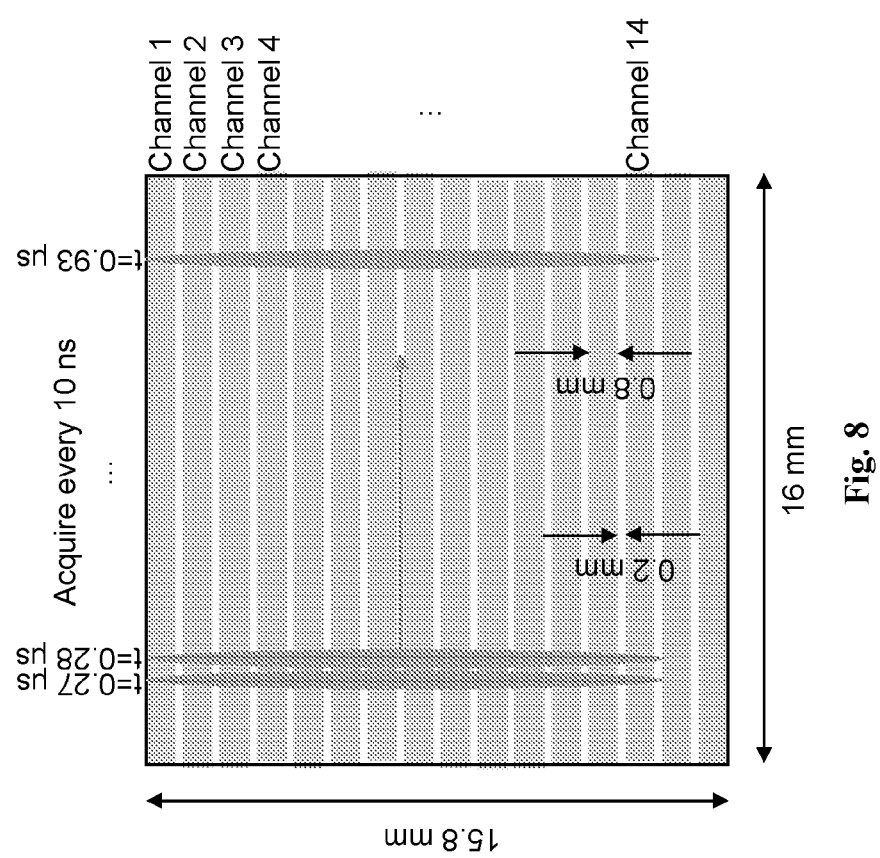
FIG. 8 illustrates details of imaging with a PMT array, according to an embodiment of the present disclosure.

The imaging arm images the 60×70 μm² skewed FOV (x-y' plane) onto 14 channels of the linear PMT array (Hamamatsu H10515B), with each element detecting 1 of 14 sections of the sample along the y'-direction (FIG. 8). The imaging optics include an 80×, 0.50 NA long working distance objective and a telescope for a combined magnification of 200×. Each PMT element has an active area of 16×0.8 mm², with 1 mm center-to-center separation between elements. In this scheme, the imaging resolution in the y-direction is defined by the demagnified separation between PMT elements of 3.5 μm (5 μm in the y'-direction).

FIG. 8 represents the emission light imaged by the PMT array. The full excitation field-of-view of 60×70 μm² (x-y') is imaged onto the PMT array with overall magnification of 200×. Each element with height 0.8 mm images a 4 μm axial slice (y') of the scanning beam. The imaging resolution in the y'-direction is defined by the demagnified PMT element separation of 5 μm (3.5 μm in the y-direction). The 0.2 mm dead space between PMT elements results in some signal and information loss. As the beam scans, the detected light hits different portions of the PMT. Data is acquired every 10 ns. During the usable portion of the scan when the excitation beam is focused on the sample (from 0.27 μs to 0.93 μs into each scan), collected data is used towards forming images (see FIG. 11). During the unusable portion of the scan, when the excitation beam is not tightly focused or distorted at the sample, collected data is unused.

FIG. 9A-D illustrate aspects of a LEAD system (i.e., microscope) operation in accordance with an implementation of the present disclosure.

Figure 9B:
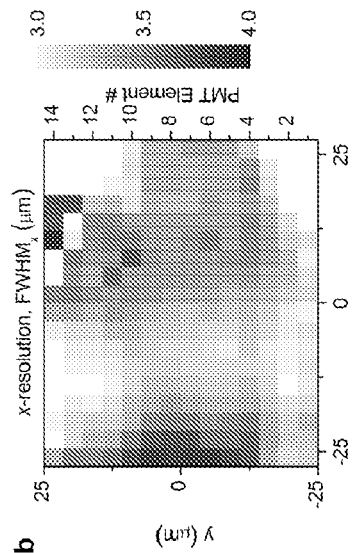
FIGS. 9A-D illustrate aspects of a LEAD system operation according to an implementation of the present disclosure.
Figure 9D:
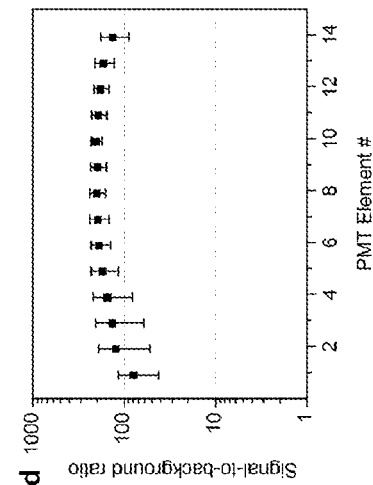
Figure 9A:
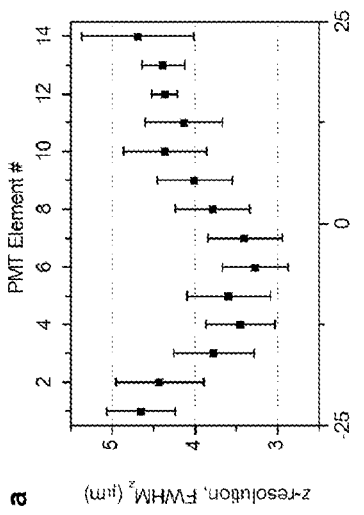

FIG. 9A is a graph showing the point-spread function FWHM in the flow direction. Data for the plot were obtained by imaging 0.5 diameter fluorescent beads embedded in agar within the device, and the device was translated through the imaging region. The FWHM ranged from 3.4-4.7 μm (FWHM) in the z-direction.

FIG. 9B is a plot of the point-spread-function FWHM in the scan direction. Data for the plot were obtained by imaging 56,000 0.5 μm diameter fluorescent beads flowing in the device. The FWHM was found to be between 3.0-4.1 μm in the scan-direction (x) across the device cross-section. No beads were detected along some edges of the device due to the parabolic flow velocity profile.

Figure 9C:
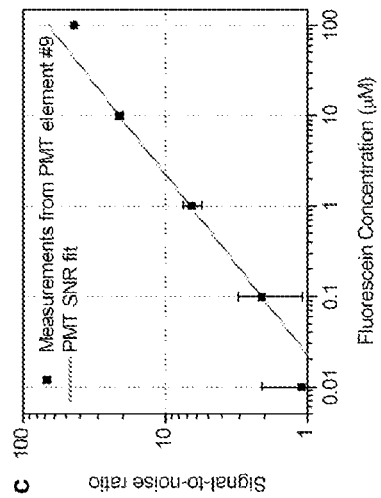

FIG. 9C is a graph of measured SNR for different concentrations of fluorescein flowing in the device and detected by the PMT array (element #9 is shown). A SNR model for PMTs gives a collection efficiency of the system of 2.6±1.1% and a detection limit (SNR=1) of 22.3±9.0 nM, corresponding to 420±170 molecules of fluorescein in the excitation volume imaged by each PMT element. Uncertainty arises from the varying signal level across experimental repetitions.

FIG. 9D is a graph of measured signal-to-background ratios (SBR) for a polyQ40 strain C. elegans moving at 1 m/s and neurons in a mouse brain slice imaged with our platform. The SBR exceeds 200 for the center PMT elements and drops off for surrounding elements due to their decreased responsivity.

To deliver C. elegans through the imaging region at high speeds, a microfluidic device consisting of a loading chamber, an imaging channel with a width of 55 µm and a height of 50 µm to guide individual animals through the excitation FOV, and a pressurized valve system to control delivery rate and speed was used. The maximum speed is limited to 1.4 m/s by the Nyquist criterion defined by the minimum beam width in the flow-direction of 3.5 µm and the scan period of 1.25 µs.

Figure 10A:
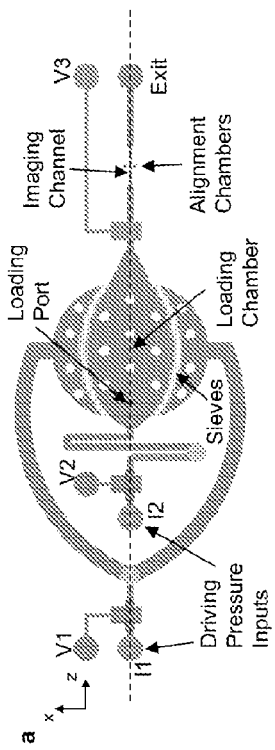
Figure 10B:
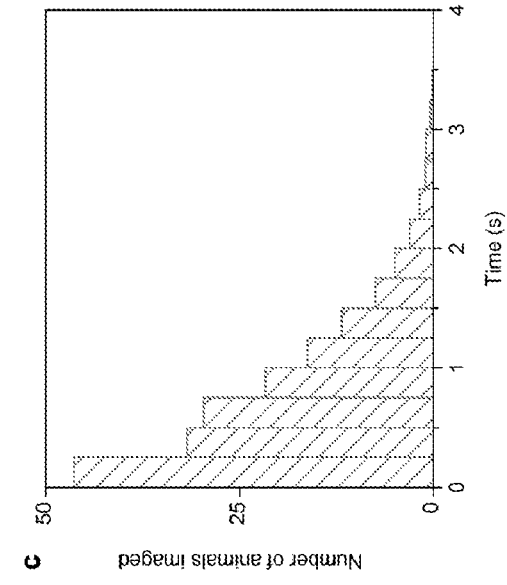
FIGS. 10B-C illustrate aspects of the microfluidic device's operation according to an implementation of the present disclosure.
Figure 10C:
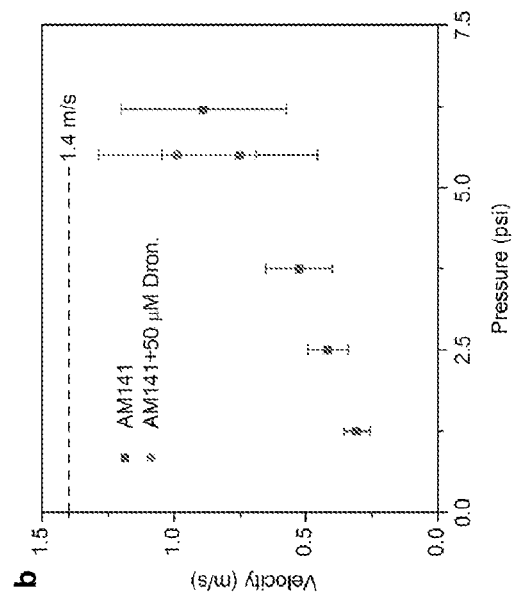

FIGS. 10A-C illustrate a microfluidic device according to an embodiment of the present disclosure, and aspects of its operation. FIG. 10A depicts the microfluidic device schematically and in a corresponding cross-section. Hundreds of animals can be loaded into the main chamber through the loading port, and the sieve structure prevents backflow of the worms through the inputs. The input ports (I1,I2) apply a driving pressure to the animals to send them through the imaging channel, and the valves (V1, V2, V3) control when that pressure is applied. Fluorescent beads can be loaded into the alignment chambers on both sides of the imaging channel to aid in device alignment with the excitation beam.

FIG. 10B is a graph of animal velocity versus driving pressure at I1 and I2. For polyQ40 animals without drugs and those treated with 25 µM dronedarone, 6.2 psi was used to flow animals at 0.89±0.31 m/s speed limit. Animals treated with 50 µM dronedarone tend to be smaller, and only 5.5 psi was required for flow at 0.99±0.30 m/s.

FIG. 10C is a histogram of animal frequency distribution versus time for a typical experiment with a population of ~175 animals. The majority of animals are imaged in the first second of imaging because the rate of animals moving through the channel depends on the concentration of animals in the loading chamber.

Figure 11:
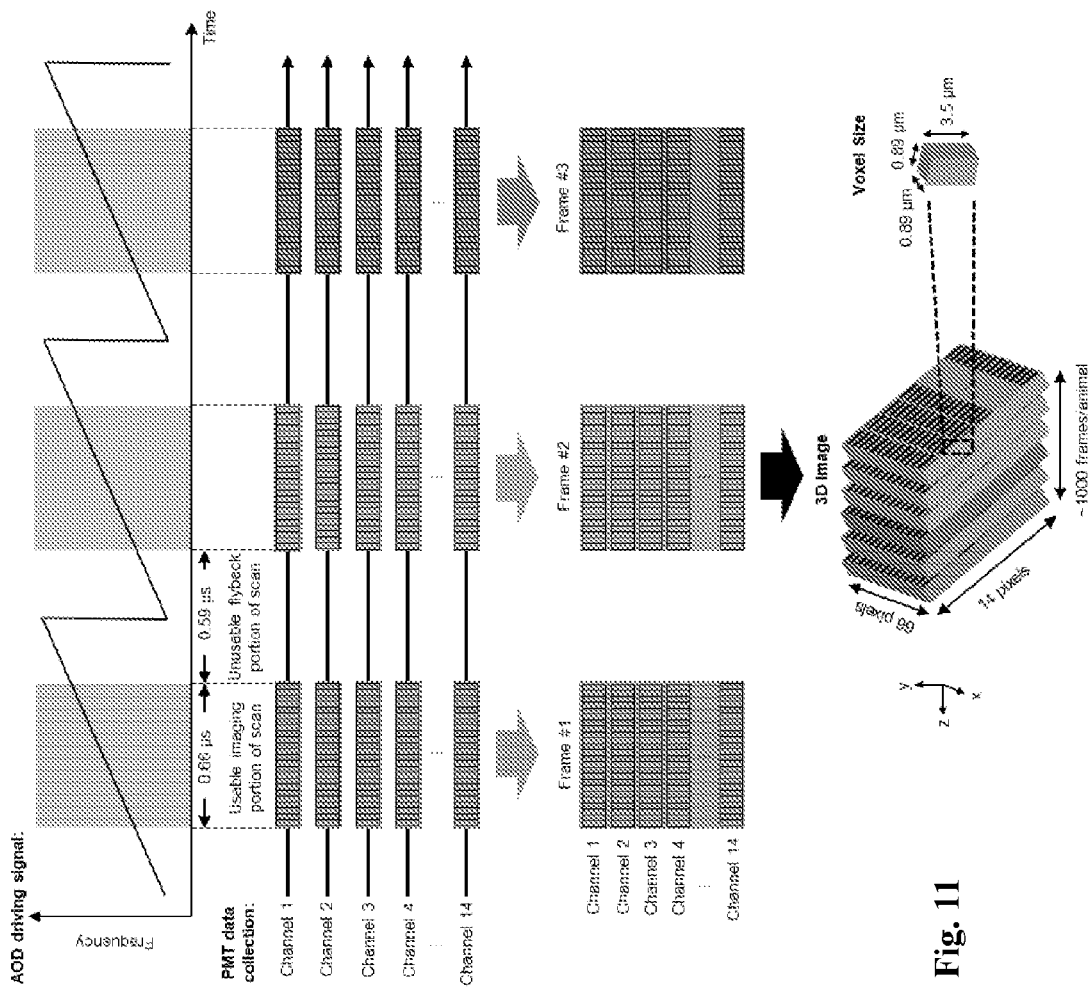
FIG. 11 illustrates a frame acquisition process and an image formation process.

A speed detection system measures the velocity of the animals as they pass through the excitation beam to correct pixel sizes in the flow-direction to account for possible speed variations. A HeNe laser generates two identical light sheets with a thickness of 5±1 µm that are separated by 210±1 µm, and two PDs record the transmission drop of the trans-collected beams as individual animals pass through the light sheets. Velocity can be calculated from the time delay between the two signals by continuous dynamic time warping[39]. A high-speed data acquisition card (DAQ) with 16-channels (Alazartech ATS9416) acquires the 14 PMT signals and 2 PD signals at 100 MS/s (10 ns pixel time) with a dynamic range of 14 bits, for a total data rate of 3.2 GB/s. A home-built preamplifier system amplifies the PMT signals with minimal noise to utilize the full dynamic range of the DAQ for our samples. The 66×14 pixel frames are constructed from the data collected in one AOD scan cycle (125×14 pixels) after removing the flyback portion of the scan (59×14 pixels). For 3D images of C. elegans, ~1,000 frames are stacked, and then skewed to account for the angled imaging plane with respect to the flow-direction (FIG. 11). Using the velocity of the animals, the pixels in the flow-direction are resized to 0.89 µm to match the pixel size in the scan-direction set by the speed of beam scanning.

FIG. 11 illustrates the frame acquisition and image formation process for a LEAD fluorescence cytometer, in accordance with some embodiments of the present disclosure. Frame acquisition and image formation from PMT data. Data collected during the usable, 0.66 µs long portion of the scan (highlighted gray region in the frequency-time plot) is used to form frames. Each frame consists of 66 data points captured every 10 ns by each of the 14 PMT elements to give frames with 66×14 (x-y') pixels. The frames are captured every 1.25 µs. To form the 3D image, the frames are stacked, and then skewed to account for the geometry of the system—the animal flow-direction (z) is at ~45° with respect to the excitation and imaging plane (x-y'). The pixels are converted from the skewed coordinate system (x-y'-z) to Cartesian coordinates (x-y-z) by compressing the pixel in the y-direction. After the compression and velocity correction, each pixel has dimensions 0.89×3.5×0.89 µm³ (x-y-z).

Figures 12A, 12B, 12C, 12D, 12E:
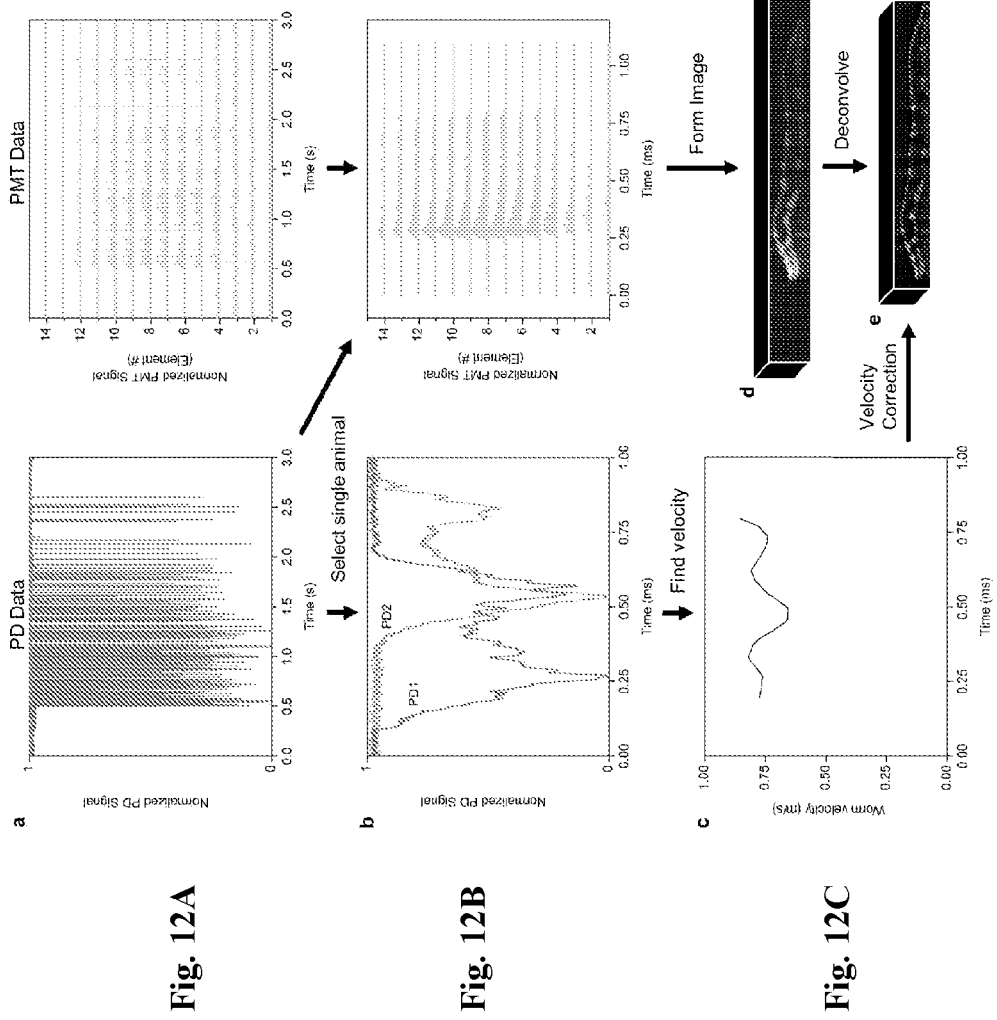
FIGS. 12A-E illustrate an image formation process for a LEAD fluorescence cytometer in accordance with an embodiment of the present disclosure.

FIG. 12 illustrates signal and image processing for a LEAD fluorescence cytometer, in accordance with some embodiments of the present disclosure. Two PDs record the transmission of two HeNe beams for animal speed detection (see FIG. 12A). Periods of low transmission in the PD data indicates when a C. elegans animal is in the imaging region. The 14 PMT channels record fluorescence signal from the animals (see FIG. 12B). Single animals are cropped out of the full PD and PMT data (see FIG. 12C). A dynamic time warping algorithm uses the two PD transmission signals to find the point-by-point time delay and velocity of the animal moving through the imaging channel (see FIG. 12D). A volumetric image of the animal is formed by reshaping the 14 PMT signals into 14 2D images (see FIG. 12E). A final image is formed using the velocity data to resize the pixels to 0.89×0.89 µm², and by 3D deconvolution using the PSFs from beads.

The resolution of the integrated system was characterized by imaging 0.5 µm diameter fluorescent beads within the microfluidic device onto the PMT array. For resolution in the z-direction, we imaged beads embedded in agar within the device and translated the device at 1 mm/s through the imaging region. The bead FWHM in the z-direction ranged from 3.4±0.4 µm to 4.7±0.7 µm along the y-direction (FIG. 9A). For resolution in the x-direction, beads flowing in the device were imaged, and the FWHM was found to range from 3.0±0.3 µm to 4.1±0.6 µm across the FOV (FIG. 9B). The bead point spread functions (PSF) in both directions correspond well with the beam size without the device, but show some aberrations in the y'-direction due to the skewed imaging configuration with respect to the coverslip. The 3D C. elegans images were deconvolved by the average bead PSF (FIG. 13) to correct for aberrations.

Figure 13:
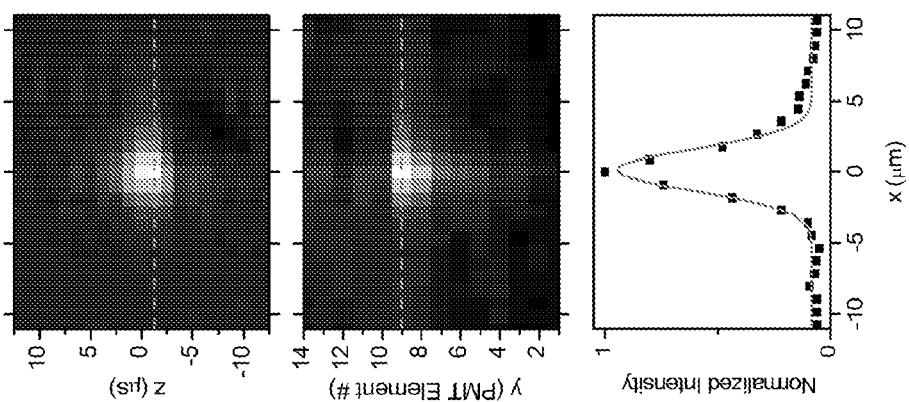
FIG. 13 is an example image of a bead taken using a LEAD system in accordance with an embodiment of the present disclosure.

FIG. 13 is an example image of a bead taken using a LEAD system in accordance with an embodiment of the present disclosure. Specifically, FIG. 13 is an example image of a bead flowing at ~1 m/s in the microfluidic device, with the scan-direction (x) FWHM=3.4±0.1 µm. The bead displays aberrations due to a tilted device. The average volume imaged by each PMT element, calculated from the average bead PSF in the x- and z-directions and the demagnified PMT element size, is 31 µm³. The average bead PSF in the imaging (x-y) plane and beam width in the flow-direction was used to deconvolve each image stack obtained from the samples.

Figure 14:
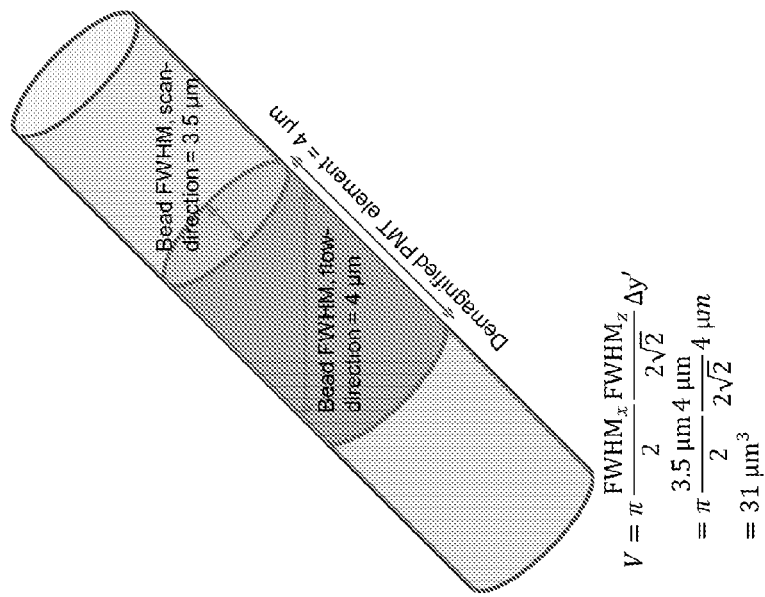
FIG. 14 graphically depicts an excitation volume imaged by a PMT element in a LEAD system in accordance with an embodiment of the present disclosure.

FIG. 14 is the average excitation volume imaged by a PMT element. The radii of the cylinder are determined by the beam width in the flow-direction (z) and the bead FWHM in the scan-direction (x). The height of the cylinder is the demagnified PMT element size.

The sensitivity of the system was determined by measuring the signal-to-noise ratio (SNR=$\mu_{signal}/\sigma_{signal}$) of different concentrations of fluorescein (0.1 M NaOH, pH=8.0) flowing in the device. A fit to the log(SNR) vs. log(concentration) data, excluding the high concentration data point where laser beam attenuation occurs, yields a slope of 0.502±0.025, indicating the system is shot-noise limited (slope of 0.5). SNR was fit to a simple PMT shot-noise model to find the detection limit and collection efficiency of the system[40]: SNR=$\sqrt{i_c/2.4eB}$, where e is the charge of an electron, B=20 MHz is the circuit bandwidth, and $i_c$ is the cathode current. The cathode current depends on the radiant sensitivity of the PMT and the power of fluorescent emission incident on the PMT: $i_c=S\eta\phi_f\sigma IVC_f$, where S=50 mA/W is the radiant sensitivity, $\eta$ is the collection efficiency of the optics, $\phi_f$=0.93 is the fluorescence quantum yield of fluorescein[41], $\sigma$=2.92×10$^{-16}$ cm$^2$ is the absorption cross-section of fluorescein[41], I=0.51 GW/m$^2$ is the illumination intensity for the available laser power (P=4 mW), V=31 µm$^3$ is the average volume detected by each PMT element, and $C_f$ is the concentration of fluorescein. Under this model, we obtain $\eta$=2.6±1.1%, which is close to the expected collection efficiency of 2.7% taking into account the fraction of emitted photons collected by the 0.50 NA objective (6.7%) and transmission through the collection path (40%). For this model, SNR=1 at $C_f$=22.3±9.0 nM, or 420±170 fluorescein molecules for the volume imaged by a single PMT element.

The LEAD system's high-speed capability is demonstrated by imaging thousands of an aggregation model *C. elegans*. The model simulates human Huntington's disease through CAG repeats in the huntingtin allele, with 35 or more repeats resulting in polyglutamine (polyQ) mediated aggregation, protein misfolding, and cellular toxicity[36]. Specifically, the polyQ40 strain was imaged with 40 CAG repeats at the late L4 stage when the disease phenotype presents as aggregation of YFP-labeled protein in the body wall muscle cells. The aggregates are 1-5 µm in diameter and distributed in 3D along the length of the animal, and therefore requires relatively high resolution volumetric imaging. As a positive control representing healthy *C. elegans*, we used the polyQ24 strain was used with 24 CAG repeats that displays diffused fluorescence rather than aggregates in the body wall muscle cells.

Populations of up to 300 animals were imaged. The animals moved at 0.89±0.31 m/s through the imaging channel, resulting in an imaging time of 1.07±0.26 ms per animal with the majority of the population imaged within 1 second (See FIGS. 10B, 10C). The maximum available laser power of 4 mW at the sample was sufficient to utilize the full dynamic range of our collection system. Pre-processed images exhibited coma and astigmatism from the angled coverslip and different optical path lengths taken by different portions of the image, but were corrected through deconvolution (see FIG. 12). The resulting image stacks not only compare favorably to wide-field fluorescent microscope images, but also demonstrate the axial sectioning capability of the detection scheme. Despite the ultrafast scanning, *C. elegans* images show SNRs exceeding 500 for the center PMT elements and slightly lower SNR for the less responsive surrounding elements in accordance with the PMT specifications (see FIG. 9D). 27±3 (median±standard deviation) aggregates per animal for the polyQ40 strain were found, similar to previous findings for worms at the same stage[36].

Figures 15A, 15B:
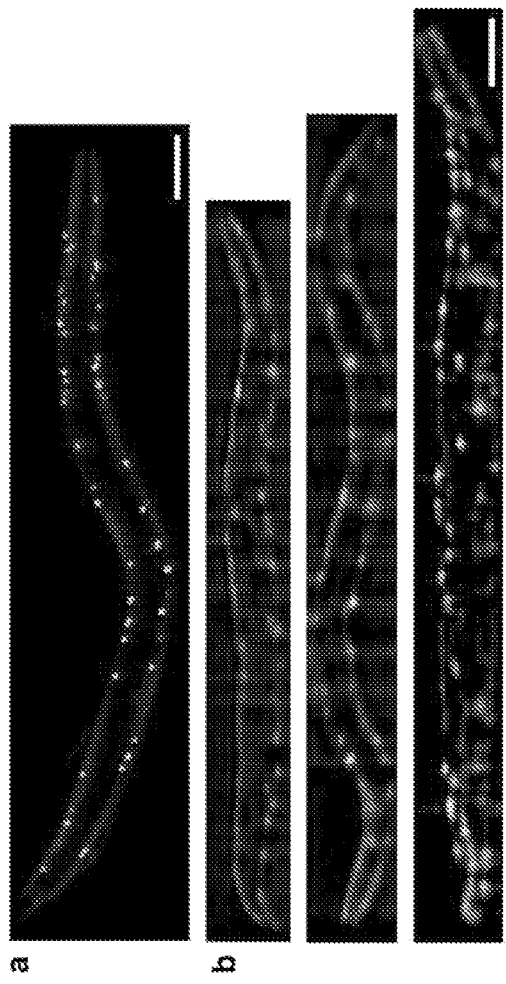
FIGS. 15A-B are images of C. elegans obtained with LEAD microscopy and wide-field microscopy, wherein FIG. 15A results from wide-field microscopy

FIGS. 15A-B are images of *C. elegans* obtained with LEAD microscopy and wide-field microscopy, where FIG. 15A is a PolyQ40 strain animal imaged with an inverted microscope and 4×, 0.13 NA objective and 84 ms exposure time. The scale bar in the image of FIG. 15A is 50 µm. FIG. 15B includes multiple images of PolyQ40 strain animals imaged with the LEAD system (maximum intensity projection) within 1 ms. The first animal (FIG. 15B, top) is in the early L4 stage, the second (FIG. 15B, middle) in mid L4 stage, and the third (FIG. 15B, bottom) in the late L4 stage. The number of aggregates increases with age, with the late L4 stage having similar numbers to (a) (FIG. 15A). The scale bar in the images is 50 µm.

The efficacy of the drug dronedarone on the polyQ40 animals was tested to demonstrate the ability of the LEAD cytometer to identify phenotypic changes within very short imaging times. It was previously observed that dronedarone, which is currently used to treat arrhythmias in humans[42], prevents the formation of aggregates in the polyQ40 animals and keeps the fluorescent proteins diffused throughout the body wall muscle cells[37]. PolyQ40 animals were treated with either 25 or 50 µM dronedarone at the L1 stage, and were imaged at the late L4 stage (FIG. 16A). The drug reduced aggregation to 16±5 and 7±2 aggregates per animal for 25 µM and 50 µM, respectively, showing a dose response (FIG. 16B). The system's high-speed 3D imaging capability for drug screening is established by the short imaging time for the effectivity of dronedarone reaches a statistically significant level—animals treated with 25 and 50 µM dronedarone reach p=0.001 in under 0.25 s and 0.10 s, respectively (FIG. 16C).

FIGS. 16A-C illustrate LEAD microscopy results from imaging polyglutamine (polyQ) mediated aggregation model *C. elegans* treated with the compound dronedarone. FIG. 16A shows images of polyQ24 control, polyQ40, and drug-treated polyQ40 animals imaged with the LEAD system (best focal plane). PolyQ24 shows diffused fluorescence throughout the body wall muscle cells. PolyQ40 presents distinct fluorescent aggregates in the body wall muscle cells. Treatment with dronedarone prevents the formation of aggregates, and we can detect a dose response. Scale bar=50 µm.

FIG. 16B is a plot illustrating the median number of fluorescent protein aggregates for populations of untreated and dronedarone-treated polyQ aggregation model animals, delivered through the microfluidic device and imaging system at ~1 m/s. Each data point represents an experiment with a full population delivered through the chip. The polyQ24 control animals show no aggregates, while the untreated polyQ40 animals have 27±3 aggregates per animal, and dronedarone-treated animals have 16±5 and 7±2 aggregates per animal for 25 µM and 50 µM, respectively.

FIG. 16C is a graph illustrating that the difference in the number of aggregates per animal for untreated and dronedarone-treated polyQ40 animals reaches statistically significant levels in under a quarter second, with 1 ms imaging time per animal and 4 ms between animals (see FIG. 10C). The results demonstrate the potential for high-throughput drug screening. The graph was generated by two-sample t-tests with unequal variances on equal sized subpopulations of untreated and drug-treated animals.

Figures 17A, 17B, 17C:
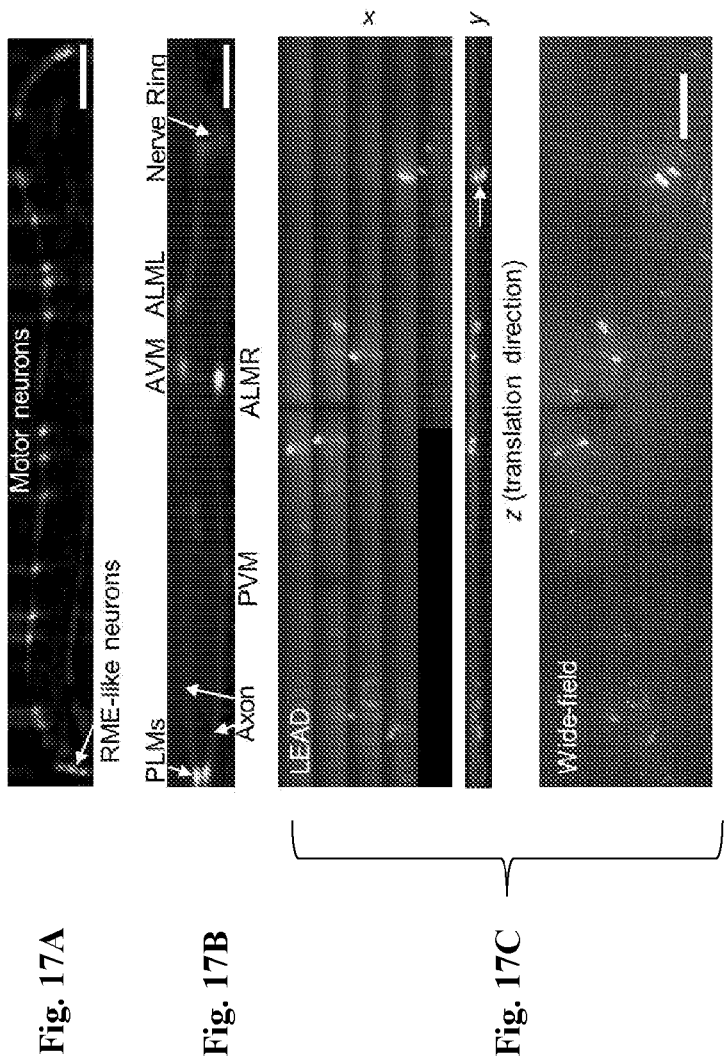
FIGS. 17A-C are exemplary images of samples according to an implementation of the present disclosure.

To show the flexibility of LEAD microscopy, two additional *C. elegans* strains with GFP-labeled GABAergic neurons (unc-25::GFP)[43] and touch receptor neurons (mec-4::GFP)[44] were imaged. Images of unc-25::GFP animals show the ventral cord, associated motor neurons, and RME-like neurons in the head (FIG. 17A). Neuron soma, axons, and the nerve ring are resolved in the mec-4::GFP animals, albeit at the limit of the detection, and shows the system can image small, dim features (FIG. 17B). SNR is low for the axons because of their small diameter, resulting in a small number of fluorescent molecules in the excitation volume. SNR can potentially be increased with a higher powered laser, considering the excitation intensity is ~10× less than saturation[45].

FIG. 17A-C are images of samples imaged with a LEAD microscope according to an embodiment of the present disclosure. FIG. 17A is a late L4 stage unc-25::GFP strain *C. elegans*, with GFP-labeled GABA-ergic neurons, including RME-like neurons in the head and motor neurons along the ventral cord. The thin ventral cord is at the detection limit of the system. The scale bar in the image is 50 μm.

FIG. 17B is a young L4 stage mec-4::GFP strain *C. elegans*, with GFP-labeled touch neurons. Planes 4-6 are summed, and the soma were saturated, so the axons are more visible. Scale bar=50 μm. FIG. 17C (top) is a maximum intensity projection images of Arc-dVenus transgenic mouse brain with neurons involved in fear conditioning labeled, stitching together 5 FOVs. A portion of the bottom-most FOV was not imaged. The y-z maximum projection image demonstrates the axial sectioning capability of the system, with the arrow indicating two stacked neurons. FIG. 17C (bottom) is an inverted microscope image of the same volume with 4×, 0.13 NA objective and 84 ms exposure time. The scale bar in the image is 100 μm.

Brain slices from Arc-dVenus transgenic mice[46] were also imaged with fluorescently labeled neurons involved in fear conditioning. For imaging with the LEAD system, the brain slices were mounted on a coverslip and the microscope stage, and translated through the excitation beam at 1 mm/s. We used all 16 PMT channels to image five adjacent FOVs and stitched them together to cover a volume of ~1,200×275×60 μm³. To simulate conditions using a faster secondary scanner, and to avoid averaging caused by the slow stage speed, 1 out of every 714 scan lines were sampled (see FIG. 17C). The maximum signal levels detected from the brain slices are similar to those obtained from *C. elegans* (see FIG. 9D), but the soluble fluorescence throughout the brain resulted in lower image quality. The spatial distribution of features in the resulting image compares well with an image captured by an upright microscope and camera. Axonal processes can be resolved with the LEAD system, which has the additional advantage of depth resolution. The results show a potential for brain imaging with MHz frame rates.

LEAD microscopy in accordance with certain embodiments of the present disclosure can provide the fastest volumetric fluorescence imaging available by combining new approaches for fast line-scanning with an optimized longitudinal AOD, and sensitive imaging of the full FOV with a linear PMT array. The sensitive, parallel detection by the PMT allows the AOD to scan an excitation line faster than previous imaging systems and form a virtual light sheet every 1.25 μs, resulting in an unprecedented 0.8 million frames per second and 739 million pixels per second. Although the frames are small, implementations of certain embodiments can achieve 333× higher frame rates and 5× higher pixel rates with similar resolutions compared to the current light-sheet microscopy systems, where the camera sensitivity limits the frame rate for biological imaging[19] (FIG. 3). Compared to imaging with AODs, implementations of certain embodiments reach 800× higher frame rates and 35× higher pixel rates. Even with such high frame rates and relatively low excitation intensities, a LEAD microscope according to an implementation of certain embodiments maintained high sensitivity with an imaging SBR over 200 and a detection limit of 420 fluorescein molecules. With 7× higher laser powers, close to saturation intensity, the detection limit may decrease to ~60 molecules, providing even higher sensitivity, SNRs, and SBRs.

The saturation intensity of GFP is approximated by:
$I_s \approx 1/\sigma\tau$ where $\sigma = 2.92 \times 10^{-20}$ m² is the absorption cross-section of fluorescein, and $\tau = 4.1$ ns is the lifetime of fluorescein, giving $I_s = 340$ kW/cm² or $P_s = 26$ mW with the average excitation cross-section utilized in certain implementations.

The detection limit of a system in accordance with certain embodiments, in terms of number of molecules, can be calculated from the measured detection limit (concentration) and the average PSF volume:

$$N = 22.4 \text{ } nM \text{ fluorescein} \cdot \frac{N_A \text{ molecules}}{1 \text{ mole}} \cdot \frac{1000 \text{ L}}{1 \text{ m}^3} \cdot \frac{31 \times 10^{-18} \text{ m}^3}{1 \text{ } PSF \text{ volume}} \approx 420 \text{ molecules fluorescein}$$

At saturation intensity, ~7× higher than the intensity used in this study, the detection limit may decrease to 60 molecules of fluorescein.

In an implementation of an imaging method in accordance with certain embodiments of the present disclosure, a blur-free, whole-animal flow cytometer was created, capable of imaging entire *C. elegans* moving at 1 m/s with 3.5 μm average resolution in 1 ms per animal. The system reaches imaging speeds similar to the fastest 2D cytometer[47], but has 3D capabilities, and is over 1,000× faster than previous 3D cytometry techniques[10,13]. The system's potential as a drug screening platform was demonstrated by imaging thousands of protein-aggregation model *C. elegans* treated with the compound dronedarone. After just 0.25 s into an imaging session, it was confirmed that dronedarone prevents the formation of protein aggregates with a dose response. The system eliminates immobilization as the rate-limiting step in *C. elegans* screening by providing high-speed blur-free imaging. When combined with a *C. elegans* population delivery microfluidic chip, whole-animal LEAD cytometry can potentially image 64 populations of animals within 2 or 3 minutes[38,48].

The performance of LEAD microscopy in accordance with some embodiments of the present disclosure can be determined by an interplay of several system parameters, including the number of resolvable points, rate of resolvable points, frame rate, and number of detector elements. The number of resolvable points, rate of resolvable points, and frame rate are all defined by the bandwidth and response time of the AOD. The number of resolvable points and number of detector elements independently define the x and y resolutions and FOVs for each frame. The number of detector elements and rate of resolvable points together can determine the overall data rate of the system. The focused beam width can define the animal's maximum allowable velocity and animal throughput for a given frame rate.

Figure 19:
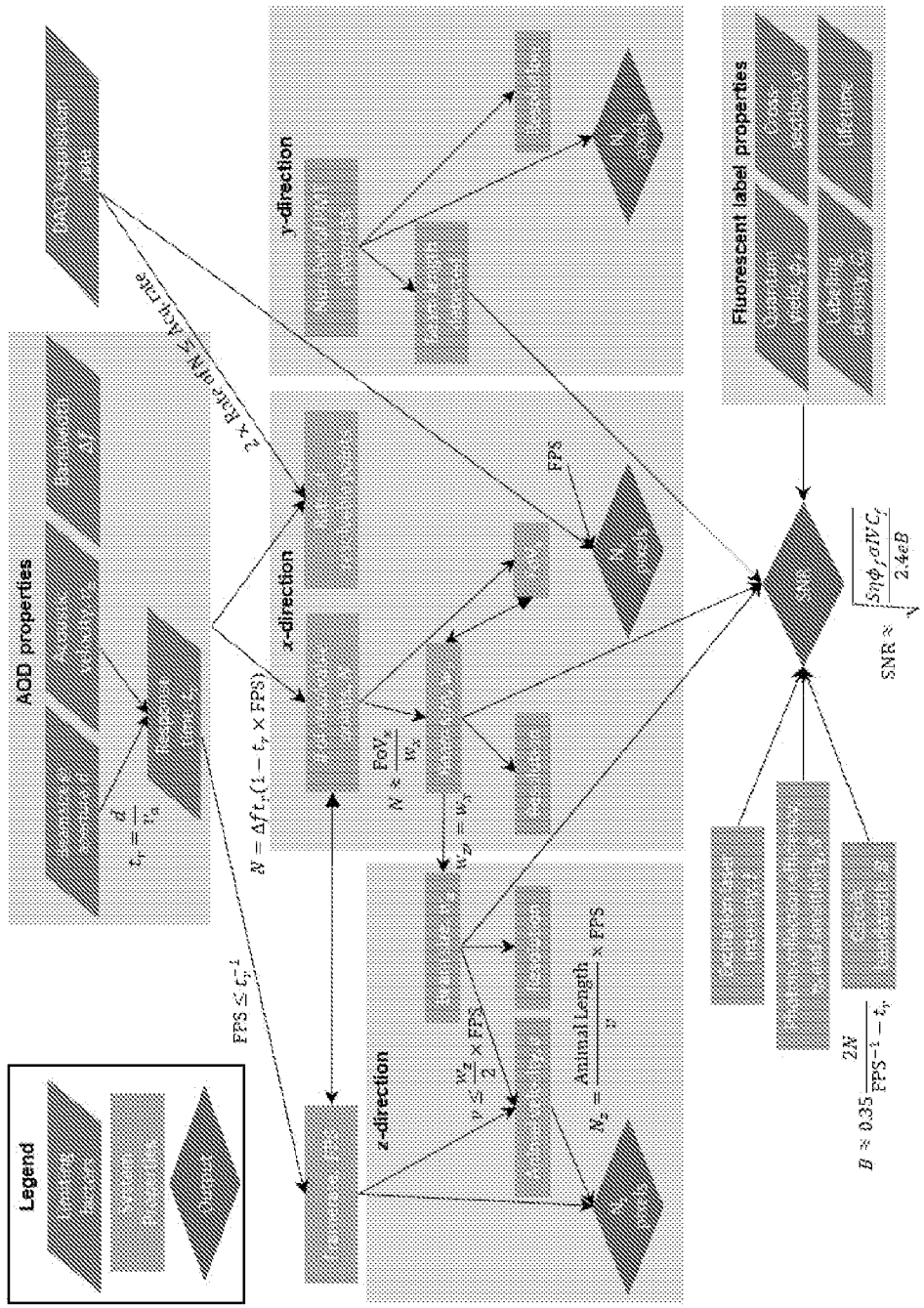
FIG. 19 illustrates considerations for designing LEAD microscopy according to an embodiment of the present disclosure.

The design of a LEAD microscope in accordance with one embodiment is outlined in FIG. 19. Factors defining the performance and related considerations are the AOD properties, data acquisition rate, and fluorescent label properties. Intermediate system properties include the framerate, number of resolvable points from the AOD, rate of resolvable points from the AOD, and the number of PMT elements used for imaging. Practical system properties include beam sizes, resolution, and field-of-view. The final image can be defined by the number of pixels and the signal-to-noise ratio.

It should be appreciated that the example embodiments and discussion of certain aspects of the various example implementations herein presented do not represent LEAD microscopy in all possible capabilities or forms; for instance, systems and methods for performing LEAD microscopy, with more pixels per frame, larger FOVs, and higher resolutions and speeds may be built. Some considerations relevant for implementing LEAD microscopy in other embodiments and/or in accordance with other aspects within the scope of the present disclosure include the following design aspects and other factors. Factors related to resolution and field-of-view:

Number of resolvable spots from AOD (N). In the scan-direction (x), the resolution and/or field-of-view may be increased with more resolvable spots from the AOD. More resolvable spots may be obtained by slower scanning, an AOD with higher bandwidth, or an AOD with a larger aperture or in shear configuration (at the cost of speed). For example, a system may have improved resolution by using an AOD with twice the bandwidth driven at 0.8 MHz may result in 45 resolvable points, improving resolution 2×.

Number of detector elements. In the imaging-direction (y'), the resolution and/or field-of-view may be increased with more detector elements. Currently, PMTs are available with 32 elements, and silicon photomultipliers can be configured for even more elements. However, acquisition of data can be limited by current data acquisition devices. DAQs with 16 channels at 100 MHz have become available only recently. For more detector elements, multiple DAQs and hard drives may be used in parallel, for example.

Factors Related to Signal-to-Noise Ratio:

Excitation volume. As excitation volume goes up, more fluorophores are available to absorb and emit light, increasing SNR.

Available laser power. In some embodiments discussed herein, the laser used was limited to delivering 4 mW to the sample; ~27 mW would be close to saturation.

Imaging speed. As the scanning speed, rate of resolvable points from the AOD (N/s), and data acquisition rate increase, the number of photons collected from a point on the sample decreases. The designed PMT circuit bandwidth should also scale with the rate of resolvable points during the usable scan period to keep up with the fast modulation of the signal from the sample, which can introduce more noise.

Photon collection efficiency. The collection efficiency of optics in some embodiments discussed herein is 2.6±1.1%, and can be increased with a higher numerical aperture collection lens. The system in accordance with certain embodiments disclosed herein can use long working distance objectives in order to prevent contact with the microfluidic device.

Fluorophore properties. Brighter fluorophores with higher saturation intensities and a higher labeling density may contribute towards higher SNR in *C. elegans* images.

Factors Related to Imaging Speed:

Signal-to-noise ratio. Ultimately, the imaging speed can depend on the number of photons that can be collected from the sample. See FIG. 20.

Frame rate. Ideal and maximum framerates may be determined by response time of the AOD, which can depend on the AOD aperture size (and beam size entering the aperture) and the acoustic velocity of the AOD crystal. An AOD with a small aperture (2.5 mm) has been used, and the fastest crystal (longitudinal $TeO_2$ with $v_a$=4,260 m/s) for 488 nm light. The beam size can be reduced below the aperture size to increase the framerate further, at the cost of number of resolvable points (resolution and FOV). The ideal frame rate for the AOD in accordance with some embodiments, giving the most resolvable points per second (N/s), is 0.852 MHz. 0.8 MHz was used in some implementations because this is the maximum frequency allowed by the bandwidth of the particular function generator used. Increasing the framerate beyond 0.852 MHz results in a lower number of resolvable points per second, and even fewer resolvable points per scan, but may be useful for applications where high framerates are absolutely necessary. For example, driving AOD #2 (which has an optimal frequency of 0.67 MHz) at 0.8 MHz can increase resolution.

Pixel rate. In accordance with certain embodiments, the data acquisition rate should be at least twice the rate of resolvable points from the AOD during the scan period. The peak N/s is limited by the AOD bandwidth (maximum N/s=bandwidth/4). AODs with higher bandwidths, as may be developed in the future, may be used. The pixel rate is also limited by the data acquisition card (the card used in some embodiments described herein has a maximum of 100 MHz). Single channel data acquisition cards with higher sampling rates are available, but are generally limited by the speed of analog-to-digital conversion.

Factors Related to Overall Animal Throughput:

Signal-to-noise ratio. Ultimately, the imaging speed can depend on the number of photons that can be collected from the sample.

Animal velocity. The maximum animal velocity can be limited by the size of the beam in the flow direction and the framerate of the system. In some embodiments, the animal velocity may not exceed v=$FWHM_z$/2×Framerate for proper sampling.

Animal delivery. Microfluidic device(s) in accordance with some embodiments disclosed herein can hold and image up to 300 animals from a single population at a time. For continuous animal delivery, and delivery of distinct populations, the device may be connected to, for example, a multiplexed delivery device (Ghorashian, N., Automated microfluidic platforms to facilitate nerve degeneration studies with *C. elegans*, 2013). The multiwell device can be loaded with different populations of *C. elegans* using widely available liquid handling systems to deliver a single population made of 100's of animals to our imaging system in under 3 seconds/population.

The rate of resolvable points can be increased with higher bandwidth AODs to half the DAQ card sampling rate. The x-direction resolution and/or FOV may also be improved using newly available AODs with higher bandwidth. The resolution and/or FOV along the excitation line can be increased with a detector array with more elements (silicon photomultiplier arrays with 256 elements are available, for example), which can also increase the overall data rate by 16 times (>10 GHz pixel rates). Bessel beam excitation can be used for applications requiring improved x-resolution or a large FOV along the excitation line. However, as with any imaging system, improvements to resolution, FOV, and imaging speed can come with a tradeoff with SNR. For example, improving the resolution to 1.5 µm in all directions for *C. elegans* imaging using an AOD with twice the current AOD's bandwidth and 32 detector elements may restrict maximum usable frame rate to 0.25 MHz while maintaining an SNR >10. Alternatively, the frame rate may be increased beyond 1 MHz with resolution similar to the system described in accordance with some embodiments (FIG. 18, FIGS. 20A-D).

Figure 18:
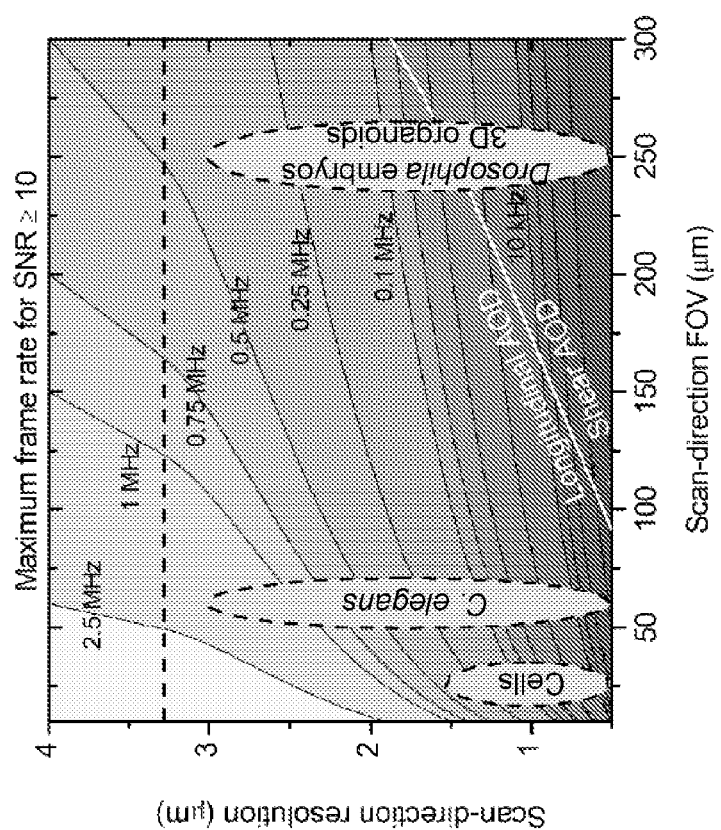
FIG. 18 is a graph of frame rate versus resolution and FOV while maintaining SNR>10 for various embodiments of LEAD microscopy.

FIG. 18 is a graph of scan resolution, field of view, and frame rate for SNR>10 that may be utilized in LEAD microscopy in accordance with embodiments of the present disclosure. LEAD fluorescence microscopy can be adapted to meet a wide-range of parameter space requirements of other biological samples. Presented here are theoretical maximum achievable frame rates when imaging samples labeled with 1 µM fluorescein equivalent using a $TeO_2$ AOD with 150 MHz bandwidth and 5 mm aperture while maintaining an SNR>10. The FOV and resolution define the number of resolvable spots required from the AOD. For example, cellular cytometry requiring a 25 µm FOV and 1 µm resolution can reach 0.1 MHz frame rate. For larger samples requiring larger FOVs and resolutions better than 1.5 µm (a large number of resolvable spots), such as *Drosophila* embryos, a shear AOD can be used because the longitudinal configuration may not attain a high number of resolvable spots even with low frame rates. Below the dashed line, frame rate is limited by the photon budget, and the system can reach higher frame rates for brighter samples. Above the dashed line, frame rate is limited by the AOD properties rather than the photon budget, and higher frame rates can be attained with larger bandwidth AODs. Camera-based imaging modalities may not reach the displayed resolution-FOV-frame rate parameter space that LEAD microscopy in accordance with embodiments of the present disclosure can provide, due to insensitive detection.

FIGS. 18 and 20 are formed under the following assumptions. The PMT shot-noise model is used, SNR= $\sqrt{i_c/2.4eB}$ and $i_c = S\eta\phi_f \sigma IVC_f$, where S=50 mA/W is the radiant sensitivity of the PMT, $\eta$=2.6% is the collection efficiency of the optics, $\phi_f$=0.93 is the fluorescence quantum yield of fluorescein, and $\sigma$=2.92×10$^{16}$ cm$^2$ is the absorption cross-section of fluorescein. For the other parameters, an ideal system is assumed:

1) Saturation intensity of $I_s$=340 kW/cm$^2$ is used to maximize SNR (current setup uses ~50 kW/cm$^2$).
2) The number of PMT elements scales such that the demagnified element size equals the resolution.
3) The desired FOV and resolution determines the number of resolvable points from the AOD: N=FOV/resolution.
4) The beam size entering the AOD aperture, d, is selected to meet the desired N and frame rate, while minimizing the rate of resolvable points during the usable imaging period (and minimizing the circuit bandwidth and noise), according to N=Δfd/$v_a$ (1−$v_a$t), where t=(Frame rate)$^{-1}$.
5) The bandwidth, B, of the PMT circuit is set according to the rate of resolvable points from the AOD during the usable imaging period: Rise & Fall Time=(t−d/$v_a$)/2N, and B=0.35/(Rise & Fall Time).
6) It is assumed that the data acquisition card can acquire at 1/(Rise & Fall Time).
7) A Bessel beam is used for a constant resolution in the scanning and flow directions over the full FOV.

Systems and methods for LEAD microscopy in accordance with embodiments of the present disclosure have the flexibility for further imaging applications ranging from flow cytometry to time-lapse imaging. For cytometry of cells, 3D tissue spheroids, or *Drosophila* embryos, the AOD and optics can be changed to cover a wide range of FOVs and resolutions (FIG. 18). For example, LEAD cellular cytometry with 1 µm resolution and 0.1 MHz frame rate may reach SNR=10 for ~1 µM fluorescein equivalent, within typical values for cells[49], or similar concentrations at higher resolutions (FIG. 18 E-F). LEAD microscopy can also be implemented as a time-lapse, calcium imaging system with the addition of a second scanning axis. As brighter voltage indicators become available, LEAD microscopy offers a platform capable of direct imaging of brain activity at kHz volumetric rates[2]. Overcoming the speed and sensitivity limits of currently existing fluorescence imaging technologies, LEAD microscopy provides the fastest fluorescence imaging available and may spark future research in cytometry and brain imaging.

FIGS. 20A-F show the theoretical signal-to-noise ratios and detection limits for a LEAD system in accordance with some embodiments of the present disclosure. FIG. 20A shows the theoretical SNR of LEAD as a function of frame rate and resolution, for a FOV of 60 µm, fluorescein concentration of 1 µM (typical for cells[55]), and using the current AOD (75 MHz bandwidth, 2.5 mm aperture, longitudinal $TeO_2$). Some resolution and frame rate combinations as shown are unreachable, limited by the AOD aperture or bandwidth (white region). For the highest resolution imaging, the full AOD aperture is used. For high-speed imaging, it is advantageous to underfill the AOD aperture to utilize the full AOD bandwidth and reach the maximum rate of resolvable points during the scan period. In some embodiments, the system is operated at the optimal point where the highest resolution is reached while maximizing the rate of resolvable points (yellow dot). FIG. 20B shows the minimum fluorescein concentration for SNR=1 for the system in FIG. 20A. FIG. 20C shows theoretical SNR for a FOV of 60 µm and fluorescein concentration of 1 µM using a higher bandwidth, larger aperture AOD (150 MHz bandwidth, 3.2 mm aperture, longitudinal $TeO_2$). The larger aperture and higher bandwidth extend the range of resolution and frame rate combinations. Furthermore, higher SNR is reached for identical imaging conditions because the same number of resolvable points can be reached with a lower rate of resolvable points during the imaging portion of the scan, allowing lower bandwidth circuits with less noise. FIG. 20D shows minimum fluorescein concentration for SNR=1 for the system in FIG. 20C. FIG. 20E shows theoretical SNR for a LEAD system imaging a smaller FOV of 25 µm (for applications such as cellular imaging), and using the AOD in FIGS. 20A-C. The black region indicates the regime where SNR<1 for 1 µM fluorescein. FIG. 20F shows the minimum fluorescein concentration for SNR=1 for the system in FIG. 20E.

As will be described in further detail below with respect to embodiments shown in FIGS. 21 and 22, LEAD microscopy can also be implemented as a time-lapse, multiphoton imaging system with the addition of a second scanning axis to directly image action potentials in the brain at kHz volumetric rates using new voltage indicators[2]. Other implementations can be used for calcium imaging, sodium imaging, and/or voltage imaging at kHz rates. Multiphoton imaging requires dispersion compensation for the AOD, but the innate sectioning capability of nonlinear imaging can allow a single objective for excitation and collection. As one example implementation, a LEAD system for brain imaging can scan and image an excitation line using an AOD at 200 kHz with 212 resolvable points and a PMT array with 256 elements with cellular resolution. When combined with recent advances in axial scanning[50], the FOV can travel hundreds of microns axially to cover, for example, the entire zebrafish brain with a 600×800×200 µm$^3$ volume with 3-4

µm lateral resolutions or a region of mammalian brain with 1,000's of neurons at unprecedented 1 kHz volumetric rates, the ultimate goal in brain imaging. Scanning methods that may be utilized in various other embodiments can use mirrors, polygonal mirrors, MEMs mirrors, shear AODs, AODs with a chirped frequency signal or in dwell mode, and/or EODs.

LEAD systems and methods for nonlinear microscopy in accordance with some embodiments of the present disclosure will now be described in further detail. LEAD nonlinear microscopy embodiments, such as two-photon or multiphoton fluorescence microscopy, can be implemented for applications such as volumetric imaging of the brain, the beating zebrafish heart, or any type of 3D tissue constructs. Nonlinear microscopy provides innate axial sectioning capabilities, eliminating the need for a separate objective for imaging. In addition to exciting a plane along the optical axis and imaging with an orthogonal objective, as in one-photon LEAD microscopy, nonlinear LEAD microscopy has the option to excite a plane orthogonal to the optical axis, and image through the same objective (FIG. 21). Nonlinear LEAD microscopy uses a laser generating ultrafast pulses with repetition rates equal to or greater than the rate of resolvable points generated by the acousto-optic deflector (AOD) during scanning. Lasers that may be utilized include bulk lasers (oscillators and amplifiers) or fiber lasers with repetition rates above 10's of MHz, and new burst-mode lasers with GHz repetition rates[53]. In other words, ultrafast lasers with repetition rates ranging from 10's of MHz to 10's of GHz with or without burst of pulses may be used. In addition, LEAD microscopy uses dispersion compensation to account for dispersion of laser pulses in the AOD crystal and other optical components. Means for dispersion compensation include using a prism pair, dispersion compensation fibers, or gratings.

Simultaneous spatial and temporal focusing (SSTF)[54] can be added to the single-objective nonlinear LEAD configuration to improve the axial resolution of the line-excitation to approximately point-scan levels[55,56], and to maintain the integrity of the line-excitation pattern as it propagates through scattering media[57,58]. SSTF can be implemented by adding a diffraction grating at the imaging plane—the spectral components of the ultrafast pulse are dispersed along one dimension in space, broadening the pulse in time, only to come back together and recover the transform limited pulse width at the sample plane. Other approaches include replacing the grating with a grism[59], or a digital micromirror device (DMD) acting as a grating[60].

Axial scanning can be added to the SSTF nonlinear LEAD system to image volumes at kHz rates. FIGS. 22A-C depict several axial scanning approaches: mounting the objective on a piezoelectric stage that moves along the optical axis[61] (FIG. 22A); adding a tunable lens, such as an electrically tunable lens (ETL)[62] or tunable acoustic gradient (TAG) lens[63], before the objective (FIG. 22B); or remote focusing, where an axially scanned mirror is imaged onto the sample[50] (FIG. 22C). In some embodiments, a spatial light modulator (SLM) can be used as a reflective lens before the objective[53,54].

Figure 21:
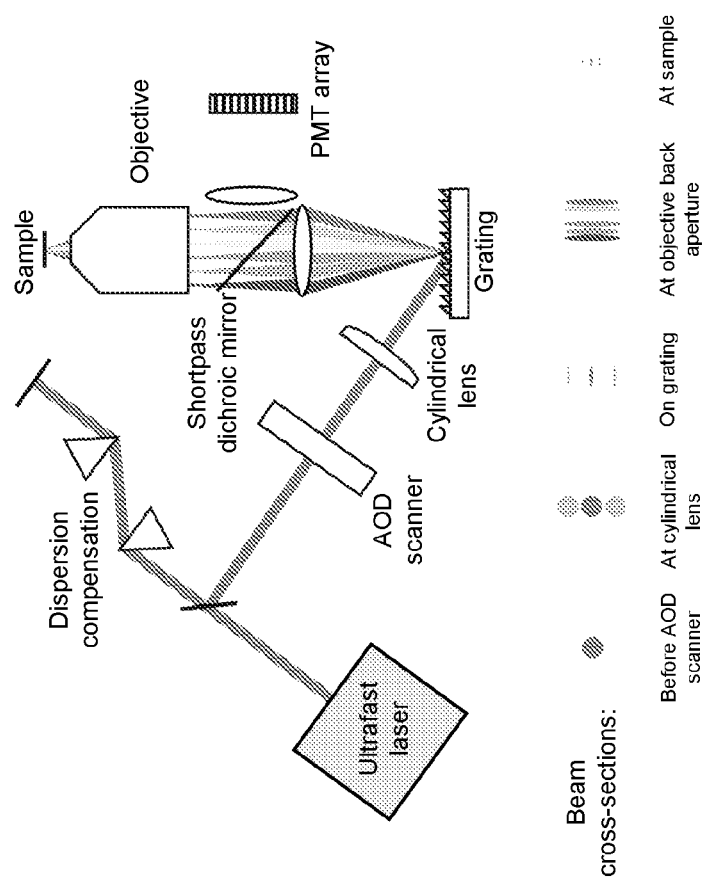
FIG. 21 schematically depicts a LEAD nonlinear microscopy system according to an embodiment of the present disclosure.

FIG. 21 schematically depicts a LEAD nonlinear microscope setup according to an embodiment of the present disclosure. The LEAD nonlinear microscope in FIG. 21 is a line-scanning microscope with ultrafast beam scanning provided by an acousto-optic deflector (AOD) and sensitive detection of fluorescence emission by a multi-element PMT array. While the implementation of FIG. 21 utilizes an AOD, it should be appreciated that LEAD can employ other types of deflectors besides AODs and may utilize other types of detectors rather than PMT arrays. A simultaneous spatial and temporal focusing setup, implemented with a diffraction grating, improves axial sectioning and preserves the line excitation pattern through scattering media. An ultrafast pulsed laser beam passes through a beamsplitter to a prism pair to compensate for dispersion from downstream optical components including the AOD and grating. The beam is deflected towards beam-shaping optics, which shapes the beam to the desired shape at the AOD aperture. The AOD scans the beam in one direction at 100's of kHz rates. Additional optics correct for the cylindrical lens effect caused by the chirped-frequency-driven AOD, and shape the beam to achieve the desired scan range, field-of-view, and beam size at the sample. A cylindrical lens acts as a scanning lens and focuses the beam in the scanning direction. The beam forms a line at the grating that scans perpendicular to the length of the line. The grating disperses the pulse in space for temporal focusing, and the beam at the grating is imaged to the sample with a tube lens and objective. At the sample, the beam is spatially focused and scanned in one dimension, and temporally focused in the other as the spectral components of the beam converge. Emission from the sample is filtered and imaged onto the linear PMT array.

FIGS. 22A-C schematically depict LEAD nonlinear microscopy systems in accordance with embodiments of the present disclosure, with various forms of axial scanning. FIG. 22A schematically depicts axial scanning by moving the objective (e.g., using a piezo-electric stage). FIG. 22B schematically depicts axial scanning using an electrically tunable lens (ETL) or tunable acoustic gradient (TAG) lens. An electrically tunable lens and compensation lenses placed before the objective lens add curvature to the incoming wavefront, to either focus the beam before or after the geometric focus of the objective lens. The focal length of the tunable lens is rapidly oscillated for axial scanning. FIG. 22C schematically depicts remote focusing according to an embodiment of the present disclosure. In a remote focusing setup, the excitation beam is first focused onto a fast axially scanned mirror, and then imaged onto the sample. Emission from the sample propagates back to the axially scanned mirror before being imaged onto the PMT array. The remote focusing setup both scans the beam axially onto the sample and brings emission back into focus onto the PMT array. The objectives and optics between the objectives are chosen to minimize additional aberrations.

Figure 23:
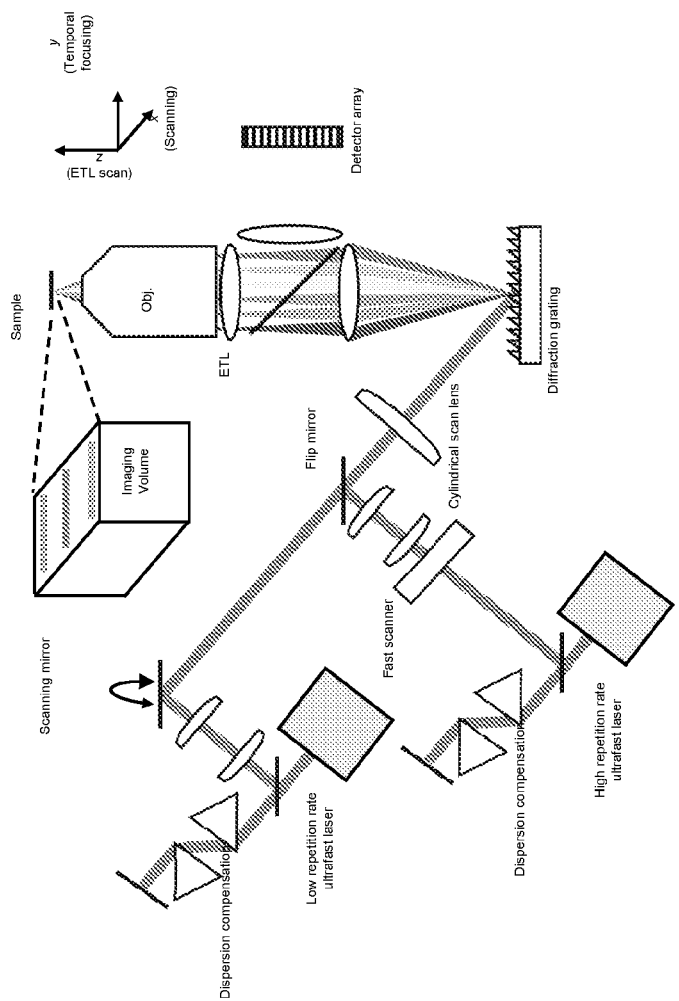
FIG. 23 schematically depicts a LEAD microscopy system with two scanning systems and two laser systems to reach different scanning speeds, in accordance with an embodiment of the present disclosure.

FIG. 23 schematically depicts a LEAD microscopy system with two scanning systems and two laser systems with different properties (repetition rate, power) to reach different scanning speeds, in accordance with an embodiment of the present disclosure. Depending on the speed of the scanner and the rate of resolvable points the scanner is able to generate, different ultrafast laser systems can be used for excitation. In this embodiment, the repetition rate of the laser system must be equal to or great than the rate of resolvable points. For multiphoton excitation deep within a scattering sample, µJ pulse energies are required at the sample. Some examples of laser systems for each scanner include the following: Galvanic mirror, 0.1-1 MHz, >0.1-1 W; Polygonal mirror, 5-40 MHz, >5-40 W; MEMS mirror, 0.1-20 MHz, >0.1-20 W; EOD, 1-30 MHz, >1-30 W; AOD, 10-80 MHz, >10-80 W. Fast scanning systems such as embodiments using AOD scanning, have the axial scanner scanning continuously, to avoid the settling time associated with some axial scanners such as an electrically tunable lens.

LEAD microscopy in accordance with systems and methods according to the present disclosure has numerous practical applications. Some examples mentioned above, and additional applications, include, but are not limited to: Fluorescence flow cytometer for cells, 3D tissue constructs including organoids or spheroids, or small animal models including *Caenorhabditis elegans, Drosophila melanogaster* embryos, and *Danio rerio* embryos; Bright-field flow cytometer for the above specimens; Volumetric fluorescence lifetime microscopy (FLIM); Volumetric phosphorescence lifetime microscopy (PLIM); High speed particle image velocimetry (PIV) in microfluidic channels or other high-speed applications such as combustion, supersonic flows; Laser speckle contrast imaging; Line confocal imaging. Applications for LEAD nonlinear microscopy, such as two-photon microscopy, in accordance with systems and methods according to the present disclosure include but are not limited to: Kilohertz volumetric rate brain imaging of fluorescence, calcium signals, or action potentials; Kilohertz volumetric imaging of the beating zebrafish heart. Various industrial applications include but are not limited to: Non-contact 3D inspection of semiconductors; Profilometry; and Surface roughness measurements.

Two-Photon Line Excitation Array Detection Microscopy

Neurological disorders—such as migraine, dementia, depression, and motor neuron disease—are now the leading cause of disease burden globally, due to an aging population and successful prevention and intervention of other disorders [89]. For example, 5.5+ million Americans have Alzheimer's disease, costing nearly $300 billion per year. Even with a greater availability of treatments, deaths due to neurological disorders have increased 37% over the past 25 years, and are expected to continue to increase [89]. Despite this growing burden and cost of neurological disease, how the brain operates to give rise to diseases and behaviors is largely unknown.

The brain consists of billions of neurons communicating at millisecond timescales within widely distributed neural circuits [13]. Each neuron has thousands of connections to other neurons, and the neural circuits span several millimeters or more in three-dimensions. The neurons communicate electrochemically through action potentials lasting just milliseconds. A depolarization of a neuron causes the opening and closing of ion channels in the membrane, which may result in an action potential, a further depolarization followed by a rapid repolarization. The action potential propagates down axons to stimulate and communicate with other neurons.

To understand the brain and neurological disorders, a map of the physical and functional connections of neurons within each neural circuit is desired [12]. Such a mapping requires high-speed volumetric monitoring at the timescale of action potentials and the field-of-views of neural circuits. A recent push towards mapping the brain has resulted in many monitoring techniques, but a complete picture of the brain has not yet been formed because the techniques are too slow, too invasive, or don't sample enough neurons.

Electrical recordings of the brain have revealed the high-speed dynamics of action potentials. The opening and closing of ion channels that fuels the depolarization—repolarization process can take as little as milliseconds in the case of sodium ion channels [14], or up to 100 milliseconds in the case of calcium ion channels [13]. Furthermore, action potentials can propagate down axons at up to 100 meters per second [90]. Recently, high frequency oscillations of neuron electrical activity from 80 Hz-500 Hz have been linked to epilepsy [91]. While these findings show the need for high-speed monitoring of neurons at up to kHz sampling rates, the recordings are either performed by electroencephalogram, which do not have cellular resolution, or by electrodes/patch clamping, which are highly invasive and only record activity of the neurons that are in contact with the electrodes/pipette.

The advent of fluorescence calcium indicators has shown the potential of two-photon imaging systems for making noninvasive, novel neurological measurements deep within the brain [6,92-94]. Standard two-photon microscopes reach just 30 frames per second, which is too slow to capture calcium activity in volumes. On the other hand, high-speed random-access point-scanning microscopes have monitored the electrical activity of a few discrete points in neurons at kHz sampling rates. With these microscopes, it is possible to detect millisecond-scale time delays in the calcium response at different points along an axon to measure the propagation speed of action potentials [43,45]. Similarly, measuring the time delay between the calcium signals of different neurons can potentially determine the flow of information in neural circuits. The calcium signal can also be deconvolved by a known calcium indicator response to recover the underlying electrochemical signaling with near-ms precision, and resolve action potential spike trains at up to 30 Hz [40]. Given a high enough signal-to-noise ratio, the imaging systems can also monitor the dynamics of sub-threshold electrical activity in dendrites that do not generate action potentials [45]. However, these microscopes have relatively limited pixel rates.

The relatively low pixel rates of serial acquisition approaches are overcome by using cameras. A line-scanning temporal focusing approach reached 200 frames per second when imaging 3D phantoms of neuronal networks [37]. However, deep brain imaging presents challenges for camera-based imaging. The brain is a turbid medium, causing the excitation light and emitted light to be scattered. Scattering reduces the intensity of light reaching the focal plane, and causes a degradation of the excitation pattern (whether it be wide-field, line-scanning, or a pattern to excite just specific neurons). More importantly, the number of emitted photons reaching the detector is reduced, lowering the signal-to-noise ratio for cameras with high readout noise, and the photons are deflected to the wrong pixels, causing image blurring.

While current two-photon imaging methods present a step forward towards noninvasive measurements of neuronal activity, they fall short in capturing high-speed dynamics across whole volumes, especially in moving specimens. Because the brain is densely packed with neurons, ideally a whole volume would be imaged within milliseconds to fully understand how information flows through neural circuits. Furthermore, living specimens move due to breathing and the heart beating, even when anesthetized. The movement can exceed hundreds of microns, requiring whole volume imaging to track the neurons for extended lengths of time. Finally, calcium indictors are slow relative to the high-speed electrochemical dynamics of action potentials. The fastest calcium indicators have tens of milliseconds rise time, and slower fall times [6], preventing them from capturing fast spike trains or high frequency oscillations. New voltage indicators can directly monitor the transmembrane potential of neurons at millisecond speeds [94,95]. However, voltage indicators are dim and require fast imaging systems capable of high signal-to-noise ratios to take full advantage of their benefits.

A new imaging system is disclosed to monitor neuronal activity in the in vivo brain, with the following design goals:
  Image large volumes to cover widely distributed neurological circuits (hundreds of microns field-of-view);

Image whole volumes at millisecond timescales to capture fast neuronal activity and track moving neurons (hundreds of kHz frame rate and kHz volumetric rate);

Distinguish individual neurons (micron-scale resolution);

Have a high signal-to-noise ratio (SNR>5);

Image hundreds of microns deep within the brain;

Provide a platform to take advantage of high speed voltage indicators, as they become brighter.

The line excitation array detection microscopy is extended to two-photon microscopy to meet the challenges of high-speed, time-lapse, volumetric brain imaging. Two-photon LEAD microscopy is based upon the same two principles of one-photon LEAD microscopy: line-scanning excitation and linear array detection. However, since two-photon microscopy provides innate axial sectioning capabilities, a single microscope objective can both excite a line orthogonal to the optical axis, and image that line onto the detector array. Furthermore, two-photon LEAD microscopy is designed for time-lapse imaging rather than cytometry.

The line-scanning and linear array detection approach of two-photon LEAD microscopy is well-suited for brain imaging. Compared to previous two-photon brain imaging approaches using point-scanning and serial acquisition with a PMT, LEAD microscopy uses parallel acquisition and is able to reach the much higher pixel rates needed to sample large neural circuits within milliseconds. Compared to widefield excitation and imaging with a camera, two-photon LEAD microscopy reaches higher SNR in low light by using highly sensitive detectors (such as PMTs and silicon photomultipliers). Two-photon LEAD microscopy is also less sensitive to blurring due to scattering since imaging is performed only along one axis, and photons scattered in the non-imaging direction do not contribute towards blurring.

However, two-photon LEAD microscopy introduces new challenges and drawbacks. Because line-excitation focuses the laser beam weakly along one dimension, the axial resolution is lower than point-excitation methods. Line-excitation also leads to a reduced beam size on the surface of the tissue, which can result in high out-of-focus background signal or even nonlinear ablation, which occurs at fluences of ~1-2 J/cm$^2$ for pulse widths of hundreds of femtoseconds [96].

The high-speed, parallel excitation also requires high laser powers to excite fluorescence, which can quickly heat the sample. Two-photon point-scanning imaging typically uses tens—hundreds of mW for imaging hundreds of microns deep into the brain [3,97]. The larger excitation area of line-excitation, and the high repetition rates required for fast scanning, demand up to 100× more power to reach the same intensities and signal level per pixel. However, a small rise in brain temperature can result in neuron misfiring, and a rise of 6-8° C. can cause irreversible protein denaturation [98]. Such a temperature rise has been shown to occur for two-photon imaging with ~250 mW targeting 250 µm below the dura [99]. Therefore, the size of the excitation line, the speed of scanning, or the depth of imaging is restricted in line-scanning by the laser power before thermal damage occurs. Alternatively, higher laser powers can be used if an on-off imaging cycle is utilized that allows the brain to cool between short imaging sessions. For example, 400 mW has been used to image 250 µm deep into the brain without thermal damage with a 10 s on, 20 s off duty cycle [99].

Finally, line-excitation and detection with multiple detector elements is still sensitive to scattering. As the laser pulse propagates through tissue, scattering can divert some of the photons and degrade the excitation pattern at the focal plane (in the case of two-photon LEAD microscopy, a line excitation pattern). The light emitted from the sample is also scattered. In the imaging configuration of LEAD microscopy, photons can be scattered onto adjacent detector elements, resulting in a blurring of the image. However, blurring for a 1D array of detectors is expected to be less than for a camera.

The incorporation of temporal focusing to two-photon LEAD microscopy overcomes many of the drawbacks associated with line-scanning. Temporal focusing is a method where the excitation pulse is temporally stretched everywhere except at the focal plane, resulting in reduced out-of-focus intensity [100,101]. Temporal focusing is realized by spatially dispersing the laser pulse spectrum on the back aperture of the objective lens, typically using a diffraction grating. Dispersing the laser pulse decreases the local bandwidth of the pulse and increases the pulse width. After the objective lens, as each spectral component focuses to the focal plane, the spatial dispersion is reversed and the pulse width is recovered at the focal plane.

Temporal focusing provides several advantages over standard line-scanning microscopy. First, temporal focusing can improve the axial resolution of line-scanning to near point-scanning levels [36]. Second, the transform-limited pulse width can be recovered at the sample, even for an input pulse with dispersion [101]. Temporal focusing acts as built-in dispersion correction. However, for line-scanning, large input pulse dispersion can result in the spatial focus and temporal focus not overlapping [102]. Therefore, external dispersion compensation may be necessary to overlap the two foci. Third, the pulse energy for out-of-focus nonlinear damage is increased [103]. The spatial dispersion of the pulse leads to larger out-of-focus beam sizes, and a reduction of the fluence. Combined with a longer out-of-focus pulse width, the out-of-focus ablation threshold is increased [96], allowing for higher laser powers to be used before the onset of damage at the brain surface. Fourth, the out-of-focus two-photon signal is reduced, which can increase imaging depth [97]. The larger beam sizes and pulse widths lead to lower out-of-focus peak intensities and two-photon signals. Finally, temporal focusing makes the excitation beam pattern (such as a line excitation pattern) resistant to scattering [104,105]. When projecting an excitation pattern through a turbid medium, scattering can cause speckle patterns and a degradation of the pattern. However, with temporal focusing, each spectral component of the pulse travels through a different portion of the tissue and acquires a different speckle pattern. The combination of different speckle patterns at the focus results in a smoothing effect that removes "hot spots" and recovers the desired excitation pattern.

Disclosed herein is a two-photon LEAD microscopy with a galvanometric mirror for scanning to reach 2,600 frames per second. When combined with an axial scanner, the microscope can potentially reach 30 volumes per second, which is hypothesized to be sufficient to resolve each calcium transient in the volume. Furthermore, since galvanometric mirrors are used in standard two-photon microscopes, the LEAD system can easily be implemented in these microscopes.

Also disclosed is an improved two-photon LEAD system using an acousto-optic deflector for scanning to reach up to 200,000 frames per second and >400 volumes per second. The system is capable of performing high-speed measurements, such as tracking the propagation of action potentials down axons, deconvolving calcium signals with near-millisecond precision, and resolving high frequency oscillations.

The system would also provide the first platform capable of taking advantage of the high speeds of voltage indicators for volumetric imaging.

FIGS. 24A-C schematically depict a two-photon LEAD microscope with scanning mirrors for brain imaging according to some embodiments of the present disclosure. Laser pulses are generated by a fiber laser, and the beam is scanned in the x-direction by a galvanometric mirror. A cylindrical scan lens focuses the laser pulses to a line, with a long axis in the y-direction, on the surface of a diffraction grating. The tube lens and objective image the scanning line to the sample. Emitted light is imaged to a 16-channel photomultiplier tube array. FIG. 24A shows the system in the yz-plane, showing the spatial dispersion of the pulse in the y-direction from the diffraction grating. The black dotted lines represent the propagation of a single spectral component of the pulse. FIG. 24B shows the system in the xz-plane, showing the beam focused in the x-direction on the diffraction grating, and scanned in the x-direction. FIG. 24C shows the diffraction grating in the xy-plane, showing a line that is scanned in the x-direction. The diffraction grating surface is imaged onto the sample.

Two-photon LEAD microscopy is built with a galvanometric mirror for scanning and the 16-channel photomultiplier tube array for detection to reach up to 2,600 frames per second. The first system is designed to excite a ~1×24 µm² (xxy, 1/e² diameter) line scanned over ~24 µm (x). Each PMT element detects signal from ~1/16th of the line. The goal of the galvanometric mirror scanning system is to inform the design of and assess the capabilities of an improved two-photon LEAD system with acousto-optic deflector scanning and more detector elements. For example, ensuring the desired field-of-view and resolutions are achieved, determining the collection efficiency of the system, and finding the pulse energies needed to reach a high signal-to-noise ratio. Furthermore, a computational model is developed and validated for its use in designing future systems.

An Er fiber laser (e.g., Raydiance Inc.) produces up to 7 µJ pulses at 303 kHz repetition rate with 1552 nm center wavelength. The laser is frequency doubled to $\lambda_0$=~776 nm center wavelength, with a bandwidth of $\Delta\lambda$=2.3±0.2 nm (FWHM). The 776 nm laser pulse width and shape were measured with an autocorrelator (e.g., APE PulseCheck), and were found to vary with the energy of the 1552 nm pulse. For low pulse energies, between 1.0-2.0 µJ the pulses were Gaussian in profile, with $\tau$=670±10 fs (FWHM). At an energy of 4.0 µJ, the pulses began to develop wings, and broaden to $\tau$=750±10 fs. For the highest pulse energy of 7.0 µJ, the pulses contained large wings with the center peak having $\tau$=1100±10 fs. The pulse width and shape dependence on pulse energy indicates the presence of nonlinear effects, such as self-phase modulation, or high-order dispersion. Furthermore, according to the pulse width—bandwidth relation, the pulse width should be ~380 fs, indicating the presence of some dispersion. However, the laser spectrum did not significantly vary with energy. Because of the pulse shape degradation at high pulse energies, experiments were generally limited to using ≤4.00 µJ 1552 nm pulses that were frequency doubled to 776 nm.

The laser is demagnified to a radius of 0.35 mm (1/e²) by a telescope, and is scanned in just the x-direction by a galvanometric mirror at 1,300 Hz. A 75 mm cylindrical scan lens focuses the beam to a line on a 1,200 lines/mm diffraction grating (e.g., 750 nm blaze, Thorlabs) for temporal focusing, or on a mirror for testing without temporal focusing. The diffraction grating is at ~69° with respect to the incident beam, such that the first-order diffracted beam is normal to the diffraction grating surface, according to the diffraction grating equation: $d(\sin\theta_i + \sin\theta_m) = On$ the grating or mirror, the laser beam forms a 60 µm thick line that is scanned in the x-direction. The angle of the diffraction grating results in a first-order diffracted line pattern that is longer than the line deflected by the mirror: the line deflected off the grating is 0.98 mm (1/e² radius) long (agreeing with the expected value of 0.35 mm/cos 69°), whereas the line deflected off the mirror is 0.35 mm long. The diffraction grating or mirror is imaged onto the sample by a 750 mm tube lens and 20×, 0.95 NA, water dipping objective (e.g., Olympus XLUMPlanFl). In this configuration, the diffraction grating provides temporal focusing, spatially dispersing and temporally stretching the laser pulse everywhere except at the focal plane. The large tube lens is necessary to spatially disperse the spectrum of the laser, which has a relatively small bandwidth. The excitation line on the grating or mirror is demagnified by a factor of $$M = 20 \times \frac{750 \text{ mm}}{180 \text{ mm}} = 83x,$$

since Olympus objectives are designed for a 180 mm tube lens and we use a 750 mm tube lens.

The two-photon signal emitted from the sample is collected by the same objective, deflected by a long-pass dichroic mirror, and imaged onto the 16-channel linear photomultiplier tube array (e.g., Hamamatsu H10515B-01). Two bandpass filters (e.g., 530/43 nm, Brightline) and a laser blocking filter (e.g., 700 nm cutoff shortpass, Thorlabs) are placed before the PMT array. An overall 667× magnification is required in the imaging path to image the ~24 µm (1/e² diameter) temporally-focused excitation line onto the 16 mm detector array. The objective and tube lens provide 83× magnification, and a 10× objective and 150 mm tube lens provide an additional 8× magnification for an overall 694×. Each element of the PMT (16×0.8 mm²) detects a 1.15 µm portion of the excitation line as it scans, with a 1.44 µm element center-to-center distance. The PMT signal is amplified and converted to voltage by a 1,500 V/A, 20 MHz preamplifier. The 16 channel data acquisition card records the signal at 100 MS/s per channel.

For some experiments, one channel of the data acquisition system was used to monitor the laser beam before entering the microscope to determine the relative magnitude of each pulse and the timing of each pulse. Before entering the microscope, a portion of the laser was deflected by a glass coverslip into a photodiode. The photodiode signal helped in data processing and image formation from the photomultiplier tube signals. The locations of the pulses in the PD signals indicated where the signal should be located in the PMT data. Furthermore, the PD data allowed us to account for slight pulse-to-pulse energy variations that lead to slight variations in two-photon signal levels.

Figure 25:
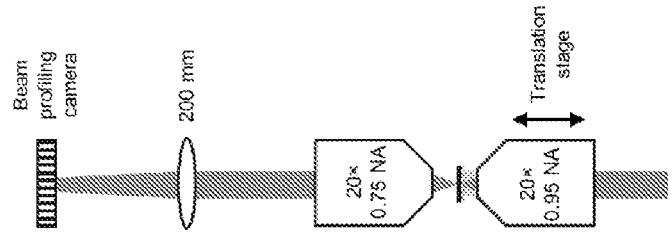
FIG. 25 schematically depict a beam profiling setup according to some embodiments of the present disclosure.

FIG. 25 schematically depict a beam profiling setup according to some embodiments of the present disclosure. A 20×, 0.75 NA objective lens and 200 mm image the focal plane (shown by the green dotted line) to a beam profiling camera. The excitation objective is translated so the imaging system profiles the laser beam throughout the sample volume. The beam sizes were measured throughout the focal volume using an additional imaging setup shown in FIG. 25. After the objective lens, a 4f setup imaged the excitation laser beam to a beam profiling camera. The 4f imaging system consists of a 20×, 0.75 NA objective (e.g., Nikon)

and a 200 mm tube lens. Because the excitation objective is water dipping and the imaging objective is an air objective corrected for a coverslip, a 170 μm coverslip with immersion medium was placed between the two objectives. The imaging objective was positioned such that the focal plane was just below the coverslip. The beam at that focal plane was imaged to the camera. The beam shape was profiled at different axial locations by translating the excitation objective along the optical axis and keeping the imaging setup stationary. The beam widths were extracted by fitting the image data to a 2D Gaussian:

$$I(x, y) = I_0 e^{-2\left[\frac{(x-x_0)^2}{w_x^2} + \frac{(y-y_0)^2}{w_y^2}\right]} + B, \qquad \text{Equation 1}$$

The beam sizes were also simulated in Zemax. The beam sizes throughout the focal volume were found using the Gaussian beam propagation tool in Zemax and placing "dummy" interfaces at the desired planes around the focal plane. The beam entering the system had a beam width of 0.35 mm ($1/e^2$ radius). At a given plane, the beam sizes for each wavelength were approximately the same, but the centers of the each beam in the y-direction were different because of the spatial dispersion introduced by the diffraction grating. The total beam was reformed by summing the beams of different wavelengths together, and weighting each by the magnitude in the laser spectrum. The beam width of the total beam was then calculated by fitting a 2D Gaussian profile.

Figure 26A:
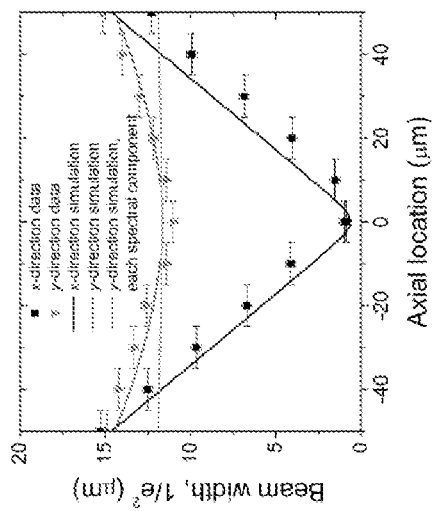
FIGS. 26A-D are graphs of experimental and simulated two-photon LEAD microscopy beam sizes throughout the focal volume for setups with and without temporal focusing according to some embodiments of the present disclosure.
Figure 26B:
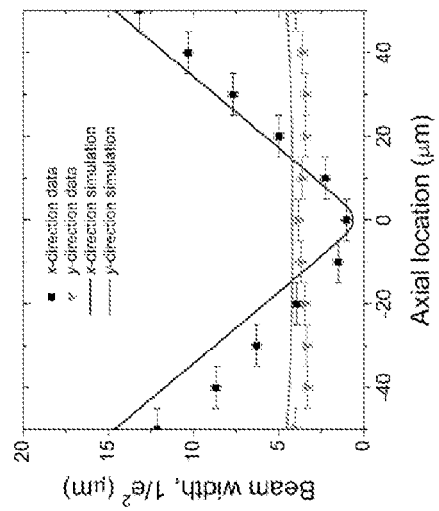

At the focal plane for the temporal focusing setup, the measured beam waists were 1.0±0.3 μm ($1/e^2$ radius, x-direction) and 11.1±0.3 μm ($1/e^2$ radius, y-direction) (Table 1, FIG. 26A-B). The length of the line closely matched both the designed and simulated beam lengths of 12 μm and 11.56 μm, respectively. However, the width of the line was slightly larger than the designed and simulated beam widths of 0.5 μm and 0.64 μm, respectively. The difference could result from aberrations, or is a measurement error as a consequence of the 5 μm uncertainty in positioning the objective translational stage.

TABLE 1

Experimental and simulated beam waist sizes for two-photon LEAD microscopy.

| | x-direction, $1/e^2$ radius (μm) | j-direction, $1/e^2$ radius (μm) |
|---|---|---|
| Temporal focusing setup, experimental | 1.0 ± 0.3 | 11.1 ± 0.3 |
| Temporal focusing setup, computational | 0.64 | 11.56 |
| Non temporal focusing setup, experimental | 1.0 ± 0.3 | 3.8 ± 0.3 |
| Non temporal focusing setup, computational | 0.64 | 4.23 |

The experimental beam profile throughout the entire focal volume did match simulations, indicating the beam is in fact focusing as designed. The presence of the temporally focused beam is confirmed by the high divergence of the beam in the y-direction, with respect to the length of the line. Each spectral component has low divergence, according to the simulations and Gaussian beam propagation. However, the spatial dispersion of each spectral component from temporal focusing causes the beam to focus with a higher apparent NA and a larger divergence. The larger out-of-focus beam widths, in addition to the longer out-of-focus pulse width, contributes towards higher axial resolution and a lower out-of-focus two-photon signal.

Figure 26C:
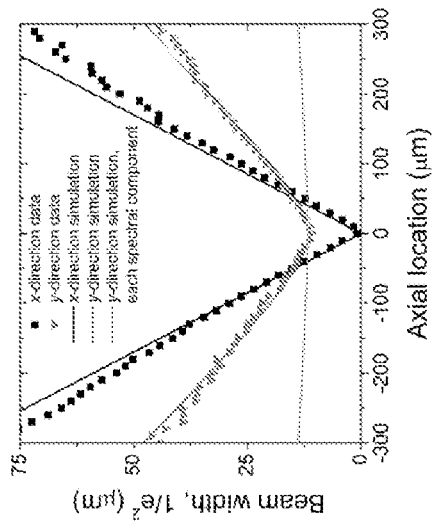
Figure 26D:
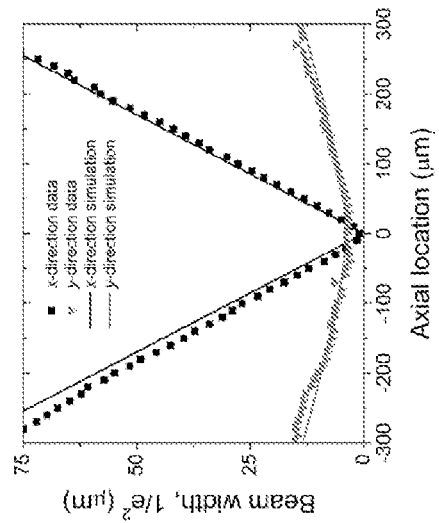

FIGS. 26A-D are graphs of experimental and simulated two-photon LEAD microscopy beam sizes throughout the focal volume for setups with and without temporal focusing according to some embodiments of the present disclosure. FIGS. 26A-B show graphs of the beam sizes for the setup with temporal focusing. The experimental and simulated beam sizes match along both axes. In the y-direction, the beam shows an overall divergence greater than the simulated divergence of each spectral component, as expected, because of temporal focusing. FIGS. 26C-D show graphs of the beam sizes for the setup without temporal focusing. FIGS. 26B and 26D are close-ups of FIGS. 26A and 26C, respectively, to highlight the beam waists. In each plot, positive axial locations indicate locations in between the focal plane and objective, with z=0 at the focal plane. Uncertainty in the experimental beam widths are ±0.3 μm, and uncertainty in the axial locations are ±5 μm.

At the focal plane for the setup without temporal focusing (replacing the diffraction grating with a mirror), the measured beam waists were 1.0±0.3 μm ($1/e^2$ radius, x-direction) and 3.8±0.3 μm ($1/e^2$ radius, y-direction) (Table 1, FIGS. 26C-D). Again, the length of the line nearly matched the designed and simulated beam lengths, while the width of the line was slightly larger. The length of the line is 2.9× smaller than in the temporal focusing setup because of the lack of diffraction grating. In the temporal focusing setup, the beam deflected off the grating is at a 69° angle with respect to the incident beam, resulting in a diffracted beam 1/cos(69°)=2.8× larger than the incident beam. As the diffraction grating or mirror are imaged onto the sample, the setup without temporal focusing should theoretically result in a line 2.8× shorter than the line in the temporal focusing setup. Throughout the focal volume, the experimental beam widths matched both the simulated beam widths and Gaussian beam propagation theory. Interestingly, the total beam divergence in the setup with temporal focusing is higher than the beam in the setup without temporal focusing, although each spectral component of the beam in the setup with temporal focusing has lower divergence. This allows longer lines to be created with temporal focusing with superior axial resolution and lower out-of-focus fluence.

The beam profiling setup was also used to measure the scanning field-of-view. Two different settings were used, with FOVs of 17.9±0.3 μm or 27.1±0.3 μm, by changing the angular scanning range of the scanning mirror. The intensity profile of the scanned beam on the beam profiling camera also provided information on the dwell time of the beam at each location within the FOV. The dwell time was constant in the middle of the FOV, indicating a constant scanning velocity, but was longer at the edges of the FOV as the scanning mirror reversed direction. The distance scanned between consecutive pulses throughout the FOV was approximated from the FOV size, intensity profile on the camera, frame rate, and pulse repetition rate. The distance between pulses in the middle of the FOV is 0.17±0.01 μm for the smaller FOV, and 0.26±0.01 μm for the larger FOV. The larger FOV was primarily used since the portion of the FOV with a constant scanning velocity nearly matches the demagnified width of each PMT element of 23 μm. Additionally, given the ~1 μm width of the line, the faster scanning for the larger FOV excites each point in the sample with only a few pulses. Therefore, the system more closely resembles the improved two-photon LEAD system with fast acousto-optic scanning and only a few pulses per point.

Figure 27B:
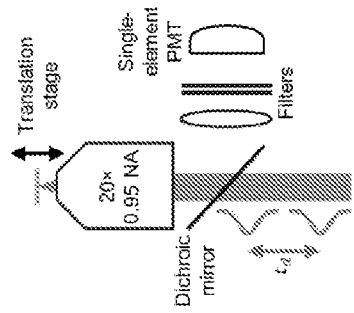
FIGS. 27A-B schematically depict a pulse width measurement setup according to some embodiments of the present disclosure.
Figure 27A:
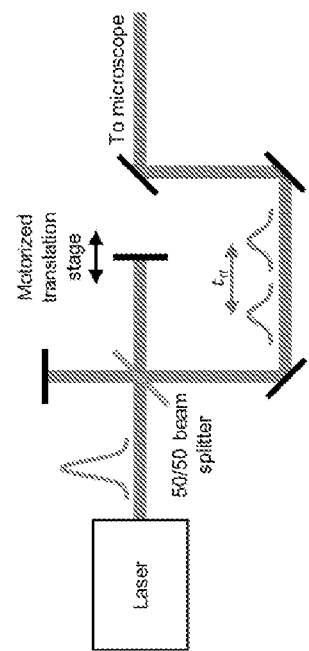

FIGS. 27A-B schematically depict a pulse width measurement setup according to some embodiments of the present disclosure. FIG. 27A shows the laser pulses enter a Michelson interferometer, with one arm able to change its path length to introduce a time delay to the recombined laser pulses. FIG. 27B shows the interfered laser pulses excite fluorescence from a thin layer of fluorescein, which is collected by a single-element PMT. The layer of fluorescein is translated axially to measure pulse width at different axial locations.

Temporal focusing causes the pulse width to vary as a function of axial location. When the spectral components of the pulse are spatially dispersed, the local bandwidth is reduced, the phase relationship between spectral components of the pulse is disrupted, and the pulse width is increased. At the focus where the spectral components come back together, the pulse width is at its shortest. Since the pulse width can vary on the order of microns, commercial pulse width measurement systems cannot be used.

The pulse width throughout the focal volume was measured using second-order autocorrelation [100,107]. A Michelson interferometer was constructed and placed before the two-photon LEAD microscope (FIG. 27A). The incoming laser beam was split by a 50/50 ultrafast beamsplitter into two arms, reflected back by a mirror in each arm, and recombined by the beamsplitter. The mirror on one arm of the interferometer was placed on a linear motorized stage that can translate several mm at up to 2 mm/s. A thin layer of fluorescein after the objective provides second-order contrast and axial resolution for the pulse width measurement. The samples were prepared by depositing 1-20 µL 1 mM fluorescein onto a large 170 µm thick coverslip and placing another 170 µm coverslip on top of the fluorescein. With the top coverslip having dimensions of 18×18 mm$^2$, the evenly spread fluorescein layers had average thicknesses of 3-60 µm. The thinnest samples were used for measurements around the focus, while the thickest samples were only used far from the focus to increase the signal level. To maximize the collected signal, a single-element PMT was used rather than the PMT array. The dichroic mirror was placed at the objective back aperture, and a lens focused the collected light onto the PMT. We used the 776 nm, τ=750±10 fs pulses generated by the 4 µJ, 1552 nm pulses because they have a relatively clean beam profile with small wings.

The measurement was performed by collecting two-photon signal from the stationary fluorescein layer as the translation stage with the mirror moved to interfere the two laser beams. For a given time delay ($t_d$) between the two interferometer arms, the two-photon signal is the sum of the two beam's electric fields to the fourth order:

$$S(t_d) = \int_{-\infty}^{\infty} dt[(E(t)+E(t-t_d))^2]^2, \quad \text{Equation 2}$$

The resulting normalized second-order autocorrelation signals vary in magnitude from 0 to 8, where a value of 0.5 is the signal from a single pulse. For large delays between pulses when there is no interference, the signal from both pulses added together is 2× higher than from a single pulse. At maximum constructive interference, the pulse intensity is 4× higher than a single pulse, and the two-photon signal is 16× higher. At maximum destructive interference, the signal is 0. To extract the pulse width, the second-order autocorrelation signal was filtered with a mean filter of width 5 fs, and fit to a Gaussian. The pulse width was recovered using the relation: $\sqrt{2}\tau_{pulse} = \tau_{autocorrelation}$. The fluorescein layer was then moved to different z-locations throughout the focal volume, and the measurement was repeated.

The pulse width as a function of axial location was also simulated, following a Fresnel propagation method [108]. First, the sizes ($w_y$), locations ($y_0(\lambda)$), and phases ($\varphi(y,\lambda)$) of the beams from the different wavelengths were calculated at the objective lens with Zemax, and the initial electric fields were initialized:

$$u_0(y,\lambda) = \sqrt{S_0(\lambda)} e^{-(y-y_0(\lambda))^2/w_y^2} e^{i\varphi(y,\lambda)}, \quad \text{Equation 3}$$

The electric fields were weighted by their magnitude in the laser spectrum, $S_0(\lambda)$. Next, a quadratic phase was applied across the beam from the objective lens:

$$u_{obj}(y,\lambda) = u_0(y,\lambda) e^{-iky^2/2f} \quad \text{Equation 4}$$

Here, f=2.0 mm is the objective's working distance, and k=2π/λ is the wavevector. The beam was propagated forward a distance z'=f−z (z=0 at the focal plane) from the objective in the Fourier domain by Fresnel diffraction:

$$u(y,z',\lambda) = \mathcal{F}^{-1}\{\mathcal{F}[u_{obj}(y,\lambda)] \times H\} \quad \text{Equation 5}$$

$$H = \mathcal{F}\{h(y,z',\lambda)\} = \mathcal{F}\left\{\frac{e^{ikz'}}{i\lambda z'} e^{i\frac{ky^2}{2z'}}\right\} \quad \text{Equation 6}$$

where $\mathcal{F}$ is the Fourier transform, and H is the Fresnel diffraction kernel. Finally, the spectra (S) and pulse shapes (P) were found at each axial location at y=0:

$$S(z',\lambda) = u(y=0,z',\lambda) \times u^*(y=0,z',\lambda) \quad \text{Equation 7}$$

$$P(z',t) = \mathcal{F}\{u(y=0,z',\lambda)\} \times (\mathcal{F}\{u(y=0,z',\lambda)\})^* \quad \text{Equation 8}$$

The spectra FWHMs and pulse width FWHMs are then calculated from S and P. For the theoretical pulse width in the setup without temporal focusing, the measured pulse width of the beam before the microscope of 750 fs is used, rather than the transform-limited pulse width of 380 fs, because we did not account for linear or higher-order dispersion in the simulation.

The experimentally measured autocorrelations had a contrast ratio of 8:1, showing complete interference of the two beams from the interferometer. The pulse shape did show small wings, similar to those found on the commercial autocorrelator. For the setup with temporal focusing, pulse stretching away from the focus was observed. At the focal plane, the pulse width reached a minimum of 850±150 fs, longer than the transform-limited pulse width. Although temporal focusing has been shown to reach the transform-limited pulse width around the focal plane, the presence of high-order dispersion can severely distort the pulse shape at the focal plane. Away from the focal plane, the pulse width stretched to >2.5 µs, showing a pulse stretching factor of ~3-4×. The setup without temporal focusing did not show pulse stretching, with a pulse width of 810±50 fs throughout the focal volume. Aside from the temporally-focused beam not reaching the transform-limited pulse width at the focus, the experimental data matched the computational model and an analytical model [108].

Figure 28B:
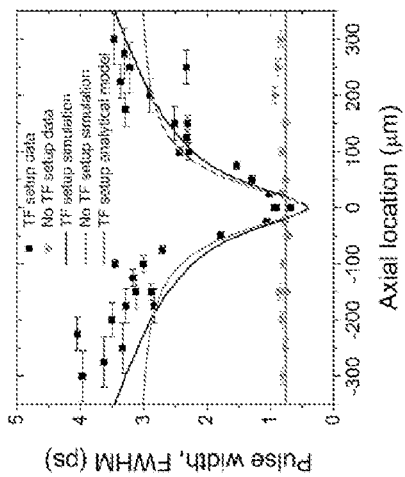
FIGS. 28A-B are graphs of pulse widths throughout the focal volume according to some embodiments of the present disclosure.
Figure 28A:
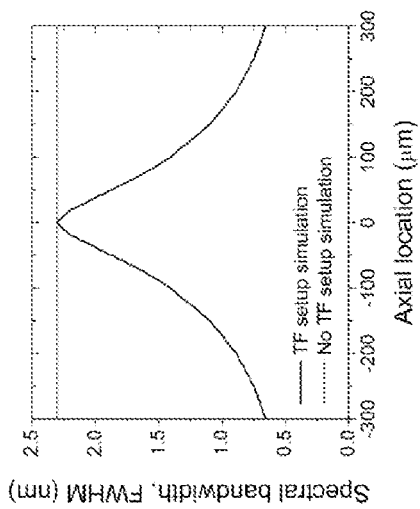

FIGS. 28A-B are graphs of pulse widths throughout the focal volume according to some embodiments of the present disclosure. FIG. 28A shows the simulated spectral bandwidth at y=0 as a function of axial location. With temporal focusing, the full bandwidth is recovered only at the focal plane. FIG. 28B shows the experimental and simulated pulse widths as a function of axial location. The pulse width measurements were made by second-order autocorrelation.

Uncertainty in axial location is caused by the thickness of the fluorescein sample and the uncertainty in stage position.

FIGS. 29A-D are graphs of raw data and images from imaging a 0.5 μm diameter fluorescent bead according to some embodiments of the present disclosure. The FOV is 17.9×22.2 μm² (xxy), and the presented data is for the best focal plane of the bead. FIG. 29A shows PMT signals from ~52 frames (~26 scanning mirror cycles) acquired in 20 ms. A fluorescent bead is apparent in the signal from PMT #9. The data shows a signal-to-background ratio >80. FIG. 29B shows a zoomed-in portion of FIG. 29A, showing just two frames and one mirror scanning cycle. The dotted line separates the two frames, with the mirror scanning in the positive x-direction to the left of the dotted line, and the negative x-direction to the right of the dotted line. FIG. 29C shows an image of the 0.5 μm diameter bead, averaged across 10 frames in FIG. 29A. FIG. 29D shows an image of the same bead, from just the right frame in FIG. 29B.

Figure 30A:
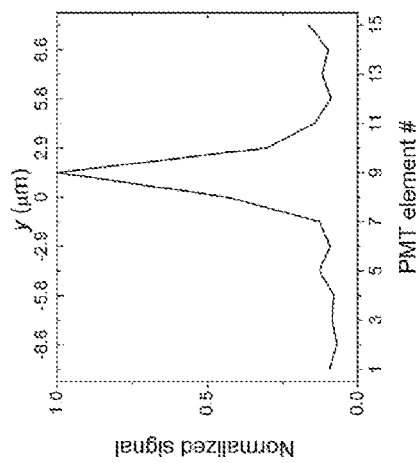
FIGS. 30A-C are graphs of normalized two-photon signal profiles from averaging 10 frames of the 0.5 µm diameter fluorescent bead of FIGS. 29A-D according to some embodiments of the present disclosure.
Figure 30B:
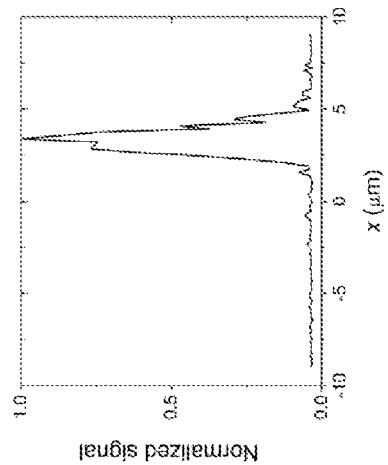
Figure 30C:
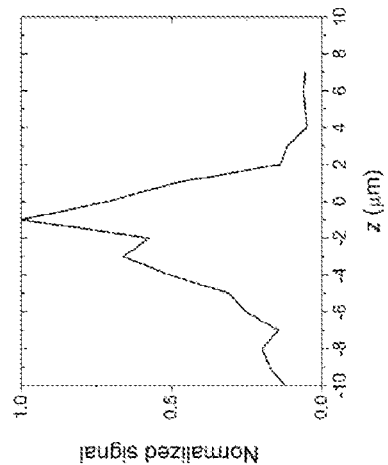

FIGS. 30A-C are graphs of normalized two-photon signal profiles from averaging 10 frames of the 0.5 μm diameter fluorescent bead of FIGS. 29A-D according to some embodiments of the present disclosure. FIG. 30A shows the width of the bead in the x-direction is 1.3±0.3 μm (FWHM). FIG. 30B shows the width of the bead in the y-direction is less than 1.44 μm (FWHM), which is the PMT element center-to-center separation. FIG. 30C shows the width of the bead in the z-direction is 5.0±1.4 μm (FWHM).

The resolution of the two-photon LEAD system with temporal focusing was measured by imaging fluorescent beads. Transparent phantoms were created by embedding 0.5 μm diameter fluorescent beads in agar. The galvanometric mirror was scanned at 1,300 Hz to give 2,600 frames per second, over the smaller FOV of 17.9±0.3 μm. Two-photon signal was imaged by 15 PMT channels. One data acquisition channel was used to record the signal from a portion of the laser beam deflected onto a photodiode, to help indicate when laser pulses should generate signal. The phantom was mounted on a piezo stage, and several frames were collected for each axial plane separated by 1.0 μm. The laser power was 4.2 mW at the sample.

The raw PMT data obtained from imaging the beads shows the high speed and high detection sensitivity of the two-photon LEAD microscope (FIGS. 29A-B). Imaging one bead shows a signal-to-background ratio >80, calculated as SBR=max(signal)/$\mu_{background}$. The SBR can be further improved with higher laser power. Just a single frame without averaging provides a clear image of the bead (FIGS. 29B and 29D). Averages of 10 frames shows the PSF obtained from the bead. The bead in FIG. 29C has a measured width in the x-direction (the scanning direction) of 1.3±0.3 μm (FWHM), with uncertainty from the distance between two consecutive pulses (FIG. 30A). The bead in the y-direction (the direction of the excitation line long axis) can only be resolved by the larger of the demagnified PMT element-to-element distance and the objective's imaging resolution. With the 0.95 NA water immersion objective, the expected imaging resolution is smaller than the demagnified PMT element-to-element separation of 1.44 μm. The example bead image shows the signal mostly confined to PMT element #9, with some signal on adjacent PMT elements (FIG. 30B). The measured bead width in the z-direction is 5.0±1.4 μm (FWHM), with uncertainty arising from the 1.0 μm increments between axial planes (FIG. 30C).

The system's resolution is determined by averaging the widths obtained from several beads. The resolution in the x-direction is 1.1±0.2 μm (FWHM), slightly smaller than the measured beam width of 1.2±0.3 μm (FWHM), as expected for two-photon microscopy. Once again, the beads had the majority of their signal confined to a single PMT element, making the resolution in the y-direction limited by the demagnified PMT element-to-element separation. The resolution in the z-direction is 5.4±0.6 μm (FWHM), larger than standard two-photon point-scanning systems. The axial resolution can be further improved in the current setup by spatially dispersing the laser pulse fully onto the back aperture of the objective using a diffraction grating with a higher density of grooves or a tube lens with a longer focal length.

The axial sectioning capabilities and out-of-focus two-photon signals of the system were further determined by measuring the two-photon signal from a thin layer of fluorescein as a function of axial location. The thin layer of fluorescein was prepared the same way as the pulse width measurement experiments, but using just 1 μL fluorescein to form a ~3 μm thick layer. The fluorescein layer was translated axially, and all emitted light was collected onto a single-element PMT to determine the signal level from at each axial plane and to calculate axial sectioning. The PMT signal at each axial location was normalized to the photodiode signal squared, to account for changes in laser power.

The axial sectioning and out-of-focus two-photon signals were also modeled using the computational simulation. The number of signal photons detected from one pulse exciting a thin layer ($\Delta z$) of dye with area A (in x and y) is approximated by:

$$N(z) = q\eta\phi_f C_f \Delta z \sigma_{2p} \int_A dA \int_{-\infty}^{\infty} dt\, I(x, y, t, z)^2 \quad \text{Equation 9}$$

where q=0.15 is the quantum efficiency of the detector at the detected wavelength, η is the collection efficiency of the system, ϕ=0.93 is the quantum yield of fluorescein [77], $C_f$ is the concentration of fluorescein, $\Delta z$ is the thickness of the fluorescein layer, $\sigma_{2p}$=40×10⁻⁵⁸ m⁴ s/photon is the two-photon excitation cross-section of fluorescein at 776 nm [109], and I(x, y, t, z) is the laser intensity. The intensity is modeled as:

$$I(x, y, t, z) = I_0(z) e^{-2\left(\frac{x^2}{w(z)_x^2} + \frac{y^2}{w(z)_y^2}\right)} e^{-4ln2\left(\frac{t^2}{\tau(z)_{FWHM}^2}\right)} \quad \text{Equation 10}$$

where $w_x(z)$ and $w_y(z)$ are the beam widths and $\tau_{FWHM}(z)$ is the laser pulse width. The peak intensity depends upon the power at the sample (P), laser repetition rate (f), photon energy (hc/λ), laser pulse width as a function of axial location, and beam area as a function of axial location:

$$I_0(z) = \frac{P\lambda}{fhc} \frac{2}{\pi w(z)_x w(z)_y} \frac{2\sqrt{ln2}}{\sqrt{\pi}\, \tau(z)_{FWHM}} \quad \text{Equation 11}$$

For an infinitely large plane of a thin layer of dye, Eq. 9 can be reduced to:

$$\frac{N(z)}{N(z=0)} = \frac{w_x(z=0)w_y(z=0)\tau(z=0)_{FWHM}}{w_x(z)w_y(z)\tau(z)_{FWHM}} \quad \text{Equation 12}$$

after normalizing the two-photon signal to the peak signal at z=0. The simulated beam areas and pulse widths were used to model the normalized two-photon signal as a function of axial location.

Figure 31A:
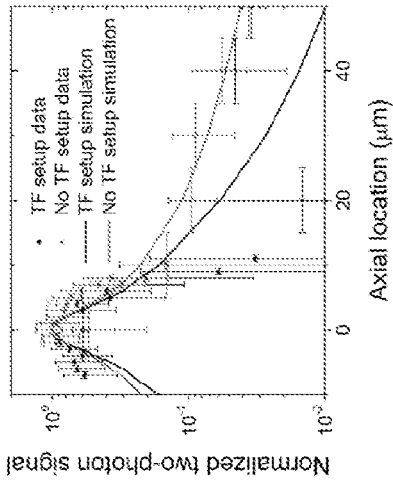
FIGS. 31A-B are graphs of normalized two-photon signal as a function of axial location according to some embodiments of the present disclosure.
Figure 31B:
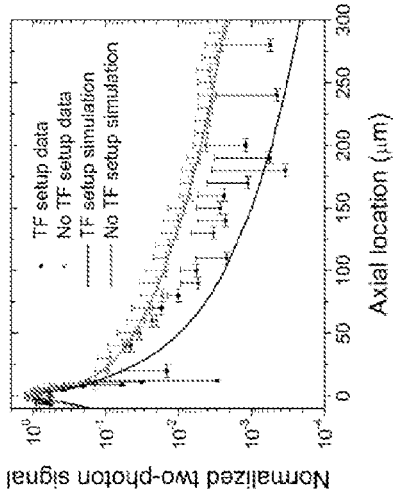

FIGS. 31A-B are graphs of normalized two-photon signal as a function of axial location according to some embodiments of the present disclosure. Fluorescence from a thin layer of fluorescein was collected by a single PMT. The fluorescein layer was translated to different axial locations. Temporal focusing provides better axial sectioning and generates lower out-of-focus background signal. FIG. 31B is a zoom-in of FIG. 31A. Data are mean±standard deviation of the collected signals, normalized to the input laser power, and then normalized to the signal collected when the fluorescein layer is at the focal plane. Negative uncertainty in the normalized two-photon signal is not shown in FIG. 31A for clarity.

For the setup with temporal focusing, the measured and simulated two-photon fluorescence signal from the thin layer of fluorescein has an axial FWHM of 9.0±0.7 μm and 8.0±0.7 μm, respectively (FIG. 31A-B). The setup without temporal focusing has experimental and simulated axial FWHMs of 13.0±0.7 μm and 8.0±0.7 μm, respectively. The discrepancy in the results from the setup without temporal focusing is likely from the slightly broadened beam profile in the y-direction beam profile around the focus, as seen in FIG. 26D. For both setups, the two-photon signal degraded rapidly away from the focal plane, with the experimental and simulated results in agreement. At 300 μm away from the focal plane, the setup with temporal focusing generates ~4× less two-photon signal because of the increased out-of-focus pulse width and beam size in the y-direction.

Notably, the axial profile from the thin layer of fluorescein is wider than the z-direction resolution obtained from imaging beads. The fluorescein signal depends on the signal generated over the full x-y plane, while the bead signal depends on just the signal generated over the bead area, and is approximated from the peak intensity squared and pulse width: $N_{bead}(z) \propto I_0(z)^2 \tau(z)$. While imaging beads is more appropriate for measuring resolution, the signal generated by fluorescein provides additional information on out-of-focus fluorescence.

Figure 32:
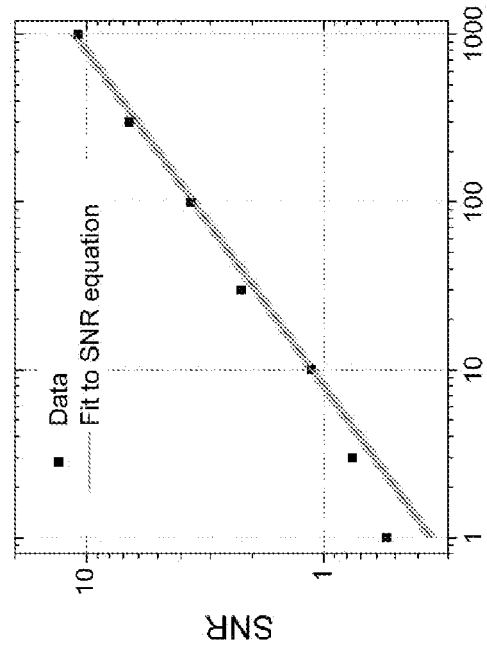
FIG. 32 is a graph of signal-to-noise ratios of the two-photon LEAD microscope for different concentrations of fluorescein according to some embodiments of the present disclosure.

FIG. 32 is a graph of signal-to-noise ratios of the two-photon LEAD microscope for different concentrations of fluorescein according to some embodiments of the present disclosure. The gray bar surrounding the fitted line indicates the 95% confidence interval for the fitted line.

The collection efficiency and detection sensitivity of the two-photon LEAD system with temporal focusing was determined by measuring the signal-to-noise ratio of different fluorescein concentrations flowing in the microfluidic device from the one-photon LEAD cytometer. The highest energy pulses were used, with τ=1100±10 fs before entering the microscope. Fluorescence was imaged onto the 16 channel PMT array. A 2 channel, high-speed, 1 GS/s data acquisition card was used, rather than the 16 channel, 100 MS/s card, to capture the peak of each signal pulse with 1 ns resolution. One channel collected the signal from the photodiode sampling the laser before the microscope to correct for pulse energy fluctuations, while the other channel collected the signal from the center PMT element.

The signal-to-noise ratio is calculated as:

$$SNR = \frac{\mu_{signal}}{\sigma_{signal}} = \frac{N_1}{\sqrt{F_e N_1}} \quad \text{Equation 13}$$

where $\mu_{signal}$ and $\sigma_{signal}$ are the average and standard deviation of the signal generated by each pulse, $F_e$=1.33 is the noise factor for the PMT, and $N_1$ is the number of photons detected by the center PMT element in the linear PMT array. $N_1$ is estimated by Eq. 9, but the area integral is taken over the demagnified PMT element size. Additionally, Δz=5.4 μm is the measured axial resolution, $w_x$=1.0 and $w_y$=11.1 are the measured beam widths at the focal plane, τ=1.09 μs is the pulse width at the focal plane measured by second-order autocorrelation, P=4.2 mW, and $C_f$ are the tested concentrations of fluorescein. Only multiplicative noise and shot noise are considered, since dark current and other noise are negligible compared to the signal at the peak of the pulse. The SNR data for different concentrations of fluorescein are fit to the equation, and the collection efficiency of the optics (η) and detection sensitivity ($C_f$ at SNR=1) are found.

Similar to one-photon LEAD microscopy, the log(SNR) vs log($C_f$) data fits a line with slope 0.487±0.060, indicating the system is nearly shot noise limited (slope of 0.5) and Eq. 13 is valid (FIG. 32). Fitting Eq. 13 to the SNR data, the measured collection efficiency is η=2.6±0.3%. The expected collection efficiency is higher, considering the 0.95 NA water dipping objective collects ~15% of emitted photons. Our measured collection efficiency would indicate that the objective and remaining optics transmit ~20% of light. However, the large wings of the pulse contain a significant portion of the total pulse energy, causing the peak intensity to be lower than expected for a perfectly shaped, 1.09 ps pulse. As the number of photons emitted scales with the peak intensity squared, even small deformations in pulse shape can significantly lower the number of photons emitted. The low apparent collection efficiency may also be a result of the circuit after the PMT. The 20 MHz preamplifier is slow compared to the fluorescence lifetime. A faster preamplifier or a photon counting circuit could bring signal levels to expected values. Therefore, considering the pulse shape and detection circuit, the actual collection efficiency is likely higher than 2.6%.

The detection limit when SNR=1 is $C_f$=8.0±0.8 μM fluorescein, or 30,000±3,000 molecules in a $w_x$×demagnified PMT element size×Δz volume. The system has about half the collection efficiency as the one-photon LEAD microscope and has a detection limit ~70× higher in terms of number of molecules in the volume detected by a PMT element. The difference in the detection limit is partially a result of the nature of two-photon absorption, the low power of the pulsed laser (providing just 14 nJ pulses at the sample), and the poor pulse shape.

Figures 33A, 33B:
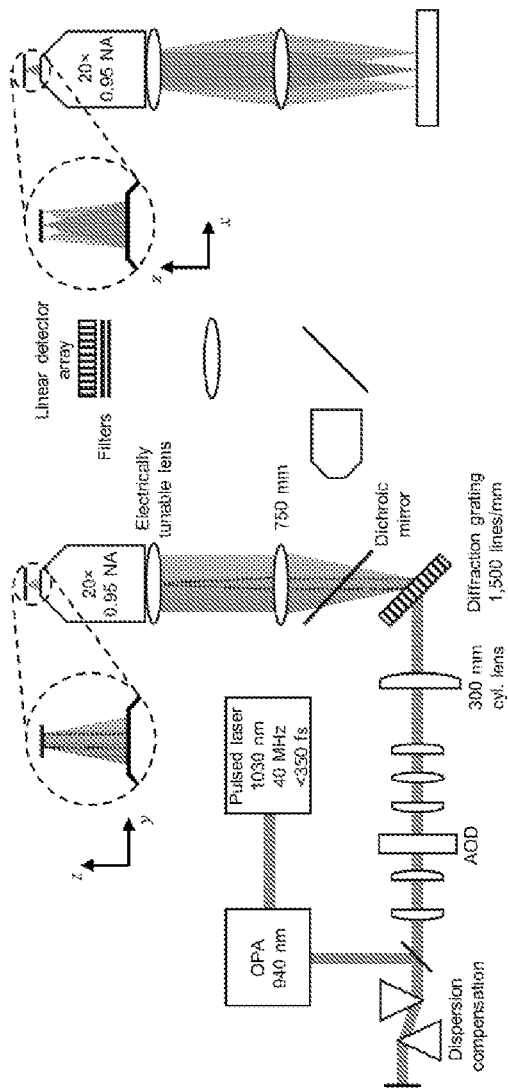
FIGS. 33A-B schematically depict a two-photon LEAD microscope with an acousto-optic deflector for scanning according to some embodiments of the present disclosure.

FIGS. 33A-B schematically depict an improved two-photon LEAD microscope with an acousto-optic deflector for scanning according to some embodiments of the present disclosure. Laser pulses are generated by a high-power, high repetition rate fiber laser at 1030 nm central wavelength. The central wavelength is converted to 940 nm by an OPA to excite the genetically encoded calcium indicator GCaMP6f at its peak. Two cylindrical lenses shrink the beam along one axis to fit the aperture of the AOD scanner. The AOD scans the beam rapidly in the x-direction. A set of lenses provide any needed magnification and correct for the cylindrical lens effect of the AOD. A cylindrical scan lens focuses the laser pulses to a line on the surface of a diffraction grating, with a long axis in the y-direction. The tube lens and objective image the scanning line to the sample. The diffraction grating provides temporal focusing. Emitted light is imaged to a 32-channel detector array. FIG. 33A shows the system in the yz-plane, showing the spatial dispersion of the pulse in the y-direction from the diffraction grating. The black dotted lines represent the propagation of a single spectral component of the pulse. FIG. 33B shows the system in the xz-plane, showing the beam focused in the x-direction on the diffraction grating, and scanned in the x-direction.

The two-photon LEAD microscope with acousto-optic deflector scanning has components similar to the current two-photon LEAD microscope with scanning mirrors: a scan lens, a diffraction grating, a tube lens, and an objective lens (FIGS. 33A-B). Again, the diffraction grating is imaged onto the sample for temporal focusing. The microscope is flexible in design where parameters including scanning field-of-view, the length and width of the excitation line, axial resolution, and frame rate can be obtained by proper selection of free parameters such as scan lens, tube lens, objective, diffraction grating, and input beam sizes.

The design of the microscope in the scanning direction (x-direction) is similar to one-photon LEAD microscopy. The desired FOV and excitation line width at the sample ($w_x$) define the number of resolvable points needed from the AOD. Since two-photon resolution is smaller than the excitation beam width, care should be taken to choose a larger number of resolvable points for proper sampling. From the number of resolvable points, the beam size at the AOD aperture ($w_{x,AOD}$) can be calculated from:

$$N = \Delta f \frac{2w_{x,AOD}}{v_a}\left(1 - FPS\frac{2w_{x,AOD}}{v_a}\right) \quad \text{Equation 14}$$

Here, $\Delta f$ is the bandwidth of the AOD, $v_a$ is the acoustic velocity of the AOD crystal, and FPS is the desired frame rate. The full angular scan range of the AOD is approximately $$\Delta\Theta = \Delta f \frac{\lambda_0}{v_a}\left(1 - FPS\frac{2w_{x,AOD}}{v_a}\right) \quad \text{Equation 15}$$

where $\lambda_0$ is the laser central wavelength). After magnification optics (with magnification $M_x$) followed by a cylindrical scan lens (with focal length $f_s$) between the AOD and grating, the linear scanning range is $FOV_{grating}=\Delta\Theta f_s/M_x$. For the AOD to scan the beam over the desired FOV, the linear scanning range on the grating must be $FOV_{grating}=FOV\times M$, where M is the overall magnification provided by the objective and tube lens. With an objective with magnification $M_o$ and a tube lens of focal length $f_t$, $$M = M_o \frac{f_t}{f_{t,o}}$$

where $f_{t,o}$ is the tube lens that the objective is designed for. The $FOV_{grating}$ equality condition can be met by the selection of a tube lens, which depends on the microscope's y-direction design.

The desired length of the excitation line ($w_y$) and bandwidth of the laser ($\Delta\lambda$) largely inform the design of the microscope in the y-direction. The y-direction includes temporal focusing. With the grating imaged onto the sample, the length of the excitation line diffracted off the grating must be $w_{y,grating}=w_y M$. The size of the beam incident on the grating ($w_{y,in}$) and the angle of the grating can then be selected to fulfill: $w_{y,grating}=\cos\theta_{d,0}/\cos\theta_i$, where $\theta_{d,0}$ is the angle of the first order diffracted beam for the center wavelength, given an incident angle of $\theta_i$ (angles relative to the grating normal). Magnification optics (with magnification $M_y$) can also be placed between the AOD and grating such that $w_{y,in} w_{y,AOD}M_y$. Off of the grating, the full angular range of the spectrum is defined by the diffraction grating equation:

$$\Delta\Theta_{\Delta\lambda}=\sin^{-1}[k_g(\lambda_0+\Delta\lambda)-\sin\theta_i]-\theta_{d,0} \quad \text{Equation 16}$$

The necessary tube lens focal length is then found by linearly dispersing the spectrum of the laser on the full back aperture diameter of the objective lens: $\Delta\Theta_{\Delta\lambda}f_t=d_o$ [110]. If a tube lens of that focal length cannot be found, the magnification optics $M_y$ or diffraction grating angle can be changed to allow the use of available tube lenses. With the tube lens defined, the scanning lens focal length and magnification optics in the x-direction can be determined. Notably, the beam size out of the AOD should not exceed the AOD aperture, and the beam size at the objective should not be larger than the back aperture.

Following the above considerations, the improved two-photon LEAD system with AOD scanning was designed for mouse brain imaging. The microscope is designed to excite a 1×64 µm² (1/e² diameter) line that is scanned over a 150 µm FOV at 200,000 frames per second. At such high speed, only a single pulse excites any given spot in the sample per frame, which also maximizes SNR for a given laser power [49]. The addition of axial scanning allows imaging of hundreds of volumes per second, which is fast enough to capture the calcium transients in each neuron in the volume. The high speed also provides a platform for high-speed voltage indicators [94,95].

A high-powered pulsed laser generating ~250 fs pulses at high repetition rates is converted to a center wavelength of 940 nm with an optical parametric amplifier (OPA) to excite the fast, genetically encoded calcium indicator GCaMP6f at its peak [6]. A high bandwidth ($\Delta f$=200 MHz), large aperture (9 mm), longitudinal AOD driven by a chirped frequency at 200 kHz scans the laser beam (e.g., Brimrose TED-320-200). The necessary number of resolvable points (150) are reached with a beam size of $w_{x,AOD}$=2.0 mm entering the AOD. The beam size in the y-direction after the AOD and magnification is $w_{y,in}$=2.7 mm. Magnification optics ($M_x$=0.86) and a 300 mm cylindrical scan lens shape the beam to a line that is scanned over 12.5 mm on a diffraction grating. The diffraction grating with $k_g$=1,500 lines per mm is angled at 44.8°. A transmission grating is used to maximize laser transmission through the system. The first-order diffracted beam is then imaged onto the sample by a 750 mm achromatic tube lens and the 20×, 0.95 NA objective lens used in the current two-photon LEAD microscope. The laser repetition rate will be set to keep up with the high rate of resolvable points during the scanning period (≥33 MHz). A dispersion compensation system is added to correct for any dispersion that the AOD and other optical elements may introduce to the laser pulses, and produce a transform-limited pulse at the focal plane.

Figure 34:
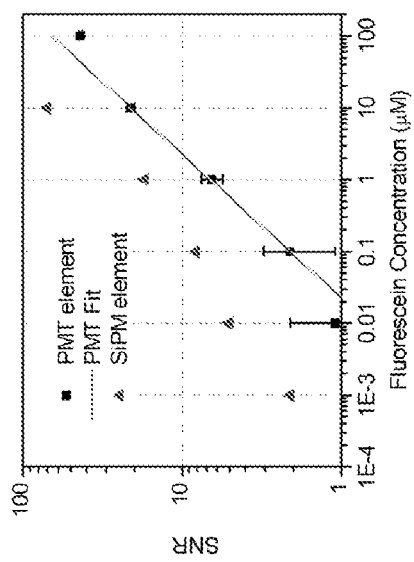
FIG. 34 is a graph of signal-to-noise ratios for a silicon photomultiplier element detecting fluorescein emission in the one-photon LEAD cytometer setup according to some embodiments of the present disclosure.

FIG. 34 is a graph of signal-to-noise ratios for a silicon photomultiplier element detecting fluorescein emission in the one-photon LEAD cytometer setup according to some embodiments of the present disclosure.

Two-photon emission is imaged onto either a 32-channel PMT array or a 32-channel silicon photomultiplier (SiPM) array, with each element detecting a 2 µm section of the excitation line. Silicon photomultipliers are available in large linear arrays, and were tested to determine their sensitivity in comparison to PMTs. With the one-photon LEAD cytometer setup, we performed an SNR analysis identical to the 16-channel PMT analysis. Different concentrations of fluorescein flowing in the microfluidic device were excited, and all fluorescence was detected by a single SiPM element. The single SiPM element displayed ~4× higher SNR for a given concentration compared to a single PMT element (FIG. 34). Considering ~16× more photons are incident on the SiPM element, and assuming the detector is shot noise limited (SNR $\propto \sqrt{N_{photons}}$), the sensitivity of the SiPM is comparable to the PMT array. Therefore, either detector is practical for the high-speed two-photon LEAD microscope, but SiPMs may provide more upward scalability with the availability of larger arrays.

Volumetric imaging can be performed by adding an axial scanning system. The ideal axial scanning system must scan hundreds of microns at hundreds of Hz, and be capable of imaging emitted light onto the detector array. Several axial scanning systems exist, with different speeds, scanning ranges, and complexities. Among these are a piezo to rapidly vibrate the objective axially [37,111], an electrically tunable lens with variable focal length [112-115], additional AODs to form an acousto-optic lens [116,117], remote scanning [118,119], and introducing second-order dispersion to the pulses entering the microscope [102]. Second-order dispersion in a temporal focusing setup essentially acts as a cylindrical lens along the temporal focusing direction. However, the concept is not practical for line-scanning temporal focusing, since there is no effect along the spatially focused dimension. In remote scanning, a fast, axially scanning mirror is imaged onto the sample. However, remote scanning setups typically incorporate an additional tube lens and objective, which can drastically reduce transmission of emitted light through the system and lower SNR. An acousto-optic lens would be able to scan the excitation beam quickly, but would not be practical to descan emitted light. Therefore, the emitted light generated when scanning away from the natural focal plane would be blurred on the detector array.

Piezos and electrically tunable lenses are the most practical solution for axial scanning, as they can scan over hundreds of microns at hundreds of Hz, can descan emitted signal, and are relatively simple to implement. Current piezo stages for objectives can reach 200 Hz, providing 400 frames per second, while traveling 100 μm. Faster piezo stages up to nearly 500 Hz have a limited range of 40 μm. Current ETLs also scan up to 200 Hz, with a larger scanning range than piezos. The scanning rate of ETLs can potentially be increased when the ETL is driven at resonance (600 Hz), at the cost of the usable aperture of the ETL.

While the system meets the resolution and scanning range requirements for high-speed two-photon imaging of the mouse brain, the signal-to-noise ratio when performing such fast imaging must be high enough to resolve weak signals from calcium indicators, or from voltage indicators. The expected SNR can be estimated based upon the SNR equation (Eq. 13). For the calculations, we assume a higher detector quantum efficiency (GaAsP PMTs have q=0.4) and collection efficiency (η=7.5%) than the current system. The laser excites a sample labeled with 5 μM GCaMP6f with a $\sigma_{2p}=35 \times 10^{-58}$ m$^4$ s/photon and ϕ=0.6 [6]. A single PMT element then detects signal generated from a ~1.4×2×1 μm$^3$ volume.

Pulses with 20 nJ are required for SNR=5, disregarding attenuation of laser power or loss of signal due to scattering. In reality when imaging deep into the brain, much higher pulse energies are needed for high SNR. Assuming $e^{-1}$ laser power loss to the focal plane, and an additional $e^{-1}$ signal loss due to scattering, 100 nJ pulses are needed for SNR=5. The high pulse energies reach peak fluences of <0.1 J/cm$^2$ at the focal plane, which is sufficiently low to avoid nonlinear ablation. Away from the focal plane, the peak fluence is reduced thanks to the rapidly diverging laser beam. Furthermore, the damage threshold away from the focal plane is increased because of the longer pulse width [96].

The high repetition rate (33 MHz) and high pulse energy for sufficient SNR results in a laser power of 0.7-3.5 W. Continuous imaging above 250 mW has shown to cause thermal damage. Several solutions exist for imaging with higher laser powers. First, an on-off imaging duty cycle can be used [99]. Extrapolating the 10 s on, 20 s off cycle used for imaging with 400 mW 250 μm deep into the brain, a duty cycle of 6 s on, 20 s off (for 0.7 W) or 1 s on, 20 s off (for 3.5 W) can be adopted. Although the imaging times are short, the system will be able to capture very fast brain dynamics. Additionally, heat can be carried away from the brain by using a cooled immersion medium. Perfusing an immersion medium has been found to quickly alter the temperature of the brain, even at depths of hundreds of microns [120]. Perhaps the most elegant solution towards avoiding thermal damage and increasing imaging duty cycles is to use shorter laser pulses. The shorter laser pulses would reach the intensities needed to excite two-photon fluorescence with lower pulse energies, and subsequently lower laser powers. For example, a laser generating 30 fs pulses would need 300 mW for SNR=5 without any losses from scattering, and 1.5 W for SNR=5 with the scattering approximation. Such short pulses have successfully been used for line-scanning two-photon imaging [36]. However, such short pulses are very sensitive to dispersion, and would require fine dispersion tuning to reach the transform-limited pulse width at the intended focus.

To summarize, the line excitation array detection concept was adapted for two-photon imaging. First, a two-photon LEAD microscope with galvanometric mirror scanning was built that could image a ~22×23 μm$^2$ FOV at 2,600 frames per second. The system's optical performance matched the simulated performance, including beam sizes, pulse widths, and axial sectioning. The two-photon LEAD microscope was able to image 0.5 μm diameter fluorescent beads with 1.1×1.4×5.4 μm$^2$ (xxyxz) resolution and signal-to-background ratios >80.

An improved two-photon LEAD microscope using an acousto-optic deflector for beam scanning was also designed. The system is expected to be capable of imaging a 64×150 μm$^2$ FOV at 200,000 frames per second, and the addition of an axial scanner would allow imaging at up to 400 volumes per second. The validated computational model was used to simulate optical performance.

The two-photon LEAD microscope has several limitations. The current setup provides lower than expected signal-to-noise ratio, likely due to the signal detection circuit. The preamplifier has a bandwidth of 20 MHz, which has a response slower than the fluorescence decay time. A faster preamplifier or a photon counting circuit would be more appropriate for two-photon imaging. The improved system with AOD scanning requires higher repetition rates, and higher laser powers to reach sufficient SNR, which can cause heating of the sample. However, such a challenge is not unique to the microscope, and other systems attempting to image as quickly would face the same issue. Finally, the two-photon LEAD microscope is sensitive to scattered light, which can cause image blurring [121]. Therefore, two-photon LEAD microscopy may be best suited for imaging lowly-scattering samples such as phantoms or the brains of small animals such as zebrafish embryos.

Despite these challenges, two-photon LEAD microscopy presents a promising approach towards imaging the brain at the timescales of neuron communication. The system with galvanometric mirror scanning is already at the cutting edge of speeds for two-photon imaging, while the AOD system can increase imaging speed until the limit of brain heating is reached.

The various embodiments described above are provided by way of illustration only and should not be construed to limit the scope of the present disclosure. Those skilled in the art will readily recognize that various modifications and changes may be made to the present disclosure without following the example embodiments and implementations illustrated and described herein, and without departing from the spirit and scope of the disclosure and claims here appended and those which may be filed in non-provisional patent application(s). Therefore, other modifications or embodiments as may be suggested by the teachings herein are particularly reserved.

REFERENCE LIST A

1. Ji, N., Freeman, J. & Smith, S. L. Technologies for imaging neural activity in large volumes. *Nat. Neurosci.* 19, 1154-1164 (2016).
2. Gong, Y. et al. High-speed recording of neural spikes in awake mice and flies with a fluorescent voltage sensor. *Science (80-.).* 2, 1361-1366 (2015).
3. Kaletta, T. & Hengartner, M. O. Finding function in novel targets: *C. elegans* as a model organism. *Nat. Rev.* 5, 387-398 (2006).
4. Reilly, L. P. O., Luke, C. J., Perlmutter, D. H., Silverman, G. A. & Pak, S. C. *C. elegans* in high-throughput drug discovery. *Adv Drug Deliv Rev* 247-253 (2014). doi: 10.1016/j.addr.2013.12.001.C.
5. Cornaglia, M., Lehnert, T. & Gijs, M. A. M. Microfluidic systems for high-throughput and high-content screening using the nematode *Caenorhabditis elegans*. *Lab Chip* (2017). doi:10.1039/C7LC00509A
6. Sirenko, O. et al. High-Content Assays for Characterizing the Viability and Morphology of 3D Cancer Spheroid Cultures. *Assay Drug Dev. Technol.* 13, 402-14 (2015).
7. Regmi, R., Mohan, K. & Mondal, P. P. High resolution light-sheet based high-throughput imaging cytometry system enables visualization of intra-cellular organelles. *AIP Adv.* 4, (2014).
8. Zhi, P., Chia, C. & Gleeson, P. A. Imaging and Quantitation Techniques for Tracking Cargo along Endosome-to-Golgi Transport Pathways. *Cells* 2, 105-123 (2013).
9. Chen, B.-C. et al. Lattice light-sheet microscopy: Imaging molecules to embryos at high spatiotemporal resolution. *Science (80-.).* 346, 1257998-1257998 (2014).
10. McGorty, R. et al. Open-top selective plane illumination microscope for conventionally mounted specimens. *Opt. Express* 23, 16142-53 (2015).
11. Prevedel, R. et al. Simultaneous whole-animal 3D imaging of neuronal activity using light-field microscopy. *Nat. Methods* 11, 727-30 (2014).
12. Schrödel, T., Prevedel, R., Aumayr, K., Zimmer, M. & Vaziri, A. Brain-wide 3D imaging of neuronal activity in *Caenorhabditis elegans* with sculpted light. *Nat. Methods* 10, 1013-1020 (2013).
13. Wu, J., Li, J. & Chan, R. K. Y. A light sheet based high throughput 3D-imaging flow cytometer for phytoplankton analysis. *Opt. Express* 21, 14474-80 (2013).
14. Lemon, W. C. et al. Whole-central nervous system functional imaging in larval *Drosophila*. *Nat. Commun.* 6, 7924 (2015).
15. Ahrens, M. B., Orger, M. B., Robson, D. N., Li, J. M. & Keller, P. J. Whole-brain functional imaging at cellular resolution using light-sheet microscopy. *Nat. Methods* 10, 413-420 (2013).
16. Mertz, J. & Kim, J. Scanning light-sheet microscopy in the whole mouse brain with HiLo background rejection. *J. Biomed. Opt.* 15, 16027 (2010).
17. Truong, T. V, Supatto, W., Koos, D. S., Choi, J. M. & Fraser, S. E. Deep and fast live imaging with two-photon scanned light-sheet microscopy. *Nat. Methods* 8, 757-760 (2011).
18. Trivedi, V. et al. Dynamic structure and protein expression of the live embryonic heart captured by 2-photon light sheet microscopy and retrospective registration. *Biomed. Opt. Express* 6, 2056 (2015).
19. Bouchard, M. B. et al. Swept confocally-aligned planar excitation (SCAPE) microscopy for high-speed volumetric imaging of behaving organisms. *Nat. Photonics* 9, 113-119 (2015).
20. Cheng, A., Gonçalves, J. T., Golshani, P., Arisaka, K. & Portera-Cailliau, C. Simultaneous two-photon calcium imaging at different depths with spatiotemporal multiplexing. *Nat. Methods* 8, 139-42 (2011).
21. Lechleiter, J. D., Lin, D.-T. & Sieneart, I. Multi-photon laser scanning microscopy using an acoustic optical deflector. *Biophys. J.* 83, 2292-9 (2002).
22. Roorda, R. D., Hohl, T. M., Toledo-Crow, R. & Miesenböck, G. Video-rate nonlinear microscopy of neuronal membrane dynamics with genetically encoded probes. *J. Neurophysiol.* 92, 609-21 (2004).
23. Chen, X., Leischner, U., Rochefort, N. L., Nelken, I. & Konnerth, A. Functional mapping of single spines in cortical neurons in vivo. *Nature* 475, 501-505 (2011).
24. Katona, G. et al. Fast two-photon in vivo imaging with three-dimensional random-access scanning in large tissue volumes. *Nat. Methods* 9, 201-208 (2012).
25. Nadella, K. M. N. S. et al. Random-access scanning microscopy for 3D imaging in awake behaving animals. *Nat. Methods* 13, 1001-1004 (2016).
26. Fernandez-Alfonso, T. et al. Monitoring synaptic and neuronal activity in 3D with synthetic and genetic indicators using a compact acousto-optic lens two-photon microscope. *J. Neurosci. Methods* 222, 69-81 (2014).
27. Grewe, B. F., Langer, D., Kasper, H., Kampa, B. M. & Helmchen, F. High-speed in vivo calcium imaging reveals neuronal network activity with near-millisecond precision. *Nat. Methods* 7, 399-405 (2010).
28. Salomé, R. et al. Ultrafast random-access scanning in two-photon microscopy using acousto-optic deflectors. *J. Neurosci. Methods* 154, 161-174 (2006).
29. Reddy, G., Kelleher, K., Fink, R. & Saggau, P. Three-dimensional random access multiphoton microscopy for functional imaging of neuronal activity. *Nat. Neurosci.* 11, 713-720 (2008).
30. Chan, J. C. K. et al. Digitally synthesized beat frequency-multiplexed fluorescence lifetime spectroscopy. *Biomed. Opt. Express* 5, 4428-36 (2014).
31. Howard, S. S., Straub, A., Horton, N. G., Kobat, D. & Xu, C. Frequency-multiplexed in vivo multiphoton phosphorescence lifetime microscopy. *Nat. Photonics* 7, 33-37 (2012).
32. Futia, G., Schlup, P., Winters, D. G. & Bartels, R. A. Spatially-chirped modulation imaging of absorbtion and fluorescent objects on single-element optical detector. *Opt. Express* 19, 1626-1640 (2011).

33. Kim, K. H. et al. Multifocal multiphoton microscopy based on multianode photomultiplier tubes. *Opt. Express* 15, 11658-11678 (2007).

34. Kumar, S. et al. Multifocal multiphoton excitation and time correlated single photon counting detection for 3-D fluorescence lifetime imaging. *Opt. Express* 15, 12548-12561 (2007).

35. Ragan, T. et al. High-resolution whole organ imaging using two-photon tissue cytometry. *J. Biomed. Opt.* 12, 14015 (2007).

36. Morley, J. F., Brignull, H. R., Weyers, J. J. & Morimoto, R. I. The threshold for polyglutamine-expansion protein aggregation and cellular toxicity is dynamic and influenced by aging in *Caenorhabditis elegans*. *Proc. Natl. Acad. Sci. U.S.A.* 99, 10417-22 (2002).

37. Mondal, S. et al. Large-scale microfluidics providing high-resolution and high-throughput screening of *Caenorhabditis elegans* poly-glutamine aggregation model. *Nat. Commun.* 7, 13023 (2016).

38. Ghorashian, N., Gökçe, S. K., Guo, S. X., Everett, W. N. & Ben-Yakar, A. An automated microfluidic multiplexer for fast delivery of *C. elegans* populations from multi-wells. *PLoS One* 8, e74480 (2013).

39. Hosaka, S., Seya, E., Harada, T. & Takanashi, A. High speed laser beam scanning using an acousto-optical deflector (AOD). *Jpn. J. Appl. Phys.* 26, 1026-1030 (1987).

40. Romer, G. R. B. E. & Bechtold, P. Electro-optic and acousto-optic laser beam scanners. *Phys. Procedia* 56, 29-39 (2014).

41. Munich, M. E. & Perona, P. Continuous dynamic time warping for translation-invariant curve alignment with applications to signature verification. *Proc. Seventh IEEE Int. Conf. Comput. Vis.* 15, 108-115 vol. 1 (1999).

42. Hamamatsu. *Photomultiplier Tubes: Basics and Applications*. (Hamamatsu Photonics K. K., 2007).

43. Sjöback, R. et al. Absorption and fluorescence properties of fluorescein. *Acta Part A Mol. Biomol.* 51, 1-15 (1995).

44. Pikto-Pietkiewicz, W. The effect of dronedarone on the frequency of cardiovascular events in patients with atrial fibrillation—ATHENA studies. *Kardiol. Pol.* 67, 455-456 (2009).

45. Cinar, H., Keles, S. & Jin, Y. Expression Profiling of GABAergic motor neurons in *Caenorhabditis elegans*. *Curr Biol* 15, 340-346 (2005).

46. Chen, L. et al. Axon regeneration pathways identified by systematic genetic screening in *C. elegans*. *Neuron* 71, 1043-57 (2011).

47. Visscher, K., Brackenhoff, G. J. & Visser, T. D. Fluorescence saturation in confocal microscopy. *Journal of Microscopy* 175, 162-165 (1994).

48. Eguchi, M. & Yamaguchi, S. In vivo and in vitro visualization of gene expression dynamics over extensive areas of the brain. *Neuroimage* 44, 1274-1283 (2009).

49. Coffman, V. C. & Wu, J.-Q. Counting protein molecules using quantitative fluorescence microscopy. *Trends Biochem. Sci.* 37, 499-506 (2012).

50. Botcherby, E. J. et al. Aberration-free three-dimensional multiphoton imaging of neuronal activity at kHz rates. *Proc. Natl. Acad. Sci. U.S.A.* 109, 2919-24 (2012).

51. Brenner, S. The genetics of *Caenorhabditis elegans*. *Genetics* 77, 71-94 (1974).

52. Unger, M. A., Chou, H. P., Thorsen, T., Scherer, A. & Quake, S. R. Monolithic microfabricated valves and pumps by multilayer soft lithography. *Science* 288, 113-6 (2000).

53. Kerse, C., Kalayciollu, H., Elahi, P., Akçaalan, Ö. & Ilday, F. Ö. 3.5-GHz intra-burst repetition rate ultrafast Yb-doped fiber laser. *Opt. Commun.* 366, 404-409 (2016).

54. Zhu, G., van Howe, J., Durst, M., Zipfel, W. & Xu, C. Simultaneous spatial and temporal focusing of femtosecond pulses. *Opt. Express* 13, 2153-9 (2005).

55. Tal, E., Oron, D. & Silberberg, Y. Improved depth resolution in video-rate line-scanning multiphoton microscopy using temporal focusing. *Opt. Lett.* 30, 1686 (2005).

56. Dana, H. et al. Hybrid multiphoton volumetric functional imaging of large-scale bioengineered neuronal networks. *Nat. Commun.* 5, 1-7 (2014).

57. Papagiakoumou, E. et al. Functional patterned multiphoton excitation deep inside scattering tissue. Nat. *Photonics* 7, 274-278 (2013).

58. Bégue, A. et al. Two-photon excitation in scattering media by spatiotemporally shaped beams and their application in optogenetic stimulation. *Biomed. Opt. Express* 4, 2869 (2013).

59. Dana, H. & Shoham, S. Remotely scanned multiphoton temporal focusing by axial grism scanning. *Opt. Lett.* 37, 2913 (2012).

60. Yih, J.-N. et al. Temporal focusing-based multiphoton excitation microscopy via digital micromirror device. *Opt. Lett.* 39, 3134-7 (2014).

61. Gobel, W. & Helmchen, F. New Angles on Neuronal Dendrites In Vivo. *J. Neurophysiol.* 98, 3770-3779 (2007).

62. Grewe, B. F., Voigt, F. F., van't Hoff, M. & Helmchen, F. Fast two-layer two-photon imaging of neuronal cell populations using an electrically tunable lens. *Biomed. Opt. Express* 2, 2035 (2011).

63. Zong, W. et al. Large-field high-resolution two-photon digital scanned light-sheet microscopy. *Cell Res.* 25, 254-257 (2015).

64. Botcherby, E. J. et al. Aberration-free three-dimensional multiphoton imaging of neuronal activity at kHz rates. *Proc. Natl. Acad. Sci. U.S.A.* 109, 2919-24 (2012).

65. Yang, W. et al. Simultaneous Multi-plane Imaging of Neural Circuits. *Neuron* 89, 284 (2016).

66. Anselmi, F., Ventalon, C., Begue, A., Ogden, D. & Emiliani, V. Three-dimensional imaging and photostimulation by remote-focusing and holographic light patterning. *Proc. Natl. Acad. Sci.* 108, 19504-19509 (2011).

REFERENCE LIST B

1. S. Weisenburger and V. Sandoghdar, "Light microscopy: an ongoing contemporary revolution," Contemp. Phys. 56(2), 123-143 (2015).

2. J. Lichtman and J. Conchello, "Fluorescence Microscopy," Nat. Methods 2(12), (2005).

3. W. R. Zipfel, R. M. Williams, and W. W. Webb, "Nonlinear magic: multiphoton microscopy in the biosciences.," Nat. Biotechnol. 21(11), 1369-1377 (2003).

4. J. Schmitt, "Optical Coherence Tomography (October): A Review," IEEE J. Sel. Top. Quantum Electron. 5(4), (1999).

5. Y. Zhang, H. Hong, and W. Cai, "Imaging with Raman Spectroscopy," Curr Pharm Biotechnol. 11(6), 654-661 (2010).

6. T.-W. Chen, T. J. Wardill, Y. Sun, S. R. Pulver, S. L. Renninger, A. Baohan, E. R. Schreiter, R. A. Kerr, M. B. Orger, V. Jayaraman, L. L. Looger, K. Svoboda, and D. S. Kim, "Ultrasensitive fluorescent proteins for imaging neuronal activity," Nature 499(7458), 295-300 (2013).
7. P. W. Winter and H. Shroff, "Faster fluorescence microscopy: Advances in high speed biological imaging," Curr. Opin. Chem. Biol. 20(1), 46-53 (2014).
8. M. Cornaglia, T. Lehnert, and M. A. M. Gijs, "Microfluidic systems for high-throughput and high-content screening using the nematode Caenorhabditis elegans," Lab Chip (2017).
9. T. Kaletta and M. O. Hengartner, "Finding function in novel targets: C. elegans as a model organism.," Nat. Rev. 5(5), 387-398 (2006).
10. A. G. Alexander, V. Marfil, and C. Li, "Use of C. elegans as a model to study Alzheimer's disease and other neurodegenerative diseases," Front. Genet. 5(JUL), 1-21 (2014).
11. S. Mondal, E. Hegarty, C. Martin, S. K. Gage, N. Ghorashian, and A. Ben-Yakar, "Large-scale microfluidics providing high-resolution and high-throughput screening of Caenorhabditis elegans poly-glutamine aggregation model," Nat. Commun. 7, 13023 (2016).
12. P. Penzes, M. E. Cahill, K. A. Jones, J. E. Vanleeuwen, and K. M. Woolfrey, "Dendritic spine pathology in neuropsychiatric disorders," Nat. Neurosci. 14(3), 285-293 (2011).
13. B. Bean, "The action potential in mammalian central neurons," Nat. Rev. Neurosci. 8, (2007).
14. G. Ariav, A. Polsky, and J. Schiller, "Submillisecond precision of the input-output transformation function mediated by fast sodium dendritic spikes in basal dendrites of CA1 pyramidal neurons.," J. Neurosci. 23(21), 7750-8 (2003).
15. K. Svoboda and R. Yasuda, "Principles of Two-Photon Excitation Microscopy and Its Applications to Neuroscience," Neuron 50(6), 823-839 (2006).
16. S. Hosaka, E. Seya, T. Harada, and A. Takanashi, "High speed laser beam scanning using an acousto-optical deflector (AOD)," Jpn. J. Appl. Phys. 26(7R), 1026-1030 (1987).
17. G. R. B. E. Romer and P. Bechtold, "Electro-optic and acousto-optic laser beam scanners," Phys. Procedia 56(C), 29-39 (2014).
18. C. Coates, B. Fowler, and G. Holst, "sCMOS: Scientific CMOS Technology, A High-performance Imaging Breakthrough," (June), 1-14 (2009).
19. Hamamatsu, Photomultiplier Tubes: Basics and Applications, 3rd ed. (Hamamatsu Photonics K. K., 2007).
20. M. C. Teich, K. Matsuo, and B. E. A. Saleh, "Excess Noise Factors for Conventional and Superlattice Avalanche Photodiodes and Photomultiplier Tubes," IEEE J. Quantum Electron. 22(8), 1184-1193 (1986).
21. J. Huisken, J. Swoger, D. B. Filippo, J. Witbrodt, and E. H. K. Stelzer, "Optical Sectioning Deep inside Live Embryos by Selective Plane Illumination Microscopy," Science (80-.). 305(5686), 1007-1009 (2004).
22. M. Duocastella, G. Sancataldo, P. Saggau, P. Ramoino, P. Bianchini, and A. Diaspro, "Fast Inertia-Free Volumetric Light-Sheet Microscope," ACS Photonics 4(7), 1797-1804 (2017).
23. M. B. Bouchard, V. Voleti, C. S. Mendes, C. Lacefield, W. B. Grueber, R. S. Mann, R. M. Bruno, and E. M. C. Hillman, "Swept confocally-aligned planar excitation (SCAPE) microscopy for high-speed volumetric imaging of behaving organisms," Nat. Photonics 9(2), 113-119 (2015).
24. J. Wu, J. Li, and R. K. Y. Chan, "A light sheet based high throughput 3D-imaging flow cytometer for phytoplankton analysis.," Opt. Express 21(12), 14474-80 (2013).
25. J. Wu and R. K. Y. Chan, "A fast fluorescence imaging flow cytometer for phytoplankton analysis.," Opt. Express 21(20), 23921-6 (2013).
26. R. McGorty, H. Liu, D. Kamiyama, Z. Dong, S. Guo, and B. Huang, "Open-top selective plane illumination microscope for conventionally mounted specimens.," Opt. Express 23(12), 16142-53 (2015).
27. P. J. Keller, A. D. Schmidt, J. Wittbrodt, and E. H. K. Stelzer, "Reconstruction of Zebrafish Early Embryonic Development by Scanned Light Sheet Microscopy," Science (80-.). 322(November), 1065-1069 (2008).
28. P. J. Keller and M. B. Ahrens, "Visualizing whole-brain activity and development at the single-cell level using light-sheet microscopy," Neuron 85(3), 462-483 (2015).
29. M. B. Ahrens, M. B. Orger, D. N. Robson, J. M. Li, and P. J. Keller, "Whole-brain functional imaging at cellular resolution using light-sheet microscopy," Nat. Methods 10(5), 413-420 (2013).
30. W. C. Lemon, S. R. Pulver, B. Höckendorf, K. McDole, K. Branson, J. Freeman, and P. J. Keller, "Whole-central nervous system functional imaging in larval Drosophila," Nat. Commun. 6(May), 7924 (2015).
31. J. Mertz and J. Kim, "Scanning light-sheet microscopy in the whole mouse brain with HiLo background rejection," J. Biomed. Opt. 15(1), 016027 (2010).
32. B.-C. Chen, W. R. Legant, K. Wang, L. Shao, D. E. Milkie, M. W. Davidson, C. Janetopoulos, X. S. Wu, J. A. Hammer, Z. Liu, B. P. English, Y. Mimori-Kiyosue, D. P. Romero, A. T. Ritter, J. Lippincott-Schwartz, L. Fritz-Laylin, R. D. Mullins, D. M. Mitchell, J. N. Bembenek, A.-C. Reymann, R. Bohme, S. W. Grill, J. T. Wang, G. Seydoux, U. S. Tulu, D. P. Kiehart, and E. Betzig, "Lattice light-sheet microscopy: Imaging molecules to embryos at high spatiotemporal resolution," Science (80-.). 346 (6208), 1257998-1257998 (2014).
33. T. V Truong, W. Supatto, D. S. Koos, J. M. Choi, and S. E. Fraser, "Deep and fast live imaging with two-photon scanned light-sheet microscopy," Nat. Methods 8(9), 757-760 (2011).
34. T. Schrödel, R. Prevedel, K. Aumayr, M. Zimmer, and A. Vaziri, "Brain-wide 3D imaging of neuronal activity in Caenorhabditis elegans with sculpted light," Nat. Methods 10(10), 1013-1020 (2013).
35. G. Zhu, J. van Howe, M. Durst, W. Zipfel, and C. Xu, "Simultaneous spatial and temporal focusing of femtosecond pulses.," Opt. Express 13(6), 2153-9 (2005).
36. E. Tal, D. Oron, and Y. Silberberg, "Improved depth resolution in video-rate line-scanning multiphoton microscopy using temporal focusing," Opt. Lett. 30(13), 1686 (2005).
37. H. Dana, A. Marom, S. Paluch, R. Dvorkin, I. Brosh, and S. Shoham, "Hybrid multiphoton volumetric functional imaging of large-scale bioengineered neuronal networks," Nat. Commun. 5, 1-7 (2014).
38. R. Salomé, Y. Kremer, S. Dieudonné, J. F. Léger, O. Krichevsky, C. Wyart, D. Chatenay, and L. Bourdieu, "Ultrafast random-access scanning in two-photon microscopy using acousto-optic deflectors," J. Neurosci. Methods 154(1-2), 161-174 (2006).

39. V. Iyer, T. Hoogland, and P. Saggau, "Fast Functional Imaging of Single Neurons Using Random-Access Multiphoton (RAMP) Microscopy," J. Neurophysiol. 95(1), 535-545 (2005).
40. B. F. Grewe, D. Langer, H. Kasper, B. M. Kampa, and F. Helmchen, "High-speed in vivo calcium imaging reveals neuronal network activity with near-millisecond precision," Nat. Methods 7(5), 399-405 (2010).
41. G. Reddy and P. Saggau, "Fast three-dimensional laser scanning scheme using acousto-optic deflectors.," J. Biomed. Opt. 10(6), 064038 (2005).
42. G. Reddy, K. Kelleher, R. Fink, and P. Saggau, "Three-dimensional random access multiphoton microscopy for functional imaging of neuronal activity," Nat. Neurosci. 11(6), 713-720 (2008).
43. T. Fernandez-Alfonso, K. M. N. S. Nadella, M. F. Iacaruso, B. Pichler, H. Ros, P. A. Kirkby, and R. A. Silver, "Monitoring synaptic and neuronal activity in 3D with synthetic and genetic indicators using a compact acousto-optic lens two-photon microscope," J. Neurosci. Methods 222, 69-81 (2014).
44. X. Chen, U. Leischner, N. L. Rochefort, I. Nelken, and A. Konnerth, "Functional mapping of single spines in cortical neurons in vivo," Nature 475(7357), 501-505 (2011).
45. G. Katona, G. Szalay, P. Maák, A. Kaszás, M. Veress, D. Hillier, B. Chiovini, E. S. Vizi, B. Roska, and B. Rózsa, "Fast two-photon in vivo imaging with three-dimensional random-access scanning in large tissue volumes," Nat. Methods 9(2), 201-208 (2012).
46. K. M. N. S. Nadella, H. Roš, C. Baragli, V. A. Griffiths, G. Konstantinou, T. Koimtzis, G. J. Evans, P. A. Kirkby, and R. A. Silver, "Random-access scanning microscopy for 3D imaging in awake behaving animals," Nat. Methods 13(12), 1001-1004 (2016).
47. J. D. Lechleiter, D.-T. Lin, and I. Sieneart, "Multi-photon laser scanning microscopy using an acoustic optical deflector.," Biophys. J. 83(4), 2292-9 (2002).
48. R. D. Roorda, T. M. Hohl, R. Toledo-Crow, and G. Miesenböck, "Video-rate nonlinear microscopy of neuronal membrane dynamics with genetically encoded probes.," J. Neurophysiol. 92(1), 609-21 (2004).
49. R. Prevedel, A. J. Verhoef, A. J. Pernía-Andrade, S. Weisenburger, B. S. Huang, T. Nöbauer, A. Fernández, J. E. Delcour, P. Golshani, A. Baltuska, and A. Vaziri, "Fast volumetric calcium imaging across multiple cortical layers using sculpted light," Nat. Methods 13(12), 1021-1028 (2016).
50. R. Prevedel, Y.-G. Yoon, M. Hoffmann, N. Pak, G. Wetzstein, S. Kato, T. Schrödel, R. Raskar, M. Zimmer, E. S. Boyden, and A. Vaziri, "Simultaneous whole-animal 3D imaging of neuronal activity using light-field microscopy," Nat. Methods 11(7), 727-730 (2014).
51. S. Abrahamsson, J. Chen, B. Hajj, S. Stallinga, A. Y. Katsov, J. Wisniewski, G. Mizuguchi, P. Soule, F. Mueller, C. D. Darzacq, X. Darzacq, C. Wu, C. I. Bargmann, D. A. Agard, M. Dahan, and M. G. L. Gustafsson, "Fast multicolor 3D imaging using aberration-corrected multifocus microscopy," Nat. Methods 10(1), 60-63 (2013).
52. O. E. Olarte, J. Andilla, D. Artigas, and P. Loza-Alvarez, "Decoupled illumination detection in light sheet microscopy for fast volumetric imaging," Optica 2(8), 702 (2015).
53. S. Quirin, J. Jackson, D. S. Peterka, and R. Yuste, "Simultaneous imaging of neural activity in three dimensions," Front. Neural Circuits 8(April), 1-11 (2014).
54. S. Quirin, N. Vladimirov, C.-T. Yang, D. S. Peterka, R. Yuste, and M. B. Ahrens, "Calcium imaging of neural circuits with extended depth-of-field light-sheet microscopy," Opt. Lett. 41(5), 855 (2016).
55. K. H. Kim, C. Buehler, K. Bahlmann, T. Ragan, W.-C. a Lee, E. Nedivi, E. L. Heffer, S. Fantini, and P. T. C. So, "Multifocal multiphoton microscopy based on multianode photomultiplier tubes.," Opt. Express 15(18), 11658-11678 (2007).
56. T. Ragan, J. D. Sylvan, K. H. Kim, H. Huang, K. Bahlmann, R. T. Lee, and P. T. C. So, "High-resolution whole organ imaging using two-photon tissue cytometry," J. Biomed. Opt. 12(1), 014015 (2007).
57. J. W. Cha, E. Y. S. Yew, D. Kim, J. Subramanian, E. Nedivi, and P. T. C. So, "Non-descanned multifocal multiphoton microscopy with a multianode photomultiplier tube," AIP Adv. 5(8), (2015).
58. S. Kumar, C. Dunsby, P. a a De Beule, D. M. Owen, U. Anand, P. M. P. Lanigan, R. K. P. Benninger, D. M. Davis, M. a a Neil, P. Anand, C. Benham, A. Naylor, and P. M. W. French, "Multifocal multiphoton excitation and time correlated single photon counting detection for 3-D fluorescence lifetime imaging.," Opt. Express 15(20), 12548-12561 (2007).
59. A. Cheng, J. T. Gonçalves, P. Golshani, K. Arisaka, and C. Portera-Cailliau, "Simultaneous two-photon calcium imaging at different depths with spatiotemporal multiplexing," Nat. Methods 8(2), 139-42 (2011).
60. K. Goda, K. K. Tsia, and B. Jalali, "Serial time-encoded amplified imaging for real-time observation of fast dynamic phenomena," Nature 458(7242), 1145-1149 (2009).
61. K. Goda, a. Ayazi, D. R. Gossett, J. Sadasivam, C. K. Lonappan, E. Sollier, a. M. Fard, S. C. Hur, J. Adam, C. Murray, C. Wang, N. Brackbill, D. Di Carlo, and B. Jalali, "High-throughput single-microparticle imaging flow analyzer," Proc. Natl. Acad. Sci. 109(29), 11630-11635 (2012).
62. B. T. Bosworth, J. R. Stroud, D. N. Tran, T. D. Tran, S. Chin, and M. A. Foster, "High-speed flow microscopy using compressed sensing with ultrafast laser pulses," Opt. Express 23(8), 10521-10532 (2015).
63. M. D. Young, E. C. Barbano, N. Worts, J. J. Field, C. Hoy, K. A. Wernsing, R. A. Bartels, and J. Squier, "Spatial Frequency Modulated Imaging (SPIFI) with amplitude or phase grating from a spatial light modulator," 100692P (2017).
64. J. J. Field, D. G. Winters, and R. A. Bartels, "Phase-sensitive fluorescent imaging with coherent reconstruction," arXiv (2015).
65. S. S. Howard, A. Straub, N. G. Horton, D. Kobat, and C. Xu, "Frequency-multiplexed in vivo multiphoton phosphorescence lifetime microscopy," Nat. Photonics 7(1), 33-37 (2012).
66. E. D. Diebold, B. W. Buckley, D. R. Gossett, and B. Jalali, "Digitally-synthesized beat frequency multiplexing for sub-millisecond fluorescence microscopy," Nat. Photonics 7(10), 806-810 (2013).
67. H. Mikami, J. Harmon, H. Kobayashi, S. Hamad, Y. Wang, O. Iwata, K. Suzuki, T. Ito, Y. Aisaka, N. Kutsuna, K. Nagasawa, H. Watarai, Y. Ozeki, and K. Goda, "Ultrafast confocal fluorescence microscopy beyond the fluorescence lifetime limit," Optica 5(2), 117 (2018).
68. A. Kazemipour, O. Novak, D. Flickinger, J. S. Marvin, J. King, P. Borden, S. Druckmann, K. Svoboda, L. L. Looger, and K. Podgorski, "Kilohertz frame-rate two-photon tomography," bioRxiv 357269 (2018).

69. S. J. Gosai, J. H. Kwak, C. J. Luke, 0. S. Long, D. E. King, K. J. Kovatch, P. A. Johnston, T. Y. Shun, J. S. Lazo, D. H. Perlmutter, G. A. Silverman, and S. C. Pak, "Automated high-content live animal drug screening using *C. elegans* expressing the aggregation prone serpin αl-antitrypsin Z," PLoS One 5(11), (2010).

70. A. Ben-Yakar, N. Chronis, and H. Lu, "Microfluidics for the analysis of behavior, nerve regeneration, and neural cell biology in *C. elegans*.," Curr. Opin. Neurobiol. 19(5), 561-567 (2009).

71. M. M. Crane, J. N. Stirman, C. Y. Ou, P. T. Kurshan, J. M. Rehg, K. Shen, and H. Lu, "Autonomous screening of *C. elegans* identifies genes implicated in synaptogenesis," Nat. Methods 9(10), 977-980 (2012).

72. R. Pulak, Techniques for Analysis, Sorting, and Dispensing of *C. Elegans* on the COPAS Flow-Sorting System (2006), 351.

73. C. Martin, T. Li, E. Hegarty, P. Zhao, S. Mondal, and A. Ben-Yakar, "Line excitation array detection microscopy at 0.8 million frames per second," Nat. Commun. 9, (2018).

74. M. A. Unger, H. P. Chou, T. Thorsen, A. Scherer, and S. R. Quake, "Monolithic microfabricated valves and pumps by multilayer soft lithography.," Science 288(5463), 113-6 (2000).

75. M. E. Munich and P. Perona, "Continuous dynamic time warping for translation-invariant curve alignment with applications to signature verification," Proc. Seventh IEEE Int. Conf. Comput. Vis. 15(1), 108-115 vol. 1 (1999).

76. R. Mcgorty, D. Xie, and B. Huang, "High-NA open-top selective-plane illumination microscopy for biological imaging," Opt. Express 25(15), 17798 (2017).

77. R. Sjöback, J. Nygren, M. Kubista, R. Sjback, J. Nygren, and M. Kubista, "Absorption and fluorescence properties of fluorescein," . . . Acta Part A Mol. Biomol. . . . 51, (1995).

78. K. Visscher, G. J. Brackenhoff, and T. D. Visser, "Fluorescence saturation in confocal microscopy," J. Microsc. 175(2), 162-165 (1994).

79. J. F. Morley, H. R. Brignull, J. J. Weyers, and R. I. Morimoto, "The threshold for polyglutamine-expansion protein aggregation and cellular toxicity is dynamic and influenced by aging in *Caenorhabditis elegans*.," Proc. Natl. Acad. Sci. U.S.A. 99(16), 10417-22 (2002).

80. W. Pikto-Pietkiewicz, "The effect of dronedarone on the frequency of cardiovascular events in patients with atrial fibrillation—ATHENA studies," Kardiol. Pol. 67(4), 455-456 (2009).

81. H. Cinar, S. Keles, and Y. Jin, "Expression Profiling of GABAergic motor neurons in *Caenorhabditis elegans*," Curr Biol 15(4), 340-346 (2005).

82. L. Chen, Z. Wang, A. Ghosh-Roy, T. Hubert, D. Yan, S. O'Rourke, B. Bowerman, Z. Wu, Y. Jin, and A. D. Chisholm, "Axon Regeneration Pathways Identified by Systematic Genetic Screening in *C. elegans*," Neuron 71(6), 1043-1057 (2011).

83. M. Eguchi and S. Yamaguchi, "In vivo and in vitro visualization of gene expression dynamics over extensive areas of the brain," Neuroimage 44(4), 1274-1283 (2009).

84. N. Ghorashian, S. K. Göçe, S. X. Guo, W. N. Everett, and A. Ben-Yakar, "An automated microfluidic multiplexer for fast delivery of *C. elegans* populations from multi-wells.," PLoS One 8(9), e74480 (2013).

85. R. Regmi, K. Mohan, and P. P. Mondal, "High resolution light-sheet based high-throughput imaging cytometry system enables visualization of intra-cellular organelles," AIP Adv. 4(9), (2014).

86. P. Zhi, C. Chia, and P. A. Gleeson, "Imaging and Quantitation Techniques for Tracking Cargo along Endosome-to-Golgi Transport Pathways," Cells 2, 105-123 (2013).

87. O. Sirenko, T. Mitlo, J. Hesley, S. Luke, W. Owens, and E. F. Cromwell, "High-Content Assays for Characterizing the Viability and Morphology of 3D Cancer Spheroid Cultures," Assay Drug Dev. Technol. 13(7), 402-14 (2015).

88. V. C. Coffman and J.-Q. Wu, "Counting protein molecules using quantitative fluorescence microscopy," Trends Biochem. Sci. 37(11), 499-506 (2012).

89. V. L. Feigin, "Global, regional, and national burden of neurological disorders during 1990-2015: a systematic analysis for the Global Burden of Disease Study 2015," Lancet Neurol. 16(11), 877-897 (2017).

90. F. Buchthal and A. Rosenfalck, "Evoked action potentials and conduction velocity in human sensory nerves," Brain Res. 3(1), (1966).

91. J. Jacobs, R. Zelmann, J. Jirsch, R. Chander, C. Chatillon, F. Dubeau, and J. Gotman, "High frequency oscillations (80-500 Hz) in the preictal period in patients with focal seizures," Epilepsia 50(7), 1780-1792 (2009).

92. C. Grienberger and A. Konnerth, "Imaging Calcium in Neurons," Neuron 73(5), 862-885 (2012).

93. M. Mank, O. Griesbeck, and F. S. E. T. C, "Genetically Encoded Calcium Indicators," Chem. Rev. 108(5), 1550-1564 (2008).

94. M. Z. Lin and M. J. Schnitzer, "Genetically encoded indicators of neuronal activity," Nat. Neurosci. 19(9), 1142-1153 (2016).

95. H. H. Yang and F. St-Pierre, "Genetically Encoded Voltage Indicators: Opportunities and Challenges," J. Neurosci. 36(39), 9977-9989 (2016).

96. A. Vogel, J. Noack, G. Hüttman, and G. Paltauf, "Mechanisms of femtosecond laser nanosurgery of cells and tissues," Appl. Phys. B 81(8), 1015-1047 (2005).

97. P. Theer, M. T. Hasan, and W. Denk, "Two-photon imaging to a depth of 1000 μm in living brains by use of a Ti:Al_2O_3 regenerative amplifier," Opt. Lett. 28(12), 1022 (2003).

98. A. Picot, S. Dominguez, C. Liu, I. W. Chen, D. Tanese, E. Ronzitti, P. Berto, E. Papagiakoumou, D. Oron, G. Tessier, B. C. Forget, and V. Emiliani, "Temperature Rise under Two-Photon Optogenetic Brain Stimulation," Cell Rep. 24(5), 1243-1253.e5 (2018).

99. K. Podgorski and G. Ranganathan, "Brain heating induced by near-infrared lasers during multiphoton microscopy," J. Neurophysiol. 116(3), 1012-1023 (2016).

100. G. Zhu, J. van Howe, M. Durst, W. Zipfel, and C. Xu, "Simultaneous spatial and temporal focusing of femtosecond pulses," Opt. Express 13(6), 2153 (2005).

101. D. Oron, E. Tal, and Y. Silberberg, "Scanningless depth-resolved microscopy," Opt. Express 13(5), 1468 (2005).

102. M. E. Durst, G. Zhu, and C. Xu, "Simultaneous spatial and temporal focusing for axial scanning," Opt. Express 14(25), 12243 (2006).

103. E. Block and J. Squier, "Simultaneous spatial and temporal focusing for tissue ablation," Biomed. Opt. Express 4(6), (2013).

104. H. Dana, N. Kruger, A. Ellman, and S. Shoham, "Line temporal focusing characteristics in transparent and scattering media," Opt. Express 21(5), 5677 (2013).
105. E. Papagiakoumou, A. Bégue, B. Leshem, O. Schwartz, B. M. Stell, J. Bradley, D. Oron, and V. Emiliani, "Functional patterned multiphoton excitation deep inside scattering tissue," Nat. Photonics 7(4), 274-278 (2013).
106. T. Kasahara, "Microscope Objective Lens," (2002).
107. C. Xu, J. Guild, W. Webb, and W. Denk, "Determination of absolute two-photon excitation cross sections by in situ second-order autocorrelation.," Opt. Lett. 20(23), 2372 (1995).
108. M. E. Durst, G. Zhu, and C. Xu, "Simultaneous spatial and temporal focusing in nonlinear microscopy," Opt. Commun. 281(7), 1796-1805 (2008).
109. C. Xu and W. W. Webb, "Measurement of two-photon excitation cross sections of molecular fluorophores with data from 690 to 1050 nm," J. Opt. Soc. Am. B 13(3), 481 (1996).
110. D. Oron and Y. Silberberg, "Temporal focusing microscopy," Cold Spring Harb. Protoc. 2015(2), 145-151 (2015).
111. W. Gobel and F. Helmchen, "New Angles on Neuronal Dendrites In Vivo," J. Neurophysiol. 98(6), 3770-3779 (2007).
112. B. F. Grewe, F. F. Voigt, M. van't Hoff, and F. Helmchen, "Fast two-layer two-photon imaging of neuronal cell populations using an electrically tunable lens," Biomed. Opt. Express 2(7), 2035 (2011).
113. J. M. Jabbour, B. H. Malik, C. Olsovsky, R. Cuenca, S. Cheng, J. A. Jo, Y.-S. L. Cheng, J. M. Wright, and K. C. Maitland, "Optical axial scanning in confocal microscopy using an electrically tunable lens," Biomed. Opt. Express 5(2), 645 (2014).
114. Y. Nakai, M. Ozeki, T. Hiraiwa, R. Tanimoto, A. Funahashi, N. Hiroi, A. Taniguchi, S. Nonaka, V. Boilot, R. Shrestha, J. Clark, N. Tamura, V. M. Draviam, and H. Oku, "High-speed microscopy with an electrically tunable lens to image the dynamics of in vivo molecular complexes," Rev. Sci. Instrum. 86(1), (2015).
115. K. Philipp, A. Smolarski, N. Koukourakis, A. Fischer, M. Stürmer, U. Wallrabe, and J. W. Czarske, "Volumetric HiLo microscopy employing an electrically tunable lens," Opt. Express 24(13), 15029 (2016).
116. P. A. Kirkby, K. M. N. Srinivas Nadella, and R. A. Silver, "A compact acousto-optic lens for 2D and 3D femtosecond based 2-photon microscopy," Opt. Express 18(13), 13720 (2010).
117. a Kaplan, N. Friedman, and N. Davidson, "Acousto-optic lens with very fast focus scanning.," Opt. Lett. 26(14), 1078-1080 (2001).
118. E. J. Botcherby, C. W. Smith, M. M. Kohl, D. Debarre, M. J. Booth, R. Juskaitis, O. Paulsen, and T. Wilson, "Aberration-free three-dimensional multiphoton imaging of neuronal activity at kHz rates," Proc. Natl. Acad. Sci. 109(8), 2919-2924 (2012).
119. K. M. Dean, P. Roudot, E. S. Welf, G. Danuser, and R. Fiolka, "Deconvolution-free Subcellular Imaging with Axially Swept Light Sheet Microscopy," Biophys. J. 108(12), 2807-2815 (2015).
120. A. S. Kalmbach and J. Waters, "Brain surface temperature under a craniotomy," J. Neurophysiol. 108(11), 3138-3146 (2012).
121. P. Rupprecht, R. Prevedel, F. Groessl, W. E. Haubensak, and A. Vaziri, "Optimizing and extending light-sculpting microscopy for fast functional imaging in neuroscience," Biomed. Opt. Express 6(2), 353 (2015).

What is claimed is:

1. A system for imaging of a subject of interest, comprising:
an optical beam source configured to provide an excitation beam;
one or more beam scanners configured for line scanning of the excitation beam across the subject; and
one or more linear arrays of optical detectors configured for parallel detection of optical signals from different segments of the subject in response to the excitation beam,
wherein the one or more beam scanners comprise an acousto-optic deflector (AOD) coupled to the optical beam source, and
wherein the AOD is comprised of a crystal in a longitudinal mode or a crystal in a shear mode.

2. The system of claim 1, wherein the one or more beam scanners comprise one or more scanning mirrors coupled to the optical beam source.

3. The system of claim 1, wherein the one or more beam scanners comprise an electro-optic deflector (EOD) coupled to the optical beam source.

4. The system of claim 1, wherein the one or more linear arrays of optical detectors comprise a photomultiplier tube (PMT) array, a silicon photomultiplier (SiPM) array, avalanche photodiode array, a linescan camera with an intensifier, or a linescan camera without an intensifier.

5. The system of claim 1, further comprising:
an optical feedback system configured to monitor location of the excitation beam during scanning, wherein the optical feedback system comprises an optical detector and slit configured to monitor location of a second order diffraction beam or calibration beam for calibrating location of the excitation beam.

6. The system of claim 1, wherein the system is configured for nonlinear microscopy.

7. The system of claim 6, wherein the system is configured to excite a plane that is from −80° to 80° at an angle to an optical axis and image through a single objective.

8. A system for imaging of a subject of interest, comprising:
an optical beam source configured to provide an excitation beam;
one or more beam scanners configured for line scanning of the excitation beam across the subject; and
one or more linear arrays of optical detectors configured for parallel detection of optical signals from different segments of the subject in response to the excitation beam,
wherein the one or more beam scanners are configured for random access scanning.

9. A system for imaging of a subject of interest, comprising:
an optical beam source configured to provide an excitation beam;
one or more beam scanners configured for line scanning of the excitation beam across the subject;
one or more linear arrays of optical detectors configured for parallel detection of optical signals from different segments of the subject in response to the excitation beam; and
a parallel data acquisition system coupled to the one or more linear arrays of optical detectors and an image reconstruction system coupled to one or more multichannel data acquisition devices, configured to generate a frame of the subject based on the detected optical signals.

10. The system of claim 9, wherein the one or more multi-channel data acquisition devices includes a plurality of multi-channel data acquisition devices that operate in different computers that are synchronized to collect data from the one or more linear arrays optical detectors.

11. The system of claim 9, wherein the one or more linear arrays of optical detectors are configured for detecting one or more signals from a complete or partial segments of the subject in response to the excitation beam line as the beam scans and such that a full image frame is generated for each scan cycle.

12. A system for imaging of a subject of interest, comprising:
   an optical beam source configured to provide an excitation beam;
   one or more beam scanners configured for line scanning of the excitation beam across the subject; and
   one or more linear arrays of optical detectors configured for parallel detection of optical signals from different segments of the subject in response to the excitation beam,
   the system being configured for flow cytometry, wherein the subject is in motion through the system during the scanning.

13. The system of claim 12, wherein the system is further configured to correct optical aberrations using customized objectives or an objective-device immersion system or adaptive optics or a prism below a microfluidic device, in a path of the excitation beam and collection signal or a tilted lens or tilted piece of glass in a conjugate imaging plane of an imaging path.

14. The system of claim 12, wherein the system is further configured to generate an excitation beam in a configuration of a Gaussian beam or Bessel beam or Airy beam.

15. The system of claim 12, wherein the system is configured for nonlinear microscopy.

16. The system of claim 12, wherein the one or more beam scanners comprise one of an acousto-optic deflector (AOD) coupled to the optical beam source, an electro-optic deflector (EOD) coupled to the optical beam source, and one or more scanning mirrors coupled to the optical beam source.

17. A system for imaging of a subject of interest, comprising:
   an optical beam source configured to provide an excitation beam;
   one or more beam scanners configured for line scanning of the excitation beam across the subject;
   one or more linear arrays of optical detectors configured for parallel detection of optical signals from different segments of the subject in response to the excitation beam; and
   a simultaneous spatial and temporal focusing (SSTF) system for increasing axial resolution, wherein the SSFT system comprises a diffraction grating, a grism, or a digital micromirror device (DMD) configured as a grating,
   wherein the system is configured for nonlinear microscopy.

18. A system for imaging of a subject of interest, comprising:
   an optical beam source configured to provide an excitation beam;
   one or more beam scanners configured for line scanning of the excitation beam across the subject;
   one or more linear arrays of optical detectors configured for parallel detection of optical signals from different segments of the subject in response to the excitation beam;
   an axial scanning system, the axial scanning system comprising at least one of:
   a piezoelectric stage to which an objective is mounted, moving along an optical axis;
   a tunable lens before the objective;
   remote focusing in which an axially scanned mirror is imaged onto the subject; and
   a spatial light modulator configured as a reflective lens before the objective,
   wherein the system is configured for nonlinear microscopy.

19. A system for imaging of a subject of interest, comprising:
   an optical beam source configured to provide an excitation beam;
   one or more beam scanners configured for line scanning of the excitation beam across the subject; and
   one or more linear arrays of optical detectors configured for parallel detection of optical signals from different segments of the subject in response to the excitation beam,
   wherein the one or more linear arrays of optical detectors are combined with spectral filters and configured for multi-color imaging.

20. A system for imaging of a subject of interest, comprising:
   an optical beam source configured to provide an excitation beam;
   one or more beam scanners configured for line scanning of the excitation beam across the subject; and
   one or more linear arrays of optical detectors configured for parallel detection of optical signals from different segments of the subject in response to the excitation beam,
   wherein the system is further configured to shape the laser excitation beam entering an AOD aperture to have a width equal to or less than an aperture width.

* * * * *